(12) United States Patent
Novak, Jr. et al.

(10) Patent No.: US 12,390,114 B2
(45) Date of Patent: Aug. 19, 2025

(54) WEARABLE DEVICE FOR MONITORING HEALTH STATUS

(71) Applicant: Masimo Corporation, Irvine, CA (US)

(72) Inventors: Jerome J. Novak, Jr., Lake Forest, CA (US); Omar Ahmed, Lake Forest, CA (US); Kostantinos Michalopoulos, Irvine, CA (US); Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 349 days.

(21) Appl. No.: 17/207,055

(22) Filed: Mar. 19, 2021

(65) Prior Publication Data
US 2021/0290177 A1    Sep. 23, 2021

Related U.S. Application Data

(60) Provisional application No. 63/106,273, filed on Oct. 27, 2020, provisional application No. 63/065,961, (Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0004* (2013.01); *A61B 5/0008* (2013.01); (Continued)

(58) Field of Classification Search
CPC .... A61B 2562/0271; A61B 5/00–7495; H04B 17/318; G16H 50/80; G08B 21/0247
See application file for complete search history.

(56) References Cited

U.S. PATENT DOCUMENTS

| 4,960,128 A | 10/1990 | Gordon et al. |
| 4,964,408 A | 10/1990 | Hink et al. |

(Continued)

FOREIGN PATENT DOCUMENTS

| EP | 3 541 273 | 4/2021 |
| WO | WO 2010/099488 | 9/2010 |

(Continued)

OTHER PUBLICATIONS

US 2024/0016391 A1, 01/2024, Lapotko et al. (withdrawn)
(Continued)

*Primary Examiner* — Tse W Chen
*Assistant Examiner* — Evelyn Grace Park
(74) *Attorney, Agent, or Firm* — Knobbe, Martens, Olson & Bear, LLP

(57) ABSTRACT

A system for remotely monitoring and managing health statuses of a plurality of users includes software instructions storable on a memory device usable by a computing device, the software instructions causing a hardware processor of the computing device to receive a plurality of sets of health-related information from a plurality of mobile computing devices of a plurality of users. The health-related information includes physiological information derived from wearable devices of the users indicative of an onset of symptoms associated with an infection, contact tracing data, and diagnosis data. The hardware processor determines exposure levels based on at least the contact tracing data, and determines user-specific risk states based on physiological information, diagnosis data, and exposure levels.

16 Claims, 30 Drawing Sheets

Related U.S. Application Data filed on Aug. 14, 2020, provisional application No. 63/056,925, filed on Jul. 27, 2020, provisional application No. 63/049,478, filed on Jul. 8, 2020, provisional application No. 63/010,669, filed on Apr. 15, 2020, provisional application No. 62/992,779, filed on Mar. 20, 2020, provisional application No. 62/992,808, filed on Mar. 20, 2020.

(51) Int. Cl.

| | |
|---|---|
| *A61B 5/01* | (2006.01) |
| *A61B 5/024* | (2006.01) |
| *A61B 5/026* | (2006.01) |
| *A61B 5/08* | (2006.01) |
| *A61B 5/145* | (2006.01) |
| *A61B 5/1455* | (2006.01) |
| *G06F 3/04842* | (2022.01) |
| *G06F 9/451* | (2018.01) |
| *G16H 10/60* | (2018.01) |
| *G16H 15/00* | (2018.01) |
| *G16H 40/20* | (2018.01) |
| *G16H 40/67* | (2018.01) |
| *G16H 50/20* | (2018.01) |
| *G16H 50/30* | (2018.01) |
| *G16H 50/70* | (2018.01) |
| *G16H 50/80* | (2018.01) |
| *H04B 17/318* | (2015.01) |
| *H04W 4/021* | (2018.01) |

(52) U.S. Cl.
CPC ............ *A61B 5/002* (2013.01); *A61B 5/0022* (2013.01); *A61B 5/01* (2013.01); *A61B 5/0205* (2013.01); *A61B 5/08* (2013.01); *A61B 5/0816* (2013.01); *A61B 5/14542* (2013.01); *A61B 5/6801* (2013.01); *A61B 5/6814* (2013.01); *A61B 5/6823* (2013.01); *A61B 5/6824* (2013.01); *A61B 5/6826* (2013.01); *A61B 5/7275* (2013.01); *A61B 5/7282* (2013.01); *A61B 5/7435* (2013.01); *A61B 5/746* (2013.01); *A61B 5/7465* (2013.01); *A61B 5/747* (2013.01); *A61B 5/7475* (2013.01); *G06F 9/451* (2018.02); *G16H 10/60* (2018.01); *G16H 15/00* (2018.01); *G16H 40/20* (2018.01); *G16H 40/67* (2018.01); *G16H 50/20* (2018.01); *G16H 50/30* (2018.01); *G16H 50/70* (2018.01); *G16H 50/80* (2018.01); *H04B 17/318* (2015.01); *H04W 4/021* (2013.01); *A61B 5/024* (2013.01); *A61B 5/026* (2013.01); *A61B 5/14551* (2013.01); *A61B 2562/0271* (2013.01); *G06F 3/04842* (2013.01)

(56) References Cited

U.S. PATENT DOCUMENTS

| | | |
|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Ai-Ali |
| 6,788,965 B2 | 9/2004 | Ruchti et al. |
| 6,816,241 B2 | 11/2004 | Grubisic |

(56) References Cited

U.S. PATENT DOCUMENTS

| | | |
|---|---|---|
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Ai-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,904,133 B2 | 3/2011 | Gehman et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,290,574 B2 | 10/2012 | Feild et al. |
| 8,315,683 B2 | 11/2012 | Al-Ali et al. |
| 8,315,687 B2 | 11/2012 | Cross et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| D684,071 S | 6/2013 | Greenwood et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,639,319 B2 | 1/2014 | Hugh et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,716,629 B2 | 5/2014 | Klewer et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |

(56) References Cited

U.S. PATENT DOCUMENTS

| | | |
|---|---|---|
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,028,405 B2 | 5/2015 | Tran |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,459,089 B2 | 10/2016 | Ganton et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| D796,363 S | 9/2017 | Ross et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,870,533 B2 | 1/2018 | Ross |
| 9,877,650 B2 | 1/2018 | Muhsin et al. |
| 9,891,079 B2 | 2/2018 | Dalvi |
| 9,907,473 B2 | 3/2018 | Tran |
| 9,924,897 B1 | 3/2018 | Abdul-Hafiz |
| 9,936,917 B2 | 4/2018 | Poeze et al. |
| D817,784 S | 5/2018 | Swenson et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,362,002 B2 | 7/2019 | Ross et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,506,953 B2 | 12/2019 | Ross et al. |
| 10,524,726 B2 | 1/2020 | Wang et al. |
| 10,524,738 B2 | 1/2020 | Olsen |
| 10,532,174 B2 | 1/2020 | Ai-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,743,091 B1 | 8/2020 | Wang et al. |
| 10,750,984 B2 | 8/2020 | Pauley et al. |
| D897,098 S | 9/2020 | Al-Ali |
| 10,758,164 B2 | 9/2020 | Derkx |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |

(56) References Cited

U.S. PATENT DOCUMENTS

| | | |
|---|---|---|
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,172,909 B2 | 11/2021 | Chan et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,492 S | 5/2022 | Wang et al. |
| D950,495 S | 5/2022 | Wang et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,484,265 B2 | 11/2022 | Wang et al. |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0204130 A1 | 10/2003 | Colston et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |

(56) References Cited

U.S. PATENT DOCUMENTS

| | | |
|---|---|---|
| 2009/0076840 A1* | 3/2009 | Boyden ............... G16H 40/67 705/2 |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0318027 A1* | 11/2013 | Almogy ............... G16H 50/20 706/52 |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0132652 A1* | 5/2016 | Chapman Bates .... G16H 50/20 706/11 |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024531 A1 | 1/2017 | Malaviya |
| 2017/0024748 A1 | 1/2017 | Haider |
| 2017/0173632 A1 | 6/2017 | Al-Ali |
| 2017/0235369 A1 | 8/2017 | Acer et al. |
| 2017/0251974 A1 | 9/2017 | Shreim et al. |
| 2017/0311891 A1 | 11/2017 | Kiani et al. |
| 2017/0352119 A1 | 12/2017 | Pittman et al. |
| 2017/0372026 A1* | 12/2017 | Sanyal ............... A61B 5/681 |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374713 A1 | 12/2019 | Kiani et al. |
| 2020/0060869 A1 | 2/2020 | Telfort et al. |
| 2020/0069281 A1 | 3/2020 | Chan et al. |
| 2020/0086133 A1 | 3/2020 | Wang et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0146621 A1 | 5/2020 | Wang et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0383639 A1 | 12/2020 | Wang et al. |
| 2021/0022628 A1 | 1/2021 | Telfort et al. |
| 2021/0058736 A1* | 2/2021 | Ghazzaoui ............... H04W 4/80 |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0071588 A1 | 3/2022 | Chan et al. |
| 2022/0096603 A1 | 3/2022 | Kiani et al. |
| 2022/0117520 A1 | 4/2022 | Wang et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2022/0401037 A1 | 12/2022 | Sadeghzadeh et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |

(56) References Cited

U.S. PATENT DOCUMENTS

| | | |
|---|---|---|
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |

FOREIGN PATENT DOCUMENTS

| | | |
|---|---|---|
| WO | WO 2017/216056 | 12/2017 |
| WO | WO 2021/188999 | 9/2021 |
| WO | WO 2022/087017 | 4/2022 |

OTHER PUBLICATIONS

International Search Report and Written Opinion in PCT Application No. PCT/US2021/023323, as mailed Sep. 15, 2021 in 17 pages.

Kwok et al., "Epidemic Models of Contact Tracing: Systematic Review of Transmission Studies of Severe Acute Respiratory Syndrome and Middle East Respiratory Syndrome", Computational and Structural Biotechnology Journal, 2019, vol. 17, pp. 186-194.

\* cited by examiner

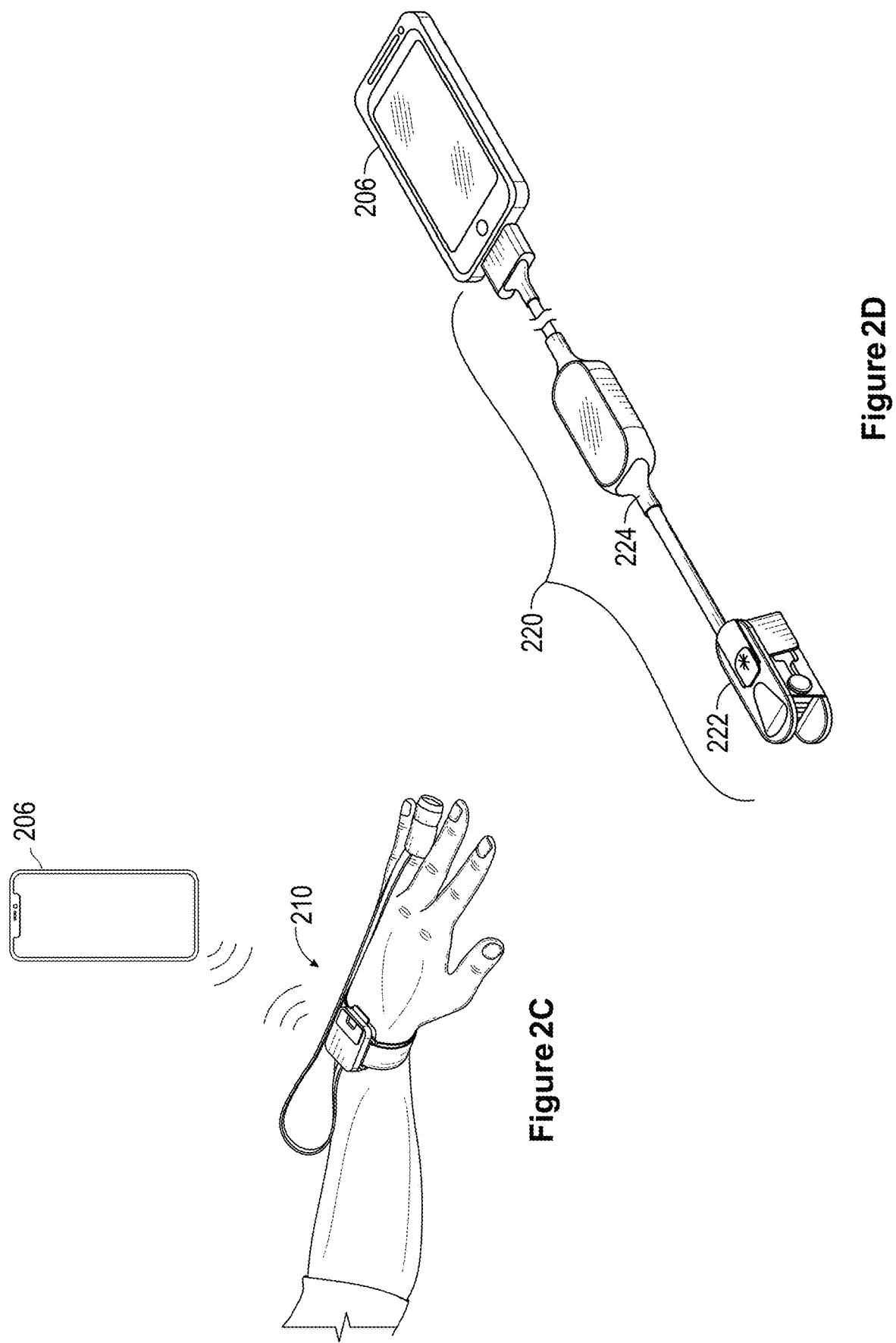

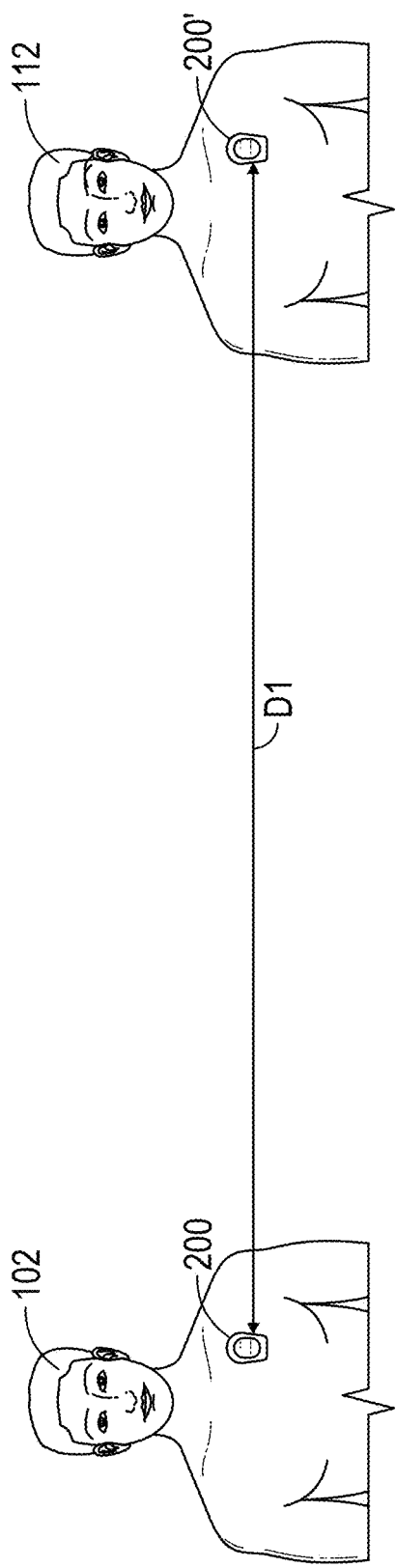
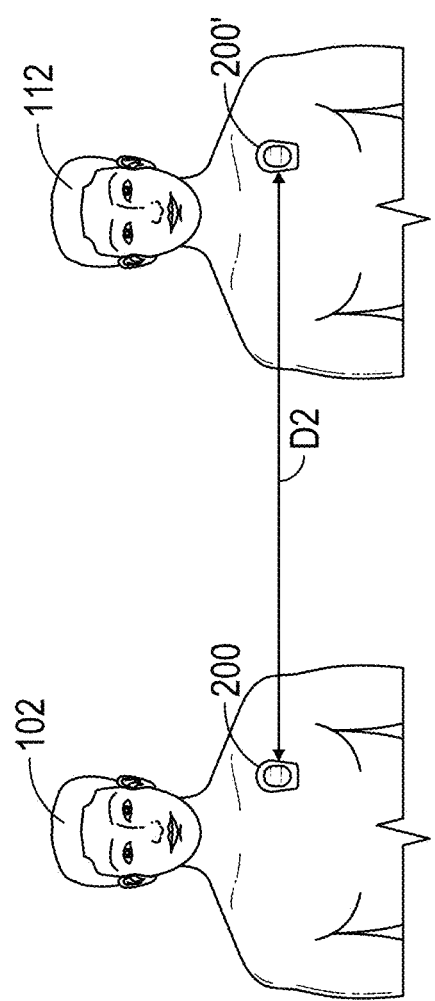
Figure 3A
Figure 3B

| Timestamp | Subject ID | Risk | Distance | Proximity Level | Disease State | Quarantine State |
|---|---|---|---|---|---|---|
| 57 | 7 | 1 | 12.0416 | 2 | 0 | 0 |
| 57 | 15 | 1 | 11.6619 | 2 | 0 | 0 |
| 58 | 7 | 1 | 12 | 2 | 0 | 0 |
| 58 | 42 | 1 | 12.2066 | 2 | 0 | 0 |
| 59 | 7 | 1 | 12.0416 | 2 | 0 | 0 |
| 60 | 7 | 1 | 12.1655 | 2 | 0 | 0 |
| 61 | 7 | 1 | 12.3693 | 2 | 0 | 0 |
| 69 | 100 | 4 | 12.3693 | 2 | 1 | 1 |
| 70 | 100 | 4 | 10.4403 | 2 | 1 | 1 |
| 71 | 100 | 4 | 8.544 | 2 | 1 | 1 |
| 72 | 100 | 4 | 6.7082 | 2 | 1 | 1 |
| 73 | 100 | 4 | 5 | 3 | 1 | 1 |
| 74 | 100 | 4 | 4.2426 | 3 | 1 | 1 |
| 75 | 100 | 4 | 3.6056 | 3 | 1 | 1 |
| 76 | 100 | 4 | 3.1623 | 3 | 1 | 1 |
| 77 | 100 | 4 | 2 | 3 | 1 | 1 |
| 78 | 100 | 4 | 1.4142 | 3 | 1 | 1 |
| 79 | 100 | 4 | 2 | 3 | 1 | 1 |
| 80 | 100 | 4 | 3.1623 | 3 | 1 | 1 |

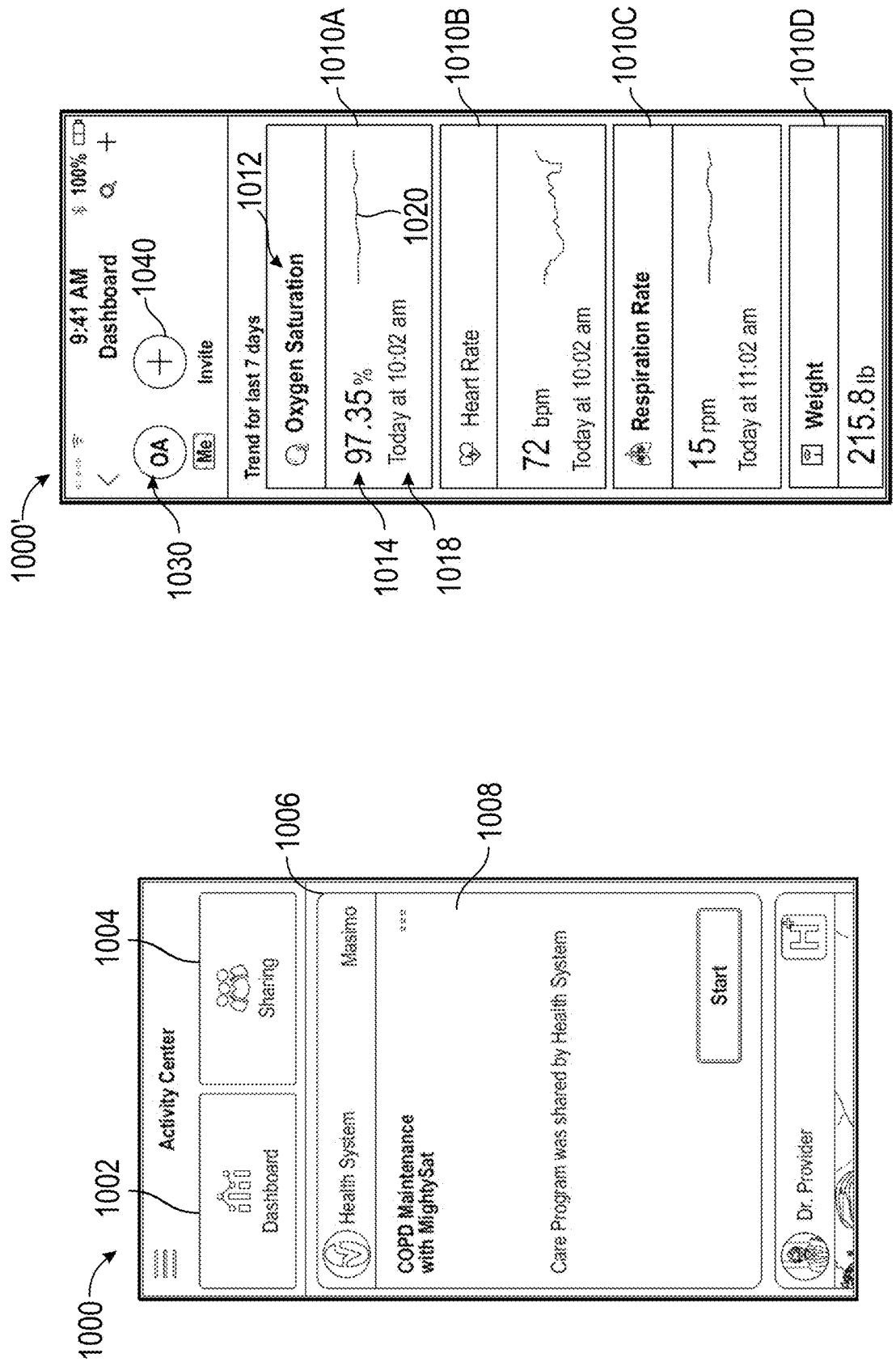

Figure 11C

Update Status

Health Status
Symptomatic

Symptoms Starting Date
Nov 16, 2021

Symptoms (2/10)
- ■ Fever (Over 100.4°F or 38°C)
- ☐ Chills
- ■ Cough
- ☐ Sore Throat
- ☐ Fatigue
- ☐ Shortness of Breath
- ☐ Vomiting
- ☐ Diarrhea
- ☐ Loss of Taste / Smell
- ☐ Other Symptoms

Notes
She is asked to go home for self quarantine.

CANCEL    SUBMIT

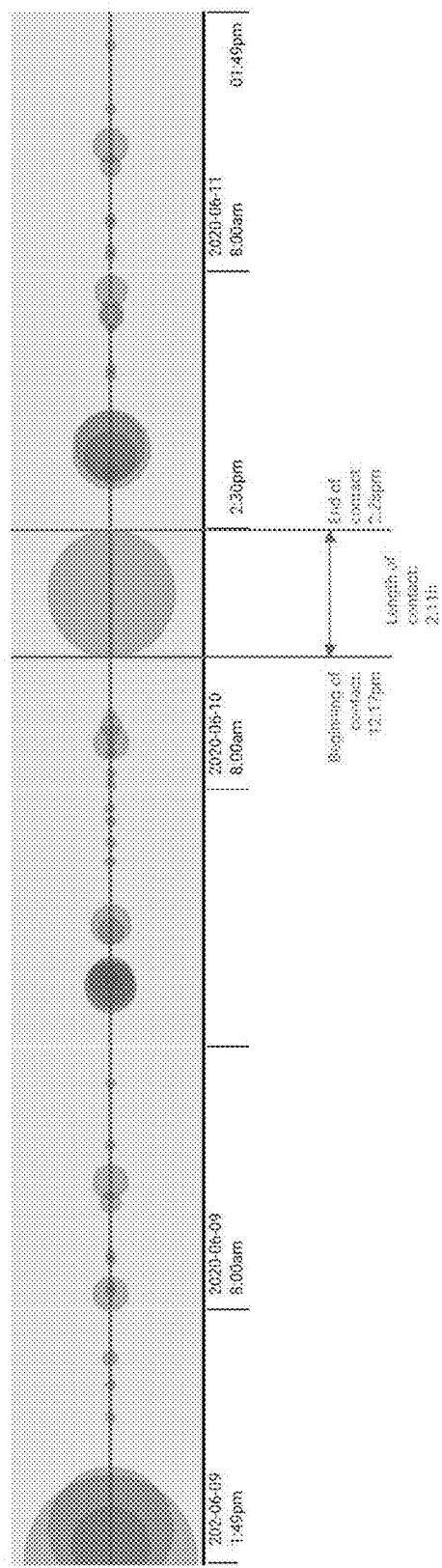
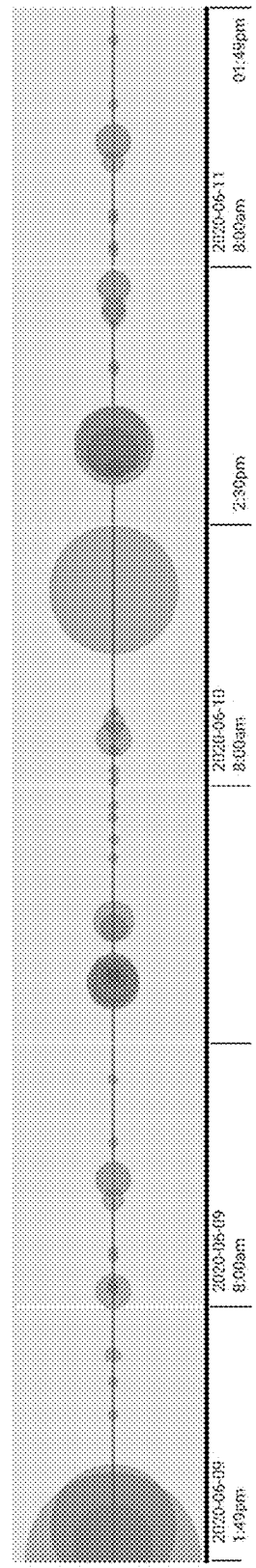
Figure 14A
Figure 14B

WEARABLE DEVICE FOR MONITORING HEALTH STATUS

INCORPORATION BY REFERENCE TO ANY PRIORITY APPLICATIONS

This application claims the benefit of priority under 35 U.S.C. § 119(e) to U.S. Patent Application No. 63/065,961, entitled "HEALTH SCREENING AND MONITORING SYSTEM," filed Aug. 14, 2020, U.S. Patent Application No. 63/106,273, entitled "WEARABLE DEVICE FOR NON-INVASIVE BODY TEMPERATURE MEASUREMENT," filed Oct. 27, 2020, U.S. Patent Application No. 63/056,925, entitled "WEARABLE DEVICE FOR NONINVASIVE BODY TEMPERATURE MEASUREMENT," filed Jul. 27, 2020, U.S. Patent Application No. 63/049,478, entitled "REMOTE PATIENT MANAGEMENT AND MONITORING SYSTEMS AND METHODS," filed Jul. 8, 2020, U.S. Patent Application No. 62/992,808, entitled "REMOTE PATIENT MANAGEMENT AND MONITORING," filed Mar. 20, 2020, U.S. Patent Application No. 62/992,779, entitled "OPIOID OVERDOSE MONITORING USER INTERFACE," filed Mar. 20, 2020, and U.S. Patent Application No. 63/010,669, entitled "REMOTE PATIENT MANAGEMENT AND MONITORING," filed Apr. 15, 2020. All of the above-mentioned applications are hereby incorporated by reference herein in their entireties. Any and all applications for which a foreign or domestic priority claim is identified in the Application Data Sheet as filed with the present application are hereby incorporated by reference under 37 CFR 1.57.

FIELD

This application relates broadly to remote health screening and/or monitoring systems, devices, and methods that can assist employers, schools, hospitals, and other interested parties monitor one or more user's health and risk of having an infectious disease.

BACKGROUND

The COVID-19 pandemic has re-instilled the need across the globe for remote-based monitoring and health screening. There is an increased need to provide remote monitoring and health screening via a secure remote solution to limit exposure to an infection (e.g., virus), especially in organizations such as offices, schools, and medical facilities.

SUMMARY

The COVID-19 pandemic has raised awareness of the potential transmission and contraction risks of a large number of people gathering, especially in an enclosed location. In response to these risks, some businesses have started screening both employees and customers. For example, an employer may require their employees answer a symptoms questionnaire and/or have their temperature taken before entering an office associated with the employer. However, this type of screening may be ineffective or impractical for an organization (e.g., factory) that needs to clear hundreds to thousands of employees in relatively short periods of time (e.g., every shift). Many organizations need to be able to efficiently and reliably conduct mass screenings of their employees to limit the spread of an infectious disease (e.g., virus or bacterial), such as COVID-19, among others (e.g., seasonal flu). This type of mass screening can enable companies to keep their employees safe and give the employees confidence that they will not be infected by their co-workers nor will they infect their co-workers.

Various systems, devices, and methods are disclosed which enable an organization, or a user thereof, to monitor and/or manage health statuses of users associated with the organization in order to limit the spread of an infectious disease or otherwise protect the health of such users. For example, certain aspects of this disclosure describe systems, methods, and devices that can be utilized by an employer to monitor and/or manage health statuses of one or more (or a plurality of) employees and/or other parties (e.g., third party contractors) who may visit or otherwise come into contact with the employer, its facilities, and/or its employees.

Certain aspects of this disclosure describe wearable devices that can monitor and/or measure one or more physiological parameters of a user and communicate (e.g., wirelessly transmit) such physiological parameters to computing devices that may be separate from such wearable devices (e.g., mobile phones, laptops, tablets, etc.). The disclosed wearable devices can measure and/or monitor a variety of physiological parameters which can provide an indication of a user's health status and/or be indicative of symptoms that may be associated with an infection. The disclosed wearable devices can measure and/or monitor various physiological parameters continuously and/or intermittently and can transmit determined physiological parameters to a separate computing device of the user.

As discussed elsewhere herein, some aspects of the present disclosure describe wearable devices that can detect proximity to other, separate wearable devices which may be associated with other users, thereby enabling, in turn, determinations of proximity between various users, for example, in an organization, over one or more time periods. Various systems, devices, and methods are disclosed which enable a computing device (e.g., a mobile computing device such as a smart phone) to receive one or more physiological parameters associated with a user from one or more wearable devices coupled with the user and/or receive proximity data indicative of the user's proximity to one or more other users, for example, over a given time period (e.g., 3 days, 5 days, 7 days, 10 days, 14 days, etc.).

In some aspects, the present disclosure describes computing devices (for example, mobile phones) that can receive one or more physiological parameters from one or more wearable devices associated with a user, proximity data indicative of the user's proximity to one or more other users over a given time period, one or more identifiers associated with the user and/or each of the one or more other users, and/or other information. Advantageously, in some implementations, such computing device can act as a hub (for example, a network and/or communication point) and can transmit information received from the one or more wearable devices to a remote monitoring system (for example, over a network), which can be located at, accessible by, and/or otherwise associated with an organization and/or a monitor user who is tasked with monitoring and/or taking action with respect to the remote monitoring system. Such organization can be, for example, a company, a school, a hospital, a sports or concert venue, etc. The remote monitoring system can receive information from such computing device associated with a user along with similar information from a plurality of other computing devices associated with a plurality of other users (for example, users associated with the organization) and can monitor such information for the purpose of limiting transmission and/or contraction of one or more infections. As discussed herein, such remote monitoring system can be utilized and/or monitored by a "monitor user" associated with an organization. Advantageously, the remote monitoring system can allow an organization to not only monitor health statuses and/or contact tracing information regarding users, but also provide instructions (automatically and/or manually) and/or information (e.g., exposure levels, risk states, etc.) to such users via associated computing devices. Accordingly, the remote monitoring system can allow an organization to dynamically and simultaneously monitor and manage health statuses of its employees to limit the spread of various infections, and relatedly, allow the organization to safely carry out its purpose (e.g., conduct business, manufacture products, care for patients, provide educational services, provide services, etc.).

A system for remotely monitoring and managing health statuses of a plurality of users of an organization to limit a spread of an infection can comprise software instructions storable on a memory device usable by a computing device. The software instructions can cause a hardware processor of the computing device to receive a plurality of sets of health-related information from a plurality of computing devices of a plurality of users, each of said plurality of sets of health-related information comprising: physiological information associated with one of the plurality of users, said physiological information indicative of one or more symptoms experienced by the one of the plurality of users and associated with an infection, said physiological information comprising at least one or more body temperature values; and contact tracing data comprising information indicative of proximity of the one of the plurality of users to at least one other one of the plurality of users. The software instructions can further cause a hardware processor of the computing device to: determine an exposure level for the one of the plurality of users based on at least said contact tracing data; determine a risk state of the one of the plurality of users based on at least said physiological information and said exposure level, said risk state associated with a likelihood that said one of the plurality of users has said infection; and transmit, to one of the computing devices of the one of the plurality of users, at least one of said risk state and an instruction associated with said risk state.

In some aspects of the disclosure, said physiological information can be derived from at least one wearable device coupled to the one of the plurality of users. In some aspects, said physiological information can further comprise at least one of: one or more oxygen saturation values; one or more pulse rate values; and one or more respiration rate values.

In some aspects, said contact tracing data can comprise information indicative of: physical proximity of the one of the plurality of users to said at least one other one of the plurality of users, said physical proximity can be determined based on a detected wireless signal strength between a first wearable device of the one of the plurality of users and a second wearable device of the at least one other one of the plurality of users when the first and second wearable devices are worn. In some aspects, said physical proximity can be determined based on a detected Bluetooth® signal strength between the first and second wearable devices. In some aspects, said software instructions can further cause said hardware processor of the computing device to determine an accumulated duration, over a first time period, that said physical proximity between the one of the plurality of users and the at least one other one of the plurality of users is within a threshold proximity. In some aspects, said exposure level can be determined further based on said accumulated duration. In some aspects, said exposure level for the one of the plurality of users can be determined further based on a risk state of said at least one other one of the plurality of users, said risk state of said at least one other one of the plurality of users associated with a likelihood that said at least one other one of the plurality of users had said infection during at least a portion of said first time period. In some aspects, said threshold proximity can be about 6 ft.

In some aspects, each of said plurality of sets of health-related information can further comprise diagnosis or test result data, and said risk state of the one of the plurality of users can be based on said physiological information, said exposure level, and said diagnosis or test result data. In some aspects, said diagnosis or test result data can be indicative of a positive or negative test result to the infection.

In some aspects, the computing device can be operated by a monitor user associated with the organization. In some aspects, said one of the computing devices of said one of the plurality of users can comprise a smartphone.

In some aspects, said software instructions can further cause said hardware processor of the computing device to determine: an accumulated duration, over a first time period, that said physical proximity between said one of the plurality of users and each other one of the plurality of users confirmed to have said infection is within a threshold proximity; and said exposure level for the one of the plurality of users based on a summation of all of said accumulated durations. In some aspects, said exposure level can be determined based on at least one of an average of said summation of all of said accumulated durations and a maximum of said summation of all of said accumulated durations.

A wearable device for monitoring risk of spreading a contagious infection in an organization can comprise: a temperature sensor configured to generate one or more signals responsive to a thermal energy of a first user; a wireless transceiver configured to communicate with a mobile computing device of the first user; and a processor. The processor can be configured to: receive said one or more signals generated by the temperature sensor and determine one or more body temperature values of the first user; and instruct the wireless transceiver to transmit, to the mobile computing device, said one or more body temperature values; determine one or more proximity values indicative of distance between the wearable device and a separate wearable device that is coupled to a second user. The processor can be further configured to, when said wearable device and said separate wearable device are within a threshold proximity, instruct the wireless transceiver to transmit to the mobile computing device: a first identifier associated with the second user; and said one or more proximity values, said mobile computing device configured to wirelessly transmit said first identifier, a second identifier associated with the first user, said one or more proximity values, and said one or more body temperature values to a remote monitoring system for determination of at least one of an exposure level and risk state of the first user, said risk state associated with a likelihood that said first user has an infection.

In some aspects of the disclosure, the wearable device does not include any other physiological sensors. In some aspects, the wearable device can further comprise a housing configured to at least partially enclose the temperature sensor, wireless transceiver, and processor. In some aspects, the wearable device can further comprise one or more substrates configured to secure the wearable device to skin of the first user.

In some aspects, the processor can be configured to determine said one or more proximity values when the wearable device and the separate wearable device are within a threshold proximity to one another. In some aspects, said threshold proximity can comprise about 20 ft. In some aspects, the processor can be configured to determine said one or more proximity values based on a detected wireless signal strength between said wearable device and said separate wearable device. In some aspects, the processor can be configured to instruct the wireless transceiver to transmit, to the mobile computing device, said first identifier and said one or more proximity values only when said wearable device and said separate wearable device are within said threshold proximity, and the processor can be configured to instruct the wireless transceiver to transmit, to the mobile computing device, said one or more body temperature values continuously at a first time interval regardless of whether said wearable device and said separate wearable device are within said threshold proximity. In some aspects, said first time interval can comprise every minute.

In some aspects, the wearable device can further comprise a battery, and the wearable device does not include any other physiological sensors, thereby maximizing a life of the battery.

A system can comprise the wearable device of any one of the preceding paragraphs and said mobile computing device. In some aspects, said wireless transceiver of said wearable device can be configured to transmit said one or more body temperature values, said first identifier, said second identifier, and said one or more proximity values to said mobile computing device via a first wireless communication protocol, and said mobile computing device can be configured to wirelessly transmit said first identifier, said second identifier, said one or more proximity values, and said one or more body temperature values to said remote monitoring system via a second wireless communication protocol that can be different than said first wireless communication protocol.

A method for remotely monitoring and managing a health status of a user to limit a spread of an infection at an organization can comprise providing a wearable device configured to measure one or more physiological parameters of a first user indicative of an onset of symptoms experienced by the first user and associated with an infection, said wearable device configured to: determine one or more proximity values indicative of distance between the wearable device and a separate wearable device that is configured to measure one or more physiological parameters of a second user indicative of an onset of symptoms experienced by the second user and associated with said infection, said one or more proximity values determined based on detected wireless signal strength between the wearable device of the first user and the separate wearable device of the second user. The method can further comprise providing a mobile software application configured for execution by one or more hardware processors of a mobile computing device configured for wireless communication with said wearable device, the mobile software application configured to execute commands to enable the mobile computing device to: wirelessly receive, from the wearable device, said one or more physiological parameters of the first user; wirelessly receive, from the wearable device when said wearable device and said separate wearable device are within a threshold proximity to one another, a first identifier associated with the first user of the wearable device, a second identifier associated with the second user of the separate wearable device, and said one or more proximity values; wirelessly transmit, to a remote monitoring system, said one or more physiological parameters of the first user, said first identifier, said second identifier, and said determined one or more proximity values; wirelessly receive, from the remote monitoring system, a risk state of the first user, the risk state associated with a likelihood that said first user has said infection; generate a graphical user interface on a display of the mobile computing device; and display, in at least a portion of the graphical user interface, at least one of said risk state and an instruction associated with said risk state.

In some aspects of the disclosure, said one or more physiological parameters can comprise one or more body temperature values of the first user, and said mobile software application can be configured to execute commands to enable the mobile computing device to wirelessly receive, from the wearable device, said one or more body temperature values at a first time interval. In some aspects, said mobile software application can be configured to execute commands to enable the mobile computing device to wirelessly transmit said one or more body temperature values of said first user, said first identifier, said second identifier, and said determined one or more proximity values at said first time interval. In some aspects, said first time interval can comprise every minute.

In some aspects, said one or more proximity values can be determined based on detected Bluetooth® signal strength between the wearable device of the first user and the separate wearable device of the second user.

In some aspects, said mobile software application can be configured to execute commands to enable the mobile computing device to wirelessly receive, from the remote monitoring system, information indicative of exposure of the first user to said infection. In some aspects, said mobile software application can be configured to execute commands to enable the mobile computing device to display, in at least a portion of the graphical user interface, at least one of said information indicative of said exposure and an instruction related to said information indicative of said exposure.

In some aspects, said mobile software application can be configured to execute commands to enable the mobile computing device to wirelessly transmit, to the remote monitoring system, information indicative of a test result of the first user associated with said infection and inputted by the first user via the mobile software application. In some aspects, said mobile software application can be configured to execute commands to enable the mobile computing device to wirelessly transmit, to the remote monitoring system, information indicative of one or more symptoms of the first user associated with said infection and inputted by the first user via the mobile software application. In some aspects, said wearable device can be configured to detect only one type of physiological parameter of the first user, said one type of physiological parameter being body temperature. In some aspects, said threshold proximity can be about 30 ft.

In some aspects, the wearable device can be configured to wirelessly transmit said one or more proximity values to the mobile computing device at a first time interval and the mobile software application can be configured to execute commands to enable the mobile computing device to wirelessly transmit said determined one or more proximity values over a second time interval. In some aspects, said first time interval can be different than said second time interval. In some aspects, said first time interval can be the same as said second time interval.

A method for remotely notifying a user of exposure to an infection can comprise providing a wearable device configured to couple to a first user, said wearable device can further be configured to: determine proximity of the wearable device to a separate wearable device that is configured to measure one or more physiological parameters of a second user indicative of an onset of symptoms experienced by the second user and associated with an infection, said proximity determined based on a detected wireless signal strength between the wearable device of the first user and the separate wearable device of the second user. The method can further comprise providing a mobile software application configured for execution by one or more hardware processors of a mobile computing device configured for wireless communication with said wearable device. The mobile software application can be configured to execute commands to enable the mobile computing device to: wirelessly receive, from the wearable device when said proximity is within a first threshold, a first identifier associated with the first user of the wearable device and a second identifier associated with the second user of the separate wearable device; wirelessly transmit said first identifier and said second identifier to a remote monitoring system when said proximity is within the first threshold; wirelessly receive, from the remote monitoring system, a notification configured to alert the first user of at least one of an exposure of the first user to said infection and a risk state of the first user, said risk state associated with a likelihood that said first user has said infection; generate a graphical user interface on a display of the mobile computing device; and display, in at least a portion of the graphical user interface, at least one of said notification received from said remote monitoring system and a visual representation associated with said notification.

In some aspects of the disclosure, said wearable device can be configured to measure one or more physiological parameters of the first user indicative of an onset of symptoms experienced by the first user and associated with the infection. In some aspects, said mobile software application can further be configured to execute commands to enable the mobile computing device to: wirelessly receive, from the wearable device, said one or more physiological parameters of the first user from said wearable device; and wirelessly transmit, to a remote monitoring system, said one or more physiological parameters of the first user. In some aspects, said one or more physiological parameters of the first user can comprise one or more body temperature values. In some aspects, said one or more physiological parameters can comprise only one type of physiological parameter, said one type of physiological parameter being body temperature.

In some aspects, said wearable device can further be configured to determine: one or more proximity values indicative of distance between the wearable device and the separate wearable device when the wearable device and the separate wearable device are within the first threshold from one another; and wirelessly transmit said one or more proximity values to said mobile computing device when the wearable device and the separate wearable device are within the first threshold from one another. In some aspects, said mobile software application can be further configured to execute commands to enable the mobile computing device to: wirelessly receive said one or more proximity values from said wearable device; and wirelessly transmit said one or more proximity values to said remote monitoring system. In some aspects, said wearable device can be configured to wirelessly transmit said one or more proximity values to said mobile computing device at a first time interval. In some aspects, said first time interval can be every minute. In some aspects, said one or more proximity values can be determined based on detected Bluetooth® signal strength between the wearable device of the first user and the separate wearable device of the second user.

In some aspects, said mobile software application can be configured to execute commands to enable the mobile computing device to wirelessly transmit, to the remote monitoring system, information indicative of a test result of the first user associated with said infection and inputted by the first user via the mobile software application. In some aspects, said mobile software application can be configured to execute commands to enable the mobile computing device to wirelessly transmit, to the remote monitoring system, information indicative of one or more symptoms of the first user associated with said infection and inputted by the first user via the mobile software application. In some aspects, said first threshold can be about 30 ft.

A system can comprise the wearable device and the mobile software application of any one of the preceding paragraphs.

A non-transitory computer medium storing instructions that, when executed by one or more processors of a mobile computing device, can cause the one or more processors to perform operations configured to notify a first user of the mobile computing device of a risk state associated with a likelihood that said first user has one or more infections can comprise: receiving, from a first wearable device, one or more physiological parameters of the first user indicative of an onset of one or more symptoms experienced by the first user and associated with said one or more infections; when said first wearable device is within a threshold proximity to a second wearable device configured to measure one or more physiological parameters of a second user, receiving proximity data from said first wearable device, said proximity data including one or more distance values between said first and second wearable devices over a first time period, said proximity data determined based on a detected wireless signal strength between the first and second wearable devices; receiving, from the first wearable device when said first wearable device is within said threshold proximity to the second wearable device, a first identifier associated with the second user of the second wearable device; transmitting, to a remote monitoring system, said one or more physiological parameters of the user; transmitting, to the remote monitoring system, said first identifier, a second identifier associated with the first user, and said proximity data when said first wearable device is within said threshold proximity to the second wearable device; receiving, from the remote monitoring system, said risk state associated with said likelihood that said first user has said one or more infections; generating a graphical user interface on the mobile computing device; and displaying, on at least a portion of the graphical user interface, at least one of said risk state, a visual or audio representation of said risk state, and an instruction associated with said risk state.

In some aspects of the disclosure, said displaying, on said at least said portion of the graphical user interface comprises displaying said risk state and an instruction associated with said risk state. In some aspects, said displaying, on said at least said portion of the graphical user interface further comprises displaying said visual or audio representation of said risk state. In some aspects, said one or more physiological parameters of the first user comprise one or more body temperature values. In some aspects, said one or more physiological parameters comprise only one type of physiological parameter, said one type of physiological parameter being body temperature.

In some aspects, said receiving said one or more distance values comprises receiving said one or distance values over a first time interval. In some aspects, said first time interval can be every minute.

In some aspects, said proximity data can be determined based on a detected Bluetooth® signal strength between the first and second wearable devices. In some aspects, said operations can further comprise wirelessly transmitting, to the remote monitoring system, information indicative of a test result of the first user associated with said one or more infections and inputted by the first user via the mobile computing device. In some aspects, said operations can further comprise wirelessly transmitting, to the remote monitoring system, information indicative of one or more symptoms of the first user associated with said one or more infections and inputted by the first user via the mobile computing device. In some aspects, said threshold proximity can be about 30 ft. In some aspects, said operations can further comprise: receiving said one or more physiological parameters, said proximity data, and said first identifier from the first wearable device over a first wireless communication protocol; and transmitting said first identifier, said second identifier, said one or more physiological parameters, and said proximity data to the remote monitoring system over a second wireless communication protocol, said second wireless communication protocol being different than said first wireless communication protocol.

A wearable device for monitoring a user's health status can comprise: at least one physiological sensor configured to measure one or more physiological parameters of a first user, said at least one physiological sensor comprising a temperature sensor configured to generate one or more signals responsive to a thermal energy of the first user; a first wireless transceiver configured to communicate with a mobile computing device of the first user; and a processor. The processor can be configured to: receive said one or more signals generated by the temperature sensor and determine one or more body temperature values of the first user based on said received one or more signals; instruct the first wireless transceiver to transmit to the mobile computing device, at a first time interval, said determined one or more body temperature values; and determine one or more proximity values indicative of distance between the first wireless transceiver and a second wireless transceiver of a separate wearable device that is coupled to a second user when said first and second wireless transceivers are within a threshold proximity to one another, said one or more proximity values can be determined based on a detected wireless signal strength between the first and second wireless transceivers. The processor can be further configured to, when said first and second wireless transceivers are within said threshold proximity based on said detected wireless signal strength, instruct the first wireless transceiver to transmit to the mobile computing device at a second time interval: a first identifier associated with the second user; and said one or more proximity values, said mobile computing device configured to wirelessly transmit said first identifier, a second identifier associated with the first user, said one or more body temperature values, and said one or more proximity values to a remote monitoring system for determination of a risk state of the first user, said risk state associated with a likelihood that said first user has one or more infections.

In some aspects of the disclosure, the wearable device can be configured to determine only one type of physiological parameter of the first user, said type of physiological parameter being temperature of the first user. In some aspects, the wearable device can further comprise one or more substrates configured to secure the wearable device to skin of the first user. In some aspects, said threshold proximity can comprise about 20 ft. In some aspects, said threshold proximity can comprise about 30 ft.

In some aspects, the processor can be configured to instruct the first wireless transceiver to transmit, to the mobile computing device, said first identifier and said one or more proximity values only when said first and second wireless transceivers are within said threshold proximity, and the processor can be configured to instruct the first wireless transceiver to transmit, to the mobile computing device, said one or more body temperature values continuously at said first time interval regardless of whether said first and second wireless transceivers are within said threshold proximity. In some aspects, said first time interval can comprise every minute.

In some aspects, the wearable device can further comprise a battery. In some aspects, the wearable device can further comprise a housing configured to be coupled to the first user. In some aspects, said one or more proximity values can be determined based on a detected Bluetooth® signal strength between the first and second wireless transceivers.

A system can comprise the wearable device of any one of the preceding paragraphs and said mobile computing device.

A system can comprise the wearable device of the preceding paragraphs and a mobile software application configured for execution by one or more hardware processors of the mobile computing device. The mobile software application can be configured to execute commands to enable the mobile computing device to: wirelessly receive said one or more body temperature values, said first identifier, and said one or more proximity values; and wirelessly transmit said one or more body temperature values, said first identifier, said second identifier, and said one or more proximity values to said remote monitoring system for determination of said risk state. In some aspects, the mobile software application can be further configured to execute commands to enable the mobile computing device to: wirelessly receive, from the remote monitoring system, said risk state of the first user; generate a graphical user interface on a display of the mobile computing device; and display, in at least a portion of the graphical user interface, at least one of said risk state and an instruction associated with said risk state.

In some aspects, each of the first and second time intervals can comprise one minute. In some aspects, the first and second time intervals can be the same. In some aspects, the first and second time intervals can be different.

A wearable device for monitoring a user's health status can comprise: at least one physiological sensor configured to measure one or more physiological parameters of a first user; a first wireless transceiver configured to communicate with a mobile computing device of the first user; and a processor. The processor can be configured to: instruct the first wireless transceiver to transmit to the mobile computing device said one or more physiological parameters measured by said at least one physiological sensor; determine one or more proximity values indicative of distance between the first wireless transceiver and a second wireless transceiver of a separate wearable device that is coupled to a second user when said first and second wireless transceivers are within a threshold proximity; when said first and second wireless transceivers are within said threshold proximity, instruct the first wireless transceiver to transmit to the mobile computing device a first identifier associated with the second user, and said one or more proximity values.

In some aspects of the disclosure, said at least one physiological sensor can comprise a temperature sensor configured to generate one or more signals responsive to a thermal energy of the first user, and said processor can be further configured to: receive said one or more signals generated by the temperature sensor and determine one or more body temperature values of the first user based on said received one or more signals; instruct the first wireless transceiver to transmit said determined one or more body temperature values to the mobile computing device at a first time interval; and determine one or more proximity values based on a detected wireless signal strength between the first and second wireless transceivers. In some aspects, mobile computing device can be configured to wirelessly transmit said first identifier, said second identifier, said one or more body temperature values, and said one or more proximity values to a remote monitoring system for determination of a risk state of the first user, said risk state associated with a likelihood that said first user has one or more infections.

A system can comprise the wearable device of any one of the preceding paragraphs and a mobile software application configured for execution by one or more hardware processors of the mobile computing device. The mobile software application can be configured to execute commands to enable the mobile computing device to: wirelessly receive said one or more body temperature values, said first identifier, and said one or more proximity values; and wirelessly transmit said one or more body temperature values, said first identifier, said second identifier, and said one or more proximity values to said remote monitoring system for determination of said risk state. In some aspects, the mobile software application can be further configured to execute commands to enable the mobile computing device to: wirelessly receive, from the remote monitoring system, said risk state of the first user; generate a graphical user interface on a display of the mobile computing device; and display, in at least a portion of the graphical user interface, at least one of said risk state and an instruction associated with said risk state. In some aspects, said one or more proximity values can be determined based on a detected Bluetooth® signal strength between the first and second wireless transceivers. In some aspects, the processor can be configured to instruct the first wireless transceiver to transmit, to the mobile computing device, said first identifier and said one or more proximity values only when said first and second wireless transceivers are within said threshold proximity, and the processor can be configured to instruct the first wireless transceiver to transmit, to the mobile computing device, said one or more body temperature values continuously at said first time interval regardless of whether said first and second wireless transceivers are within said threshold proximity. In some aspects, said first time interval can comprise every minute.

A system can comprise the wearable device of any one of the preceding paragraphs and said mobile computing device. In some aspects, the wearable device can be configured to determine only one type of physiological parameter of the first user, said type of physiological parameter being temperature of the first user.

In some aspects, the wearable device can further comprise a housing configured to be coupled to the first user. In some aspects, the wearable device can further comprise one or more substrates configured to secure the wearable device to skin of the first user.

In some aspects, the wearable device can further comprise a battery. In some aspects, said threshold proximity can comprise about 30 ft. In some aspects, said threshold proximity can comprise about 20 ft.

A system for remotely monitoring and managing health statuses of a plurality of users can comprise software instructions storable on a memory device usable by a computing device configured to be operated by a monitor user. The software instructions can cause one or more hardware processors of the computing device to receive a plurality of sets of health-related information from a plurality of mobile computing devices of a plurality of users, said plurality of sets of health-related information comprising a first set of health-related information associated with a first one of the plurality of users. The first set of health-related information can comprise: physiological information derived from at least one wearable device when attached to the first one of the plurality of users, said physiological information indicative of an onset of symptoms experienced by the first one of the plurality of users and associated with one or more infections, said physiological information comprising at least a body temperature of the first one of the plurality of users; contact tracing data comprising information indicative of proximity of the first one of the plurality of users to a second one of the plurality of users, said proximity determined based on a detected wireless signal strength between a first wearable device of the first one of the plurality of users and a second wearable device of the second one of the plurality of users when the first and second wearable devices are worn by the first and second users; and diagnosis or test result data associated with the first one of the plurality of users and indicative of a positive or negative result to at least one of said one or more infections. The software instructions can further cause one or more hardware processors of the computing device to: determine an accumulated duration, over a first time period, that said proximity between the first and second ones of the plurality of users is within a threshold proximity; determine an exposure level for the first one of the plurality of users based on said contact tracing data, said accumulated duration, and a risk state of the second one of the plurality of users associated with a likelihood that said second one of the plurality of users had said one or more infections during at least a portion of said first time period; determine a risk state of the first one of the plurality of users based on at least said physiological information, said diagnosis or test result data, and said exposure level, said risk state of the first one of the plurality of users associated with a likelihood that said first one of the plurality of users has said one or more infections; and wirelessly transmit, to a first mobile computing device of the first one of the plurality of users, at least one of said risk state and an instruction associated with said risk state, said first mobile computing device configured to indicate on a display of said first mobile computing device at least one of said at least one of said risk state and said instruction, and a representation of said at least one of said risk state and said instruction.

In some aspects of the disclosure, said contact tracing data can further comprise information indicative of: proximity of the first one of the plurality of users to a third one of the plurality of users, said proximity determined based on a detected wireless signal strength between the first wearable device of the first one of the plurality of users and a third wearable device of the third one of the plurality of users when the first and third wearable devices are worn by the first and third users. In some aspects, said software instructions can further cause one or more hardware processors of the computing device to: determine an accumulated duration, over a second time period, that said proximity between the first and third ones of the plurality of users is within the threshold proximity; and determine said exposure level for the first one of the plurality of users based on said contact tracing data, said accumulated durations, and a risk state of the third one of the plurality of users associated with a likelihood that said third one of the plurality of users had said one or more infections during at least a portion of said second time period.

In some aspects, said contact tracing data can further comprise information indicative of: proximity of the first one of the plurality of users to at least two other ones of the plurality of users, said proximity determined based on detected wireless signal strengths between the first wearable device of the first one of the plurality of users and wearable devices of said at least two other ones of the plurality of users when the first wearable device is worn by the first one of the plurality of users and the wearable devices of said at least two other ones of the plurality of users are worn by the said at least two other ones of the plurality of users. In some aspects, said software instructions can further cause one or more hardware processors of the computing device to: determine an accumulated duration that said proximity between the first and each of the at least two other ones of the plurality of users is within the threshold proximity; and determine said exposure level for the first one of the plurality of users based on said contact tracing data, said accumulated durations, and a risk state of each of the at least two other ones of the plurality of users associated with a likelihood that each of said at least two other ones of the plurality of users had said one or more infections when within said threshold proximity of said first one of the plurality of users.

In some aspects, said risk state of the second one of the plurality of users can be determined by the one or more hardware processors of the computing device based on at least: physiological information associated with the second one of the plurality of users and derived from said second wearable device when attached to the second one of the plurality of users, said physiological information comprising at least a body temperature of the second one of the plurality of users; and an exposure level for the second one of the plurality of users. The exposure level for the second one of the plurality of users can be determined based on at least: contact tracing data associated with said second one of the plurality of users, said contact tracing data associated with said second one of the plurality of users comprising information indicative of proximity of the second one of the plurality of users to at least a third one of the plurality of users, said proximity determined based on a detected wireless signal strength between the second wearable device of the second one of the plurality of users and a third wearable device of the third one of the plurality of users when the second and third wearable devices are worn by the second and third ones of the plurality of users; an accumulated duration, over a second time period, that said physical proximity between the second and third ones of the plurality of users was within the threshold proximity; and a risk state of the third one of the plurality of users associated with a likelihood that said third one of the plurality of users had said one or more infections during at least a portion of said second time period. In some aspects, the first and second time periods can be the same. In some aspects, the first and second time periods can be different.

In some aspects, said plurality of sets of health-related information can further comprise a second set of health-related information associated with a third one of the plurality of users. The second set of health-related information can comprise: physiological information derived from at least one wearable device when attached to the third one of the plurality of users, said physiological information indicative of an onset of symptoms experienced by the third one of the plurality of users and associated with the said one or more infections, said physiological information comprising at least a body temperature of the third one of the plurality of users; contact tracing data associated with said third one of the plurality of users and comprising information indicative of proximity of the third one of the plurality of users to a fourth one of the plurality of users, said proximity determined based on a detected wireless signal strength between a third wearable device of the third one of the plurality of users and a fourth wearable device of the fourth one of the plurality of users when the third and fourth wearable devices are worn by the third and fourth users. The one or more hardware processors of the computing device can be further configured to: determine an accumulated duration, over a second time period, that said proximity between the third and fourth ones of the plurality of users is within the threshold proximity; determine an exposure level for the third one of the plurality of users based on said contact tracing data associated with said third one of the plurality of users, said accumulated duration that said proximity between the third and fourth ones of the plurality of users is within the threshold proximity over the second time period, and a risk state of the fourth one of the plurality of users associated with a likelihood that said fourth one of the plurality of users had said one or more infections during at least a portion of said second time period; and determine a risk state for the third one of the plurality of users. The risk state for the third one of the plurality of users can be determined based on: said physiological information derived from at least one wearable device when attached to the third one of the plurality of users; and said exposure level for the third one of the plurality of users, said risk state of the third one of the plurality of users is associated with a likelihood that said third one of the plurality of users has said one or more infections. In some aspects, the first and second time periods can be the same. In some aspects, the first and second time periods can be different. In some aspects, said one or more hardware processors of the computing device can be further configured to cause the computing device to wirelessly transmit, to a third mobile computing device of the third one of the plurality of users, at least one of: said risk state of the third one of the plurality of users; and an instruction associated with said risk state of the third one of the plurality of users.

In some aspects, said detected wireless signal strength can comprise a detected Bluetooth® signal strength. In some aspects, said determined risk state of the first one of the plurality of users can comprise one of: a confirmation that said first one of the plurality of users has the one of more infections; a confirmation that said first one of the plurality of users does not have the one of more infections; or a confirmation that said first one of the plurality of users is suspected to have the one of more infections and that said first one of the plurality of users is experiencing said symptoms associated with said one or more infections; or a confirmation that said first one of the plurality of users is suspected to have the one of more infections and that said first one of the plurality of users is not experiencing said symptoms associated with said one or more infections. In some aspects, said first set of health-related information can further comprise symptom information of the first one of the plurality of users recorded by the first mobile computing device. In some aspects, said one or more hardware processors of the computing device can be configured to wirelessly receive said plurality of sets of health-related information over a network. In some aspects, said computing device operated by said monitor user can be a desktop computer. In some aspects, said computing device operated by said monitor user can be a mobile phone. In some aspects, said computing device operated by said monitor user can be a tablet. In some aspects, said first mobile computing device can comprise a mobile phone. In some aspects, said first mobile computing device can comprise a smart watch. In some aspects, said threshold proximity can be about 30 ft. In some aspects, said threshold proximity can be about 20 ft.

A system for remotely monitoring and managing health statuses of one or more users can comprise software instructions storable on a memory device usable by a computing device configured to be operated by a monitor user. The software instructions can be configured to cause one or more hardware processors of the computing device to receive a first set of health-related information from a first mobile computing device of a first user, said first set of health-related information comprising: physiological information derived from at least one wearable device when attached to the first user, said physiological information indicative of an onset of one or more symptoms experienced by the first user and associated with one or more infections; and contact tracing data associated with the first user comprising information indicative of proximity of the first user to a second user, said proximity determined based on a detected wireless signal strength between a first wearable device of the first user and a second wearable device of the second user. The software instructions can further cause the one or more hardware processors of the computing device to: determine an accumulated duration, over a first time period, that said proximity between the first and second users is within a threshold proximity; determine an exposure level for the first user based on said contact tracing data, said accumulated duration, and a risk state of the second user associated with a likelihood that said second user had said one or more infections during at least a portion of said first time period; and determine a risk state of the first user based on at least said physiological information and said exposure level, said risk state of the first user associated with a likelihood that said first user has said one or more infections.

In some aspects of the disclosure, said software instructions can further be configured to cause one or more hardware processors of the computing device to: wirelessly transmit, to the first mobile computing device of the first user, at least one of said risk state of the first user and an instruction associated with said risk state of the first user. In some aspects, said first mobile computing device can be configured to indicate on a display of said first mobile computing device at least one of: said risk state of the first user and said instruction; and a representation of said at least one of said risk state of the first user and said instruction.

In some aspects, said first set of health-related information can further comprise diagnosis or test result data indicative of a positive or negative result to at least one of said one or more infections, and said one or more hardware processors can be further configured to determine said risk state of the first user based on said diagnosis or test result data. In some aspects, said first set of health-related information can further comprise symptom information of the first user recorded by the first mobile computing device, and said one or more hardware processors can be further configured to determine said risk state of the first user based on said symptom information.

In some aspects, said risk state of the second user can be determined by said one or more hardware processors based on at least: physiological information associated with the second user and derived from at least one wearable device when attached to the second user. In some aspects, said risk state of the second user can be determined by said one or more hardware processors further based on: an exposure level associated with the second user. In some aspects, said risk state of the second user can be determined by the said one or more hardware processors further based on an exposure level for the second user, said exposure level for the second user determined based on at least contact tracing data associated with said second user, said contact tracing data associated with said second user comprising information indicative of: proximity of the second user to at least a third user, said proximity determined based on a detected wireless signal strength between the second wearable device of the second user and a third wearable device of the third user when the second and third wearable devices are worn by the second and third users; an accumulated duration, over a second time period, that said proximity between the second and third users is within the threshold proximity; and a risk state of the third user associated with a likelihood that said third user had said one or more infections during at least a portion of said second time period.

In some aspects, said physiological information can comprise at least a body temperature of the first user. In some aspects, said first time period can comprise 7 days. In some aspects, said first time period can comprise 14 days. In some aspects, said detected wireless signal strength can comprise a detected Bluetooth® signal strength. In some aspects, said determined risk state of the first user can comprise one of: a confirmation that said first user has the one of more infections; a confirmation that said first user does not have the one of more infections; a confirmation that said first user is suspected to have the one of more infections and that said first user is experiencing said one or more symptoms associated with said one or more infections; and a confirmation that said first user is suspected to have the one of more infections and that said first user is not experiencing said one or more symptoms associated with said one or more infections. In some aspects, said threshold proximity can be about 100 ft. In some aspects, said threshold proximity can be about 30 ft. In some aspects, said threshold proximity can be about 20 ft.

In some aspects, said physiological information can comprise body temperature of the first user. In some aspects, said physiological information can further comprise a heart rate of the first user. In some aspects, said physiological information can further comprise a blood pressure of the first user. In some aspects, said physiological information can further comprise a respiratory rate of the first user. In some aspects, said physiological information can further comprise at least one of total hemoglobin levels, carboxyhemoglobin levels, and methemoglobin levels of the first user. In some aspects, said physiological information can further comprise oxygen saturation of the first user. In some aspects, said physiological information can further comprise at least one of a perfusion index of the first user and a pleth variability index of the first user. In some aspects, said at least one wearable device can comprise the first wearable device and a third wearable device separate from the first wearable device, the first wearable device can be configured to determine body temperature of the first user and the third wearable device can be configured to determine at least one of an oxygen saturation and a pulse rate of the first user.

In some aspects, said proximity can be determined based on a detected Bluetooth® signal strength between the first and second wearable devices.

A system for monitoring and managing a health status of a user can comprise a wearable device configured to couple to a first user comprising: at least one physiological sensor; a wireless transceiver configured to communicate with a mobile computing device of the first user; and a processor. The processor can be configured to: determine one or more physiological parameters of the first user based upon one or more signals received from the at least one physiological sensor, said one or more physiological parameters indicative of an onset of symptoms experienced by the first user and associated with an infection; and instruct the wireless transceiver to transmit to the mobile computing device said determined one or more physiological parameters; determine one or more proximity values indicative of distance between the wearable device and a separate wearable device that is coupled to a second user when said wearable device and said separate wearable device are within a threshold proximity, said one or more proximity values are determined based on a detected wireless signal strength between the wearable device and the separate wearable device. The processor can be further configured to, when said wearable device and said separate wearable device are within said threshold proximity based on said detected wireless signal strength, instruct the wireless transceiver to transmit to the mobile computing device: a first identifier associated with the second user of the separate wearable device; and said one or more proximity values. The system can further comprise a mobile software application configured for execution by one or more hardware processors of the mobile computing device of the first user. The mobile software application can be configured to execute commands to enable the mobile computing device to: wirelessly receive, from the wearable device, said one or more physiological parameters of the first user, said first identifier, a second identifier associated with the first user, and said one or more proximity values when said wearable device and said separate wearable device are within said threshold proximity; wirelessly transmit, to a remote monitoring system, said determined one or more physiological parameters of the first user, said first identifier, said second identifier, and said one or more proximity values; wirelessly receive, from the remote monitoring station, a risk state of the first user, the risk state associated with a likelihood that said first user has said infection; generate a graphical user interface on a display of the mobile computing device; and display, in at least a portion of the graphical user interface, at least one of said risk state and an instruction associated with said risk state.

In some aspects of the disclosure, said at least one physiological sensor can comprise one or more temperature sensors configured to generate one or more signals responsive to thermal energy of the first user, and said processor can be configured to determine one or more body temperature values of the first user based on said one or more signals. In some aspects, said mobile software application can be configured to execute commands to enable the mobile computing device to wirelessly receive, from the wearable device, said one or more body temperature values at a first time interval. In some aspects, said mobile software application can be configured to execute commands to enable the mobile computing device to wirelessly transmit said one or more body temperature values of first user, said first identifier, said second identifier, and said determined one or more proximity values at said first time interval. In some aspects, said first time interval can comprise every minute.

In some aspects, said one or more proximity values can be determined based on detected Bluetooth® signal strength between said wearable device and said separate wearable device.

In some aspects, said mobile software application can be configured to execute commands to enable the mobile computing device to wirelessly receive, from the remote monitoring system, information indicative of exposure of the first user to said infection. In some aspects, said mobile software application can be configured to execute commands to enable the mobile computing device to display, in at least a portion of the graphical user interface, at least one of said information indicative of said exposure and an instruction related to said information indicative of said exposure.

In some aspects, said mobile software application can be configured to execute commands to enable the mobile computing device to wirelessly transmit, to the remote monitoring system, information indicative of a test result of the first user associated with said infection and inputted by the first user via the mobile software application. In some aspects, said mobile software application can be configured to execute commands to enable the mobile computing device to wirelessly transmit, to the remote monitoring system, information indicative of one or more symptoms of the first user associated with said infection and inputted by the first user via the mobile software application. In some aspects, said wearable device can be configured to detect only one type of physiological parameter of the first user, said one type of physiological parameter being body temperature. In some aspects, said threshold proximity can be about 30 ft. In some aspects, said threshold proximity can be about 20 ft. In some aspects, said threshold proximity can be about 10 ft. In some aspects, said threshold proximity can be about 6 ft.

A method for monitoring one or more contact events for a user to limit a spread of an infection can include providing a wearable device and providing a software application configured for execution by one or more hardware processors of a computing device. The wearable device can be configured to couple to a first user and can be further configured to determine proximity data indicative of distance between the wearable device and a separate wearable device that is configured to couple to a second user, said proximity data determined based on detected wireless signal strength between the wearable device of the first user and the separate wearable device of the second user. The software application can be configured to execute commands to enable the computing device to: receive, from the wearable device, a first identifier associated with the first user of the wearable device, a second identifier associated with the second user of the separate wearable device, and said proximity data; store said proximity data over time and determine one or more contact events based on said proximity data, wherein each of said one or more contact events is representative of the first and second users being within a threshold proximity from one another for a continuous period of time; generate a graphical user interface on a display of the computing device; display, in at least a portion of the graphical user interface, a timeline, said timeline being continuously updated over time; and display, in at least a portion of the graphical user interface, a visual representation of each one of said one or more contact events on said timeline.

In some implementations, the visual representation comprises a bubble, wherein a perimeter of said bubble is indicative of said continuous period of time. In some implementations, a first point on said perimeter of said bubble is indicative of a time when each of said one or more contact events begins and a second point on said perimeter of said bubble is indicative of a time when each of said one or more contact events ends. In some implementations, the first point is located 180° from said second point around said perimeter. In some implementations, the bubble comprises a circle. In some implementations, the bubble comprises an oval. In some implementations, a size of the visual representation is indicative of said continuous period of time.

In some implementations, the proximity data is determined based on a detected Bluetooth® signal strength between the wearable device and the separate wearable device. In some implementations, the computing device comprises a mobile computing device. In some implementations, the mobile computing device is a smartphone. In some implementations, the computing device comprises a desktop or a laptop. In some implementations, the computing device is configured for operation by a third user. In some implementations, the threshold proximity is less than or equal to 20 ft. In some implementations, the threshold proximity is 6 ft.

In some implementations, the software application is configured to execute commands to enable the computing device to wirelessly receive said first identifier, said second identifier, and said proximity data over a network. In some implementations, the wearable device is configured to wirelessly transmit at least said second identifier and said proximity data to a mobile computing device, and wherein the software application is configured to execute commands to enable the computing device to wirelessly receive said first identifier, said second identifier, and said proximity data from the mobile computing device.

In some implementations, the mobile computing device is a smartphone. In some implementations, the wearable device is further configured to transmit said first identifier to said mobile computing device.

In some implementations, the visual representation comprises a circle, wherein a diameter of said circle is indicative of said continuous period of time. In some implementations, a first point on a perimeter of said circle is indicative of a time when each of said one or more contact events begins and a second point on said perimeter of said circle is indicative of a time when each of said one or more contact events ends. In some implementations, the first point is located 180° from said second point around said perimeter.

A system for monitoring one or more contact events for a user to limit a spread of an infection can include software instructions storable on a memory device usable by a computing device, the software instructions causing one or more hardware processors of the computing device to: receive, from a first wearable device configured to couple with a first user, proximity data indicative of distance between the first wearable device and a second wearable device that is configured to couple to a second user, said proximity data determined based on detected wireless signal strength between the first wearable device the second wearable device; receive, from the first wearable device, a first identifier associated with the first user of the first wearable device and a second identifier associated with the second user of the second wearable device; store said proximity data over time and determine one or more contact events based on said proximity data, wherein each of said one or more contact events is representative of the first and second users being within a threshold proximity from one another for a continuous period of time; generate a graphical user interface on a display of the computing device; display, in at least a portion of the graphical user interface, a timeline, said timeline being continuously updated over time; and display, in at least a portion of the graphical user interface, a visual representation of each one of said one or more contact events on said timeline.

In some implementations, the visual representation comprises a bubble, wherein a perimeter of said bubble is indicative of said continuous period of time. In some implementations, a first point on said perimeter of said bubble is indicative of a time when each of said one or more contact events begins and a second point on said perimeter of said bubble is indicative of a time when each of said one or more contact events ends. In some implementations, the first point is located 180° from said second point around said perimeter. In some implementations, the bubble comprises a circle. In some implementations, the bubble comprises an oval. In some implementations, a size of the visual representation is indicative of said continuous period of time.

In some implementations, the proximity data is determined based on a detected Bluetooth® signal strength between the wearable device and the separate wearable device.

In some implementations, the computing device comprises a mobile computing device. In some implementations, the mobile computing device is a smartphone. In some implementations, the computing device comprises a desktop or a laptop. In some implementations, the computing device is configured for operation by a third user. In some implementations, the threshold proximity is less than or equal to 20 ft. In some implementations, the threshold proximity is 6 ft.

In some implementations, the software application is configured to execute commands to enable the computing device to wirelessly receive said first identifier, said second identifier, and said proximity data over a network. In some implementations, the wearable device is configured to wirelessly transmit at least said second identifier and said proximity data to a mobile computing device, and wherein the software application is configured to execute commands to enable the computing device to wirelessly receive said first identifier, said second identifier, and said proximity data from the mobile computing device. In some implementations, the mobile computing device is a smartphone. In some implementations, the wearable device is further configured to transmit said first identifier to said mobile computing device.

In some implementations, the visual representation comprises a circle, wherein a diameter of said circle is indicative of said continuous period of time. In some implementations, a first point on a perimeter of said circle is indicative of a time when each of said one or more contact events begins and a second point on said perimeter of said circle is indicative of a time when each of said one or more contact events ends. In some implementations, the first point is located 180° from said second point around said perimeter.

For purposes of summarizing the disclosure, certain aspects, advantages, and novel feature are discussed herein. It is to be understood that not necessarily all such aspects, advantages, or features will be embodied in any particular embodiment of the disclosure, and an artisan would recognize from the disclosure herein a myriad of combinations of such aspects, advantages, or features.

BRIEF DESCRIPTION OF THE DRAWINGS

The following drawings and the associated descriptions are provided to illustrate embodiments of the present disclosure and do not limit the scope of the claims.

FIGS. 2A-2I illustrate exemplary wearable devices in accordance with aspects of this disclosure.

FIGS. 3A-3B illustrate exemplary interactions of wearable devices of users in accordance with aspects of this disclosure.

FIGS. 9A-14B illustrate exemplary user interfaces or portions thereof that can be employed by any of the computing devices discussed herein in accordance with aspects of this disclosure.

DETAILED DESCRIPTION

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below.

Overview

Figure 1:
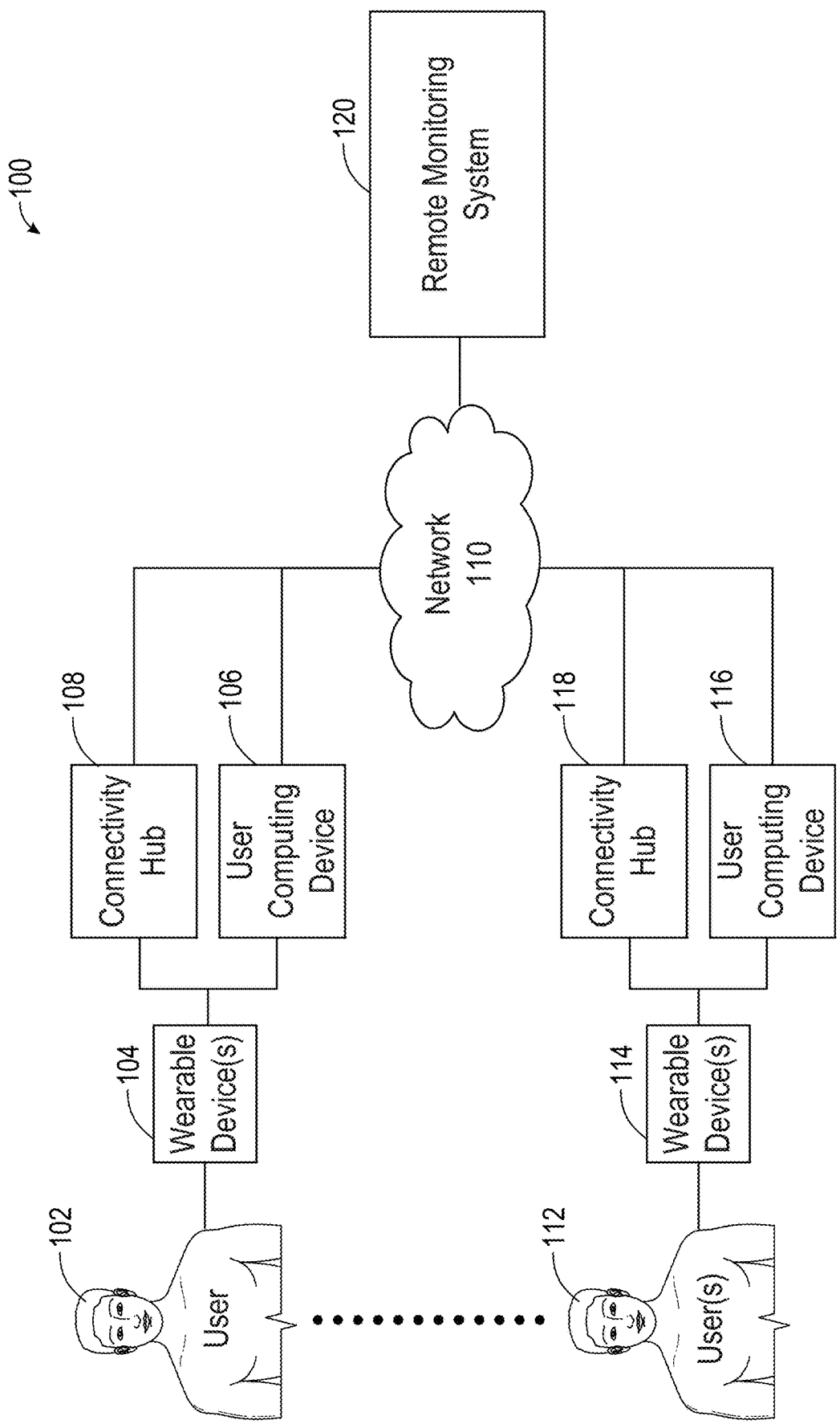
FIG. 1 illustrates an exemplary system or environment in accordance with aspects of this disclosure.

FIG. 1 illustrates an exemplary schematic diagram of a system or network environment 100 where information relating to one or more users 102, 112 can be communicated (for example, over a network 110) from wearable device(s) 104, 114, user computing devices 106, 116, and/or connectivity hubs 108, 118 to a remote monitoring and system 120 (also referred to herein as "remote monitoring system"). System 100 can be associated with and/or representative of an organization, such as a corporation, school, hospital, company managing a sports or concert or attraction venue, among others. System 100 can include any number of users. For example, system 100 can include user 102 and any number of additional users 112, such as one, two, three, four, five, six, seven, eight, nine, or ten or more, between 1 and 5000, between 1 and 2000, between 1 and 1000, 1 and 500, 1 and 200, 1 and 100, 1 and 50, or 1 and 20 users or any number within these ranges or bounded by any range including any value within these ranges. System 100 can also include any number of wearable devices 104, 114, connectivity hubs 108, 118, and/or user computing devices 106, 116 corresponding to the number of users 102, 112.

Any number of wearable devices 104, 114 can be associated with (for example, coupled to) users associated with the system 100 (such as users 102, 112) and can be configured to measure and/or monitor a variety of types of information associated with the user, such as physiological information as well as other types of information (such as location data, movement data, etc.). Wearable device(s) 104, 114 can communicate physiological and/or other information associated with the users 102, 104 to the remote monitoring system 120 over a network 110, for example, via a connectivity hub 108 and/or a user computing device 106. Additionally or alternatively, wearable device(s) 104, 114 can communicate physiological and/or other information associated with the users 102, 104 directly to the remote monitoring system 120 (for example, without utilization of connectivity hub 108, 118 and/or user computing devices 106, 116) for example, over network 110 or over a wireless communication protocol such as any of those listed herein. For example, if the wearable device 104, 114 is within a relatively short distance from the remote monitoring system 120, wearable device 104, 114 can be configured to transmit physiological and/or other information associated with the users 102, 104 directly to the remote monitoring system 120. As another example, any of such wearable devices 104, 114 can be a smart watch configured to determine one or more types of physiological information (e.g., oxygen saturation, heart rate, pulse rate, etc.) and/or other information (e.g., location and/or movement data from accelerometer(s), gyroscope(s), magnetometer(s) of the smart watch, proximity data between one or more other wearable devices of other users such as that discussed herein) and can transmit such information directly to the remote monitoring system 120. One, two, three, four, or five or more wearable devices 104, 114 can be coupled with the user 102, 112 and can measure and/or monitor (non-invasively or invasively) physiological information as well as other types of information of the user 102, 112. In some cases, only one wearable device 104, 114 is secured to a user 102, 112. Any or all of the wearable devices and/or the user computing devices discussed herein can include one or more sensors that can obtain information associated with position, acceleration, orientation, and/or movement of a user, for example, an accelerometer, a gyroscope, and/or a magnetometer.

Wearable devices 104, 114 can communicate with any of connectivity hub 108, 118 and/or user computing device 106, 116 via a wired connection (for example, a cable) and/or wirelessly over any of a variety of wireless communication protocols, such as Wi-Fi (802.11x), Bluetooth®, ZigBee®, Z-Wave®, cellular telephony, infrared, RFID, satellite transmission, proprietary protocols, combinations of the same, among others. Similarly, any of connectivity hub 108, 118 and/or user computing device 106, 116 can wirelessly communicate with the wearable devices 104, 114 over any of such mentioned wireless communication protocols. In some cases, any of connectivity hub 108, 118 and/or user computing device 106, 116 can wirelessly communicate with the remote monitoring system 120 over any of such mentioned wireless communication protocols, among others. In some cases, the wearable device 104, 114 communicate (e.g., respectively) with user computing device 106, 116 via a first wireless communication protocol and the user computing device 106, 116 communicate with the remote monitoring system 120 over a second wireless communication protocol. Such first and second wireless communication protocols can be different or, alternatively, the same.

Wearable devices 104, 114 can be any device that can be (at least partially) coupled with (for example, secured to) a user 102, 112 and can measure, monitor, and/or detect information associated with the user 102, 112, such as physiological information or other information (e.g., location and/or movement data and/or proximity data such as that discussed herein). Wearable devices 104, 114 can non-invasively and/or invasively measure or monitor physiological information of a user 102, 112. As an example, wearable devices 104, 114 can be devices capable of administering one or more medications to the user 102, 112. Wearable devices 104, 114 can be any of the wearable devices discussed herein, such as wearable device 200, 210, 220, 230, 240, 250, 260, and/or 270, among others. As another example, wearable devices 104, 114 can be any commercially available wearable device from Masimo Corporation of Irvine California, or other medical device manufacturer, including but not limited to noninvasive, minimally invasive, or microinvasive glucose sensors, oximetry or cooximetry sensors, pulse rate sensors, cuff and/or continuous noninvasive blood pressure sensors, capnography sensors, acoustic sensors, motion sensors including accelerometers and gyroscopes, pH sensors, image capture sensors using virtually any type of signal and/or wavelength filters, ECG, depth of sedation, pulse transit time or other parameter responsive to pulse transit time, cardiac parameter sensor, ultrasonic sensor, magnetic imagining sensor, x ray sensor, infrared sensor, proximity sensors, GPS or other location sensors, or the like or combinations thereof. In some cases, wearable devices 104, 114 can be configured to secure to various locations of a user's body including, but not limited to, chest, torso, back, shoulder, arms, legs, neck, or head. Various means can be used to attach the wearable devices 104, 114 to a user. For example, the wearable devices 104, 114 can be secured to the skin of a user with an adhesive. In another example, the wearable devices 104, 114 can be attached to a user with a fastener, such as tape, laid over at least a portion of the wearable devices 104, 114. Additionally or alternatively, the wearable devices 104, 114 can be attached to a user via one or more straps.

Connectivity hub 108, 118 can be a Wi-Fi hotspot, router, or "smart home hub" such as those commercially available by Amazon®, Google®, Samsung®, Apple®, or others. User computing device 106, 116 can be a laptop, mobile phone (for example, smart phone), watch (for example, a smart watch that can measure and/or monitor one or more physiological parameters), tablet, desktop, personal digital assistant (PDA), smart glasses, or other computing device capable of communicating with wearable device 104, wirelessly or via a wired connection, such as those discussed herein. In some cases, wearable devices 104, 114 can communicate with (for example, transmit data to) one of the connectivity hub 108, 118 or the user computing device 106, 116 depending on which has a more reliable connection. User computing device 106, 116 can include a processor, storage device, and/or wireless (and/or wired) communication capabilities that can allow communication (for example, receipt and transmission of information) to and from wearable device 104, 114 and/or remote monitoring system 120. In some implementations, system 100 does not include a connectivity hub, such as connectivity hub 108, 118.

User computing device 106, 116 and/or connectivity hub 108, 118 can transmit health-related information and/or other information received from the wearable device 104, 114 to the remote monitoring system 120 for analysis, storage, and/or monitoring/management. Additionally or alternatively, user computing device 106, 116 can transmit health-related information and/or other information obtained by the user computing device 106, 116 itself (for example, as opposed to being obtained from the wearable device 104, 114) to the remote monitoring system 120 for analysis, storage, and/or monitoring/management. Such health health-related information (which may also be referred to herein as "health status information" and/or "health risk information") can include any information that may be associated with, representative of, and/or indicative of a user's health. Such health health-related information can include, without limitation: physiological information of a user; information related to proximity of the user to one or more (or a plurality of) other users (for example, for determination of contact tracing and/or exposure to potential infections and/or diseases); information and/or data related to a user's diagnosis and/or test result(s) with respect to one or more infections and/or diseases (e.g., positive and/or negative test results, diagnosis obtained from a medical professional); and information and/or data related to symptom(s) experienced by the user (which can be input by the user into a computing device operated by a user, for example).

In some implementations, the user computing device 106, 116 can allow a user 102, 112 to authorize the transmission (for example, "sharing") of health-related information with the remote monitoring system 120 and/or other third parties or third party devices that may be able to communicate with and/or access remote monitoring system 120. In some implementations, the user computing device 104, 114 can transmit an alert to the remote monitoring system 120 based on health-related information received from the wearable devices 104, 114 and/or inputted or determined by the user computing device 106, 116. Such alert can be associated with, by way of non-limiting example: a body temperature of a user 102, 112 over a threshold value measured by the wearable device 104, 114 and transmitted to the user computing device 106, 116; contact tracing data determined by the wearable device 104, 114 and/or user computing device 106, 116 indicative of proximity of the user 102, 112 to one or more other users over a period of time and/or health statuses (for example, risk state(s)) of such one or more other users over such period of time; a diagnosis received from a care provider associated with the user 102, 112 and inputted by the user 102, 112 into the user computing device 106, 116; and/or symptom(s) information of, and inputted by, the user 102 into the user computing device 106, 116.

Connectivity hubs 108, 118 can be configured in a similar or identical manner as discussed above with reference to user computing device 106, 116. In some implementations, the user computing device 106, 116 can be utilized to configure (for example, program) connectivity hub 108, 118 such that it can carry out any of functions/operations described above with reference to the user computing device 106, 116, alone or in combination with the user computing device 106, 116 (for example, when there is a stronger connection between the wearable device 104, 114 and the connectivity hub 108, 118 than with the user computing device 106, 116).

In some implementations, a user 102 can authorize their health-related information or other information to be shared with another user 112. For example, in some implementations, a user 102 can authorize (via user computing device 106) the transmission of health-related information determined by the wearable device(s) 104 from connectivity hub 108 and/or user computing device 106 to the connectivity hub 118 and/or user computing device 116. Similarly, in some implementations, a user 102 can authorize (via user computing device 106) the receipt of health-related information determined by the wearable device(s) 114 from connectivity hub 118 and/or user computing device 116 to the connectivity hub 108 and/or user computing device 106.

User computing device 106, 116 (and/or any of the other computing devices discussed herein) can be configured to execute one or more applications that can present graphical user interfaces on, for example, a display of the user computing device 106, 116. Such applications and/or graphical user interfaces can advantageously display physiological and/or other information received from the wearable device(s) 104, 114 and/or can communicate information to the user 102, 112, for example, instructions and/or information received from the remote monitoring system 120. User computing device 106, 116 can allow a user 102, 112 to share health-related information that evidences their current physiological condition. By way of non-limiting example, utilizing the user computing device 106, a user 102 could clear themselves for work each day, clear themselves to enter a particular business establishment, like a diner, shopping, sports venue, concert venue, attraction venue, or gym, clear themselves as a spectator or participant for large or small event gatherings, including sports, marriages, religious endeavors, concerts, performances, school attendance, hospital or nursing home admittance, admittance to flights, car services, public transportation of all manners, even meeting with a small group of friends or going on a date. Being able to provide electronically obtained evidence (for example, physiological information obtained from the wearable device(s) 104 and/or inputted into the user computing device 106) that a person's current wellness is "normal" (e.g., within medically accepted standards) for that person can easily be the gating function for virtually any and all daily interactions and activities. For example, showing a mobile phone's displayed indication that "I'm green," or transmitting some signal indicating the same, may advantageously become a default greeting or admittance requirement for an almost limitless number of possible scenarios.

User computing device 106, 116 can allow a user 102, 112 to input various health-related information, including but not limited to: a diagnosis received from a care provider (for example, whether the user is confirmed for an infection); symptom(s) information (for example, fever, chills, cough, shortness of breath or difficulty breathing, fatigue, muscle or body aches, headache, loss of taste or smell, congestion or runny nose, nausea or vomiting, diarrhea, among others); and/or contract tracing data (for example, proximity with other user who had or are suspected to have an infection). Diagnosis and/or symptom(s) information can be any of that which is described herein, among others. Symptom(s) information can be obtained by the user computing device 106, 116 based on questionnaire(s) provided to the user 102, 112, among other methods (e.g., allowing the user to manually enter symptoms). The questionnaire(s) can include questions related to the symptoms the user (e.g., symptoms related to COVID-19 or other communicable diseases) is experiencing or medical tests that the user has taken. For example, the user computing device 106, 116 can include an application that can present (e.g., via execution by one or more processors of the user computing device 106, 116) the following example symptoms questionnaire to the user via a display of the user computing device 106, 116: In the last 24 hours have you: Developed a cough? Experienced shortness of breath? Experienced chills? Experienced muscle pain? Lost the sense of taste or smell? Experienced nausea, vomiting, or diarrhea? Experienced loss of appetite? Experienced fatigue? As another example, the application can present the following example medical tests questionnaire to the user: "In the last two weeks have you had a PCR Coronavirus Test?" "If yes, when and what was the result?" "Have you had an Antibody Test?" "If yes, when and what was the result?" These questions are not exhaustive of those that can be used. Further it will be appreciated that additional questions related to other diseases could also be utilized. The frequency of the questionnaires can be configured to be any amount of time. For example, the application can present the symptoms questionnaire to the user 102, 112 on a daily basis and the medical tests questionnaire on a weekly basis. If the user 102, 112 fails to complete the questionnaires every day or every week, then the remote monitoring system 120 can modify a risk state of the user 102, 112 accordingly, for example, by increasing the user's risk state which is described in more detail elsewhere herein (for example, can determine that the user is in a "yellow" risk category).

Remote monitoring system 120 can be configured to communicate with (for example, receive information from and/or transmit information to) any number of user computing devices 106, 116, connectivity hubs 108, 118, and/or wearable devices 104, 114 associated with any number of users 102, 112. For example, remote monitoring system 120 can be configured to receive data from and/or transmit data to one, two, three, four, five, six, seven, eight, nine, or ten or more, between 1 and 5000, between 1 and 2000, between 1 and 1000, between 1 and 500, between 1 and 200, between 1 and 100, between 1 and 50, or between 1 and 20 of user computing devices 106, 116, connectivity hubs 108, 118, and/or wearable devices 104, 114, or any number within these ranges or bounded by any range including any value within these ranges. Advantageously, as will be discussed in greater detail below, remote monitoring system 120 can be utilized by an organization (e.g., business, school, hospital), or a user thereof (for example, a "monitor user" tasked with overseeing and/or taking action with respect to the remote monitoring system 120), to monitor and/or manage health statuses of users 102, 112 associated with the organization in order to limit the spread of an infectious disease or otherwise protect the health of such users 102, 112. As also discussed herein, the remote monitoring system 120 can advantageously allow continuous, automatic, and simultaneous receipt of health-related and/or other information from a large number of users associated with an organization and also allow health statuses, exposure levels, and/or risk states/statuses of each user to be dynamically determined and updated in real time.

Exemplary Wearable Devices

FIGS. 2A-2I illustrate exemplary wearable devices 200, 210, 220, 230, 232, 240, 250, 260, 270, and are described further below. As discussed previously, wearable device 104, 114 can be any of wearable devices 200, 210, 220, 230, 240, 250, 260, and/or 270, among others.

Figure 2B:
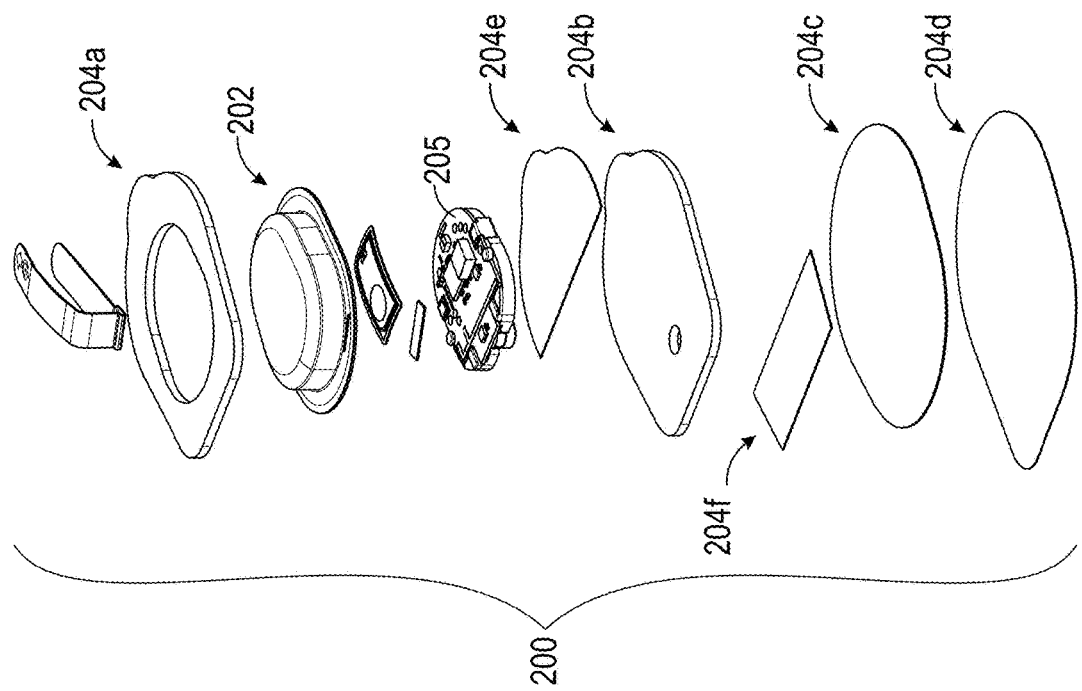
Figure 2A:
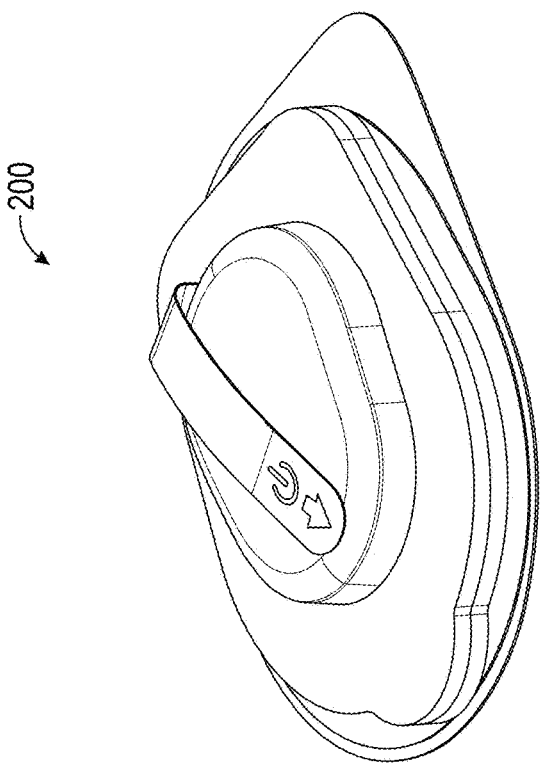

FIGS. 2A-2B illustrate a wearable device 200 that can continuously or periodically measure and/or monitor body temperature of a user, among other physiological parameters and/or information. Wearable device 200 can include a housing 202 and one or more substrates 204*a*, 204*b*, 204*c*, 204*d*, 204*e*, 204*f*, which are coupled to the housing 202 and/or other components of the wearable device 200 and which can enable, among other things, the wearable device 200 to couple with (for example, secure to skin of) a user. Wearable device 200 can additionally include a processor, a storage device, a wireless transceiver, a power source (for example, a battery), information element, and/or one or more temperature sensors (such as one, two, or three temperature sensors). For example, as discussed elsewhere herein, wearable device 200 can include any of processor 302, storage device 304, wireless transceiver 306, power source 308, information element 310, physiological sensor (s) 312, and/or other sensor(s) 314 discussed below with respect to FIG. 2J. Any of the processor, storage device, wireless transceiver, battery, information element, and/or one or more temperature sensors of wearable device 200 can be mounted and/or coupled with a circuit layer of the wearable device 200, such as a circuit board 205 of the wearable device 200, which can be enclosed or at least partially enclosed by the housing 202 (and/or a portion of the housing 202) and/or one or more substrates 204a, 204b, 204c, 204d, 204e, 204f. In some implementations, wearable device 200 is configured to determine only one type of physiological parameter, for example, body temperature. In such configurations, a battery life of the wearable device 200 can be maximized.

As discussed above, the wearable device 200 can include one or more temperature sensors, and such one or temperature sensors can be or include, a thermocouple and/or a thermistor, for example. A thermocouple can produce a voltage when the contact spot differs from a reference temperature. Thermocouples may be self-powered and therefore may not require an external power source for operation. A thermistor is a type of resistor whose resistance value can vary depending on its temperature. Thermistors typically offer a high degree of precision within a limited temperature range. The one or more temperature sensors of the wearable device 200 can be a chip that is electrically and mechanically coupled with the circuit board 205. The one or more temperature sensors of the wearable device 200 can be configured to generate one or more signals responsive to detected thermal energy of a user, determine body temperature, and/or transmit such generated one or more signals and/or such determined body temperature to the processor of the wearable device 200 continuously and/or intermittently. For example, the one or more temperature sensors of the wearable device 200 can be configured to generate one or more signals responsive to detected thermal energy, determine body temperature, and/or transmit such generated one or more signals and/or such determined body temperature every 0.5 seconds, 1 second, 2 second, 3 seconds, 4 seconds, 5 seconds, 10 seconds, 30 seconds, 1 minute, 2 minute, 3 minutes, 4 minutes, 5 minutes, or at other intervals.

Wearable device 200 can be similar or identical to any of the wearable devices disclosed in co-pending U.S. patent application Ser. No. 17/206,907, filed on Mar. 19, 2021, titled "WEARABLE DEVICE FOR NONINVASIVE BODY TEMPERATURE MEASUREMENT," which is hereby incorporated by reference in its entirety.

FIGS. 2C-2I illustrate other exemplary wearable devices 210, 220, 230, 240, 250, 260, 270 that can be utilized alone or in combination with one another and/or with wearable device 200 in system 100, for example, as wearable devices coupled and/or associated with user 102, 112 and in communication (e.g., wireless) with user computing device 106, 116 and/or connectivity hub 108, 118. Any or all of wearable devices 210, 220, 230, 240, 250, 260, 270 can be secured to various portions of a user's body and/or can be configured to wirelessly communicate with separate devices which are not secured and/or not near the user's body. FIGS. 2C-2F illustrate an exemplary user computing device 206 that can be, for example, a smartphone. However, any of the wearable devices 210, 220, 230, 240, 250, 260, 270 can be configured to communicate (e.g., wirelessly or via a cable) with any type of computing device such as any of those discussed herein.

FIG. 2C illustrates a wearable device 210 that can secure to a user's arm (for example, wrist). Wearable device 210 can be secured to the user's wrist via a strap, as shown. Wearable device 210 can be similar or identical to any of the wearable devices and/or sensor systems disclosed in U.S. Patent Pub. No. 2020/0138288, filed on Oct. 10, 2019, titled "SYSTEM FOR TRANSMISSION OF SENSOR DATA USING DUAL COMMUNICATION PROTOCOL," which is hereby incorporated by reference in its entirety. Wearable device 210 does not have to be physically attached to a monitoring device or a computing device (such as user computing device 106, 116), for example, via a cable, and can be configured for wireless communication. Therefore, a user may be able to move around, for example, in their home, hospital room, hotel room, place of employment, school, or outdoor area (for example, parks, beaches, and malls), without having to worry about cables or cords limiting their range of movement. Wearable device 210 can establish wireless communication with nearby devices to securely transmit physiological data or other data collected from a user. As illustrated in FIG. 2C, wearable device 210 can be configured to wirelessly communicate with a separate computing device 206, which can be a mobile phone, for example, among other types of computing devices such as any of those discussed herein (for example, laptop, desktop, tablet, among others). Wearable device 210 can be configured to communicate with computing device 206 (or any other computing device) over a wireless communication protocol such as any of those discussed elsewhere herein. For example, wearable device 210 can be configured to communicate to computing device 206 via Bluetooth®.

FIG. 2D illustrates another example wearable device 220. Wearable device 220 can include a sensor 222 and a cable assembly 224. As shown, the sensor 222 can be coupled to computing device 206 via the cable assembly 224. Accordingly, the computing device 206 may receive user physiological data from the sensor 222 via the cable assembly 224. The sensor 222 can be powered by a power source of the user computing device 206, which may have greater capacity than a battery of the wearable device 220 (for example, a battery that may be within sensor 222). As such, the configuration of the wearable device 220 and the computing device 206 can collect physiological data for a longer period of time relative to some other types of devices and/or configurations. User physiological data can be transmitted to the computing device 206 via the cable assembly 224, which may avoid some security challenges present in some wireless data transmission methods. A portion of the wearable device 220 can be secured to a user. For example, the sensor 222 can be secured to a user's finger or toe, or another portion of a user. The sensor 222 can be a pulse oximeter, for example the Masimo Rainbow® pulse oximeter. Wearable device 220 can be similar or identical to any of the physiological monitoring systems disclosed in U.S. Pat. No. 9,877,650, issued on Jan. 30, 2018, titled "PHYSIOLOGICAL MONITOR WITH MOBILE COMPUTING DEVICE CONNECTIVITY," which is hereby incorporated by reference in its entirety.

Figure 2F:
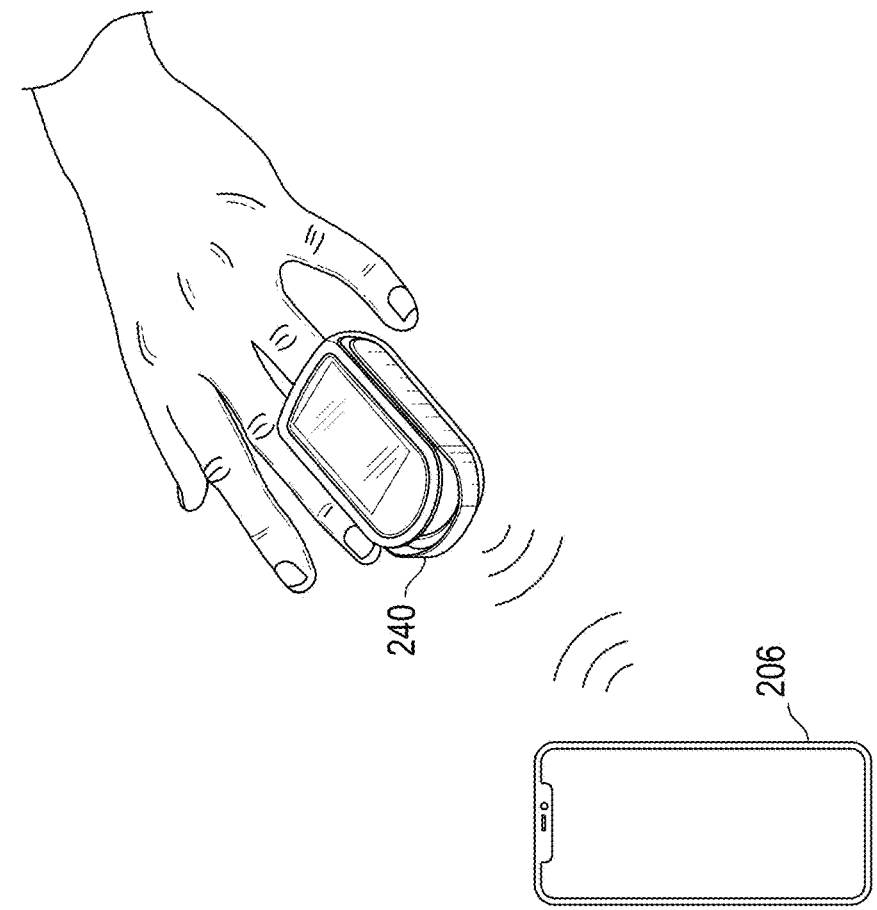
Figure 2E:
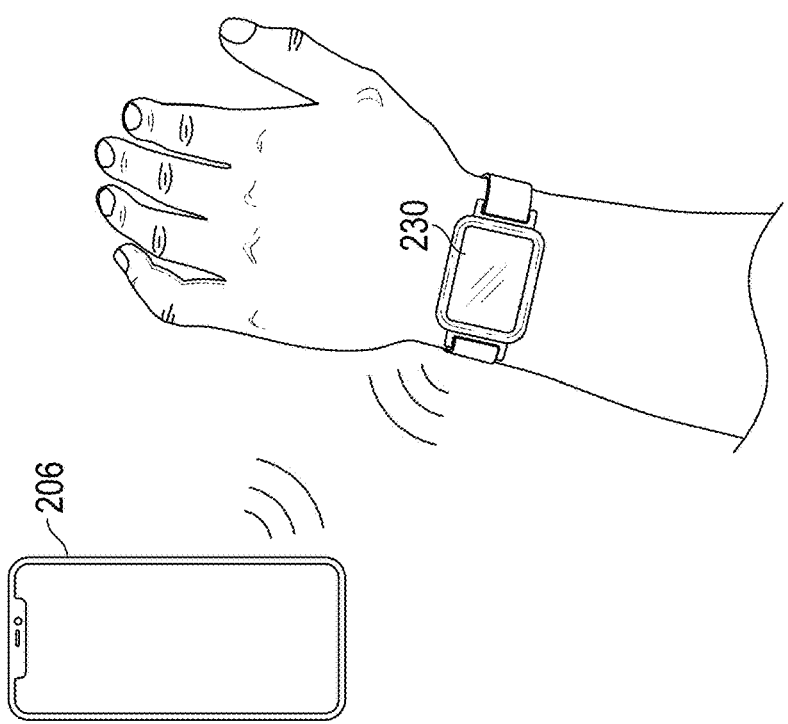

FIG. 2E illustrates another example wearable device 230. Wearable device 230 can be, for example, a smartwatch configured to measure and/or monitor one or more physiological parameters of a user (e.g., oxygen saturation, pulse rate, heart rate) and/or other information of a user (e.g., location and/or movement data determined from accelerometer(s), gyroscope(s), magenetometer(s) of the smartwatch). In some implementations, wearable device 230 can be configured to detect proximity to other wearable devices that may be associated with (e.g., attached to) other users, in a similar or identical manner as that discussed elsewhere herein. Wearable device 230 can wirelessly transmit such data to a computing device 206. Wearable device 230 can be configured to communicate over a wireless communication protocol such as any of those discussed elsewhere herein. Wearable device 220 can be similar or identical to any of the wearable devices, physiological sensors, and/or watches disclosed in U.S. patent application Ser. No. 17/148,303, filed on Jan. 13, 2021, titled "WEARABLE DEVICE WITH PHYSIOLOGICAL PARAMETERS MONITORING," which is hereby incorporated by reference in its entirety.

FIG. 2F illustrates another example wearable device 240. Wearable device 240 can be a fingertip pulse oximeter, for example, the MightySat® Rx Fingertip Pulse Oximeter by Masimo Corporation, Irvine, CA. Wearable device 240 can be configured to wirelessly communicate one or more physiological parameters of the user (e.g., oxygen saturation, pulse rate, heart rate) to the user computing device 206.

Figure 2G:
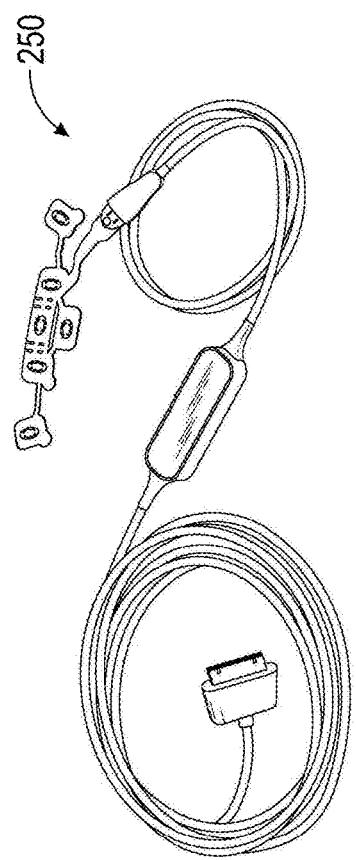
Figure 2I:
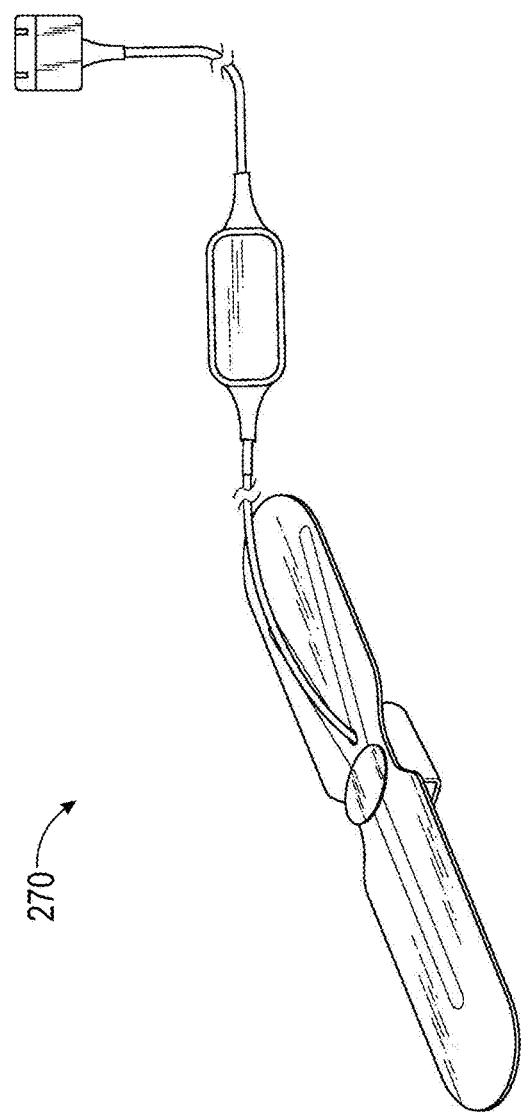
Figure 2H:
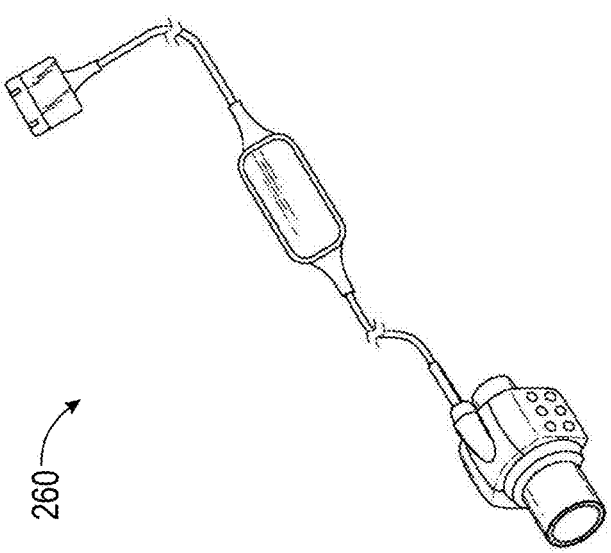

FIGS. 2G-2I illustrate additional exemplary wearable devices 250, 260, 270 that can measure and/or monitor physiological data of a user and transmit indications of the user's physiological parameters to a user computing device, such as computing device 206. As illustrated, wearable devices 250, 260, 270 can transmit such data to a computing device 206 via a cable.

Wearable device 250 can include a processor and an electrocardiogram (ECG) sensor and/or an electroencephalograph (EEG) sensor. A portion of the wearable device 250 can be secured to a user to measure and/or monitor one or more physiological parameters and/or detect signals (for example, electrical signals) generated by the user. The ECG sensor may capture one or more physiological signals related to cardiac activity. The processor of the wearable device 250 can process the one or more physiological signals to measure the user's cardiac activity and/or to detect arrhythmias, such as bradycardia, tachyarrhythmia, or ventricular fibrillation. In some implementations, wearable device 250 can transmit unprocessed data to a separate computing device for processing thereon, for example, to determine such above-mentioned cardiac-related characteristics. Alternatively or additionally, wearable device 250 can include EEG sensor that can be configured to measure electrical activity along the scalp and/or forehead. Wearable device 250 can be similar or identical to any of the forehead sensors or systems disclosed in U.S. Pat. No. 8,821,397, issued on Sep. 2, 2014, titled "DEPTH OF CONSCIOUSNESS MONITOR INCLUDING OXIMETER," which is hereby incorporated by reference in its entirety. Wearable device 250 can be similar or identical to any of the modular physiological sensors or systems disclosed in U.S. Pat. No. 10,154,815, issued on Dec. 18, 2018, titled "MODULAR PHYSIOLOGICAL SENSORS," which is hereby incorporated by reference in its entirety.

FIG. 2H illustrates a wearable device 260 that includes a capnometer or capnograph that can be configured to measure components of expired breath.

FIG. 2I illustrates a wearable device 270, a portion of which can secure to a user. Wearable device 270 an acoustic respiration sensor that can capture one or more physiological signals related to vibrational motion from the user's body (e.g., the user's chest) that are indicative of various physiologic parameters and/or conditions, including without limitation, heart rate, respiration rate, snoring, coughing, choking, wheezing, and respiratory obstruction (e.g., apneic events). Wearable device 270 includes an acoustic respiratory monitor sensor that can be configured to measure respiration rate using an adhesive sensor with an integrated acoustic transducer. Additional details regarding an example acoustic respiration sensor are described in U.S. Pat. No. 8,771,204 titled "ACOUSTIC SENSOR ASSEMBLY," which is hereby incorporated by reference in its entirety.

Any of the wearable devices discussed herein, such as wearable device 104, 114, 200, 210, 220, 230, 240, 250, 260, and/or 270, can be similar or identical to any of the devices for measuring and/or monitoring one or more physiological parameters disclosed in U.S. Pat. Pub. No. 2020/0329993, published on Oct. 22, 2020, titled "ELECTROCARDIOGRAM DEVICE," which is hereby incorporated by reference in its entirety.

Figure 2J:
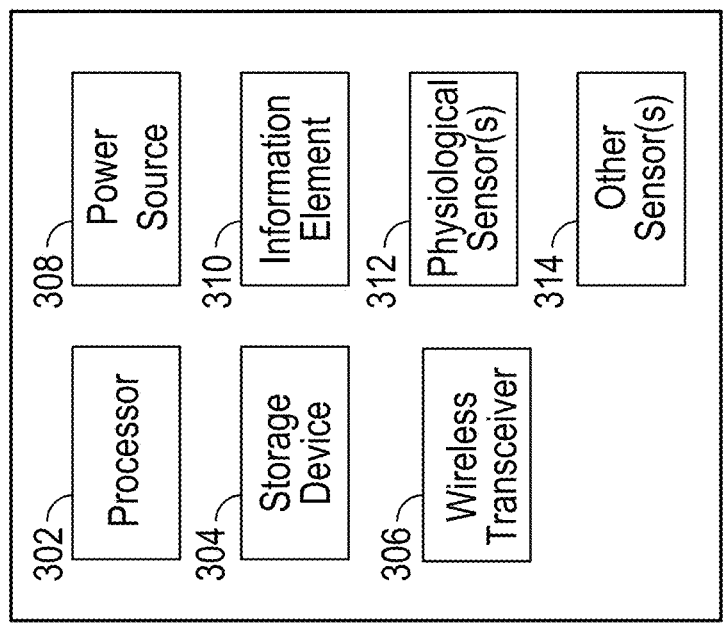
FIG. 2J illustrates exemplary components that can be incorporated into any of the wearable devices described herein in accordance with aspects of this disclosure.

FIG. 2J illustrates a block diagram of exemplary components which can be incorporated, all or in part, into any of the wearable devices discussed herein, such as wearable device 104, 114, 200, 210, 220, 230, 240, 250, 260, and/or 270. Any of the wearable devices discussed herein, such as wearable device 104, 114, 200, 210, 220, 230, 240, 250, 260, and/or 270, can include one or more of a processor 302, storage device 304, communication interface such as a wireless transceiver 306, power source 308, and/or information element 310. Any of the wearable devices discussed herein, such as wearable device 104, 114, 200, 210, 220, 230, 240, 250, 260, and/or 270, can include one or more physiological sensors 312 configured to monitor and/or measure one or more physiological parameters of a user and/or generate one or more signals responsive to detecting characteristics of the user. Such sensors 312 can be for example, optical sensors (which also may be referred to herein as "oximetry sensors" and/or "pulse oximeters"), moisture sensors, impedance sensors, ECG sensors, EEG sensors, acoustic respiration sensors, and/or temperature sensors, among others. Any of the wearable devices discussed herein, such as wearable device 104, 114, 200, 210, 220, 230, 240, 250, 260, and/or 270, can be configured to measure and/or monitor physiological data including, but not limited to, temperature, blood pressure, pulse rate, heart rate, respiratory rate (RRa), total hemoglobin (SpHb®), carboxyhemoglobin (SpCO®), methemoglobin (SpMet®), oxygen content (SpOC™), oxygen saturation (SpO2), pulse rate (PR), perfusion index (Pi), blood pressure, pleth variability index (PVi®), electroencephalogram (EEG) data, trending values of the same or combinations of the same, wellness indexes, or the like. Any of the wearable devices discussed herein, such as wearable device 104, 114, 200, 210, 220, 230, 240, 250, 260, and/or 270, can include one or more other sensors 314, such as one or more accelerometers, gyroscopes, magnetometer (compass), among others. Such sensors 314 can provide information associated with the user that can be used, processed, and/or transmitted alone or in combination with physiological data such as that discussed above. Any of such physiological data or other user information can be measured, monitored, and/or detected by sensor(s) 312 and/or 314 continuously and/or intermittently.

The processor 302 can be configured, among other things, to process data, execute instructions to perform one or more functions, and/or control the operation of the wearable device 104, 114, 200, 210, 220, 230, 240, 250, 260, and/or 270. For example, the processor 302 can process physiological data obtained from the wearable device 104, 114, 200, 210, 220, 230, 240, 250, 260, and/or 270 and can execute instructions to perform functions related to storing and/or transmitting such physiological data, for example, to a separate computing device. For example, the processor 302 can process data received from one or more physiological sensors 312 and can execute instructions to perform functions related to storing and/or transmitting such received data.

The storage device 304 can include one or more memory devices that store data, including without limitation, dynamic and/or static random access memory (RAM), programmable read-only memory (PROM), erasable programmable read-only memory (EPROM), electrically erasable programmable read-only memory (EEPROM), and the like. Such stored data can be processed and/or unprocessed physiological data obtained from the wearable device 104, 114, 200, 210, 220, 230, 240, 250, 260, and/or 270, for example.

Any of the wearable devices discussed herein, such as wearable device 104, 114, 200, 210, 220, 230, 240, 250, 260, and/or 270, can include a wireless transceiver 306 or other communication interface or component configured to allow wireless communication with other wearable devices, computing devices (such as user computing device 106, 116), connectivity hubs (such as connectivity hub 108, 118), remote monitoring systems (such as remote monitoring system 120, and/or other devices or systems (such as remote monitoring system 120) over a variety of wireless communication protocols, such as Wi-Fi (802.11x), Bluetooth®, ZigBee®, Z-Wave®, cellular telephony, infrared, RFID, satellite transmission, proprietary protocols, combinations of the same, and the like. Additionally or alternatively, any of the wearable devices discussed herein (such as wearable device 104, 114, 200, 210, 220, 230, 240, 250, 260, and/or 270) can include near field communication (NFC) structure and/or functionality that can enable the wearable device to communicate with another wearable device (for example, to determine proximity thereto as discussed elsewhere herein) and/or with any of the computing devices discussed herein. For example, any of the wearable devices discussed herein (such as wearable device 104, 114, 200, 210, 220, 230, 240, 250, 260, and/or 270) can include an active or passive RFID tag that can allow an NFC reader of a separate device to register, track, and/or determine information about the wearable device such as an device identifier, among other things.

With continued reference to FIG. 2J, any of the wearable devices discussed herein, such as wearable device 104, 114, 200, 210, 220, 230, 240, 250, 260, and/or 270, can include a power source 308, such as a battery. The power source 308 can provide power for hardware components of the wearable device. The power source 308 can be, for example, a lithium battery. Additionally or alternatively, any of the wearable devices discussed herein (such as wearable device 104, 114, 200, 210, 220, 230, 240, 250, 260, and/or 270) can be configured to obtain power from a power source that is external to the wearable device. For example, any of the wearable devices discussed herein (such as wearable device 104, 114, 200, 210, 220, 230, 240, 250, 260, and/or 270) can include or can be configured to connect to a cable which can itself connect to an external power source to provide power to the wearable device.

Any of the wearable devices discussed herein, such as wearable device 104, 114, 200, 210, 220, 230, 240, 250, 260, and/or 270, can include an information element 310 which can be a memory storage element that stores, in non-volatile memory, information used to help maintain a standard of quality associated with the wearable device. Illustratively, the information element 310 can store information regarding whether the wearable device has been previously activated and whether the wearable device has been previously operational for a prolonged period of time, such as, for example, four hours. The information stored in the information element 310 can be used to help detect improper re-use of the wearable device for example.

FIGS. 3A-3B illustrate a first wearable device 200 coupled to a user 102 and a second wearable device 200' coupled to another user 112. Wearable device 200' can be identical to wearable 200 or alternatively, can be different (for example, can be the same as any other wearable device discussed herein). Wearable device 200, 200' can secure to a portion of a user's body, such as a torso, chest, back, arm, neck, leg, among other portions of the user's body. In some embodiments, multiple different, similar, or same wearable devices (such as any of those discussed herein) can be removably secured to virtually any one or more portions of the users' bodies.

Advantageously, in some implementations, each of wearable device 200, 200' can determine proximity to one another and/or to other wearable devices. Accordingly, the wearable devices 200, 200' can determine distance(s) between users 102, 112 when the wearable devices 200, 200' are coupled to the users 102, 112. Wearable device 200, 200' can transmit and/or receive one or more (or a plurality of) signals from each other, for example, at various time intervals (e.g., every 1 second, 3 seconds, 5 seconds, 10 seconds, 30 seconds, 1 minute). Such signal(s) can be communicated over one or more, or a plurality of wireless communication protocols, including but not limited to Wi-Fi (802.11x), Bluetooth®, ZigBee®, Z-Wave®, cellular telephony, infrared, RFID, satellite transmission, proprietary protocols, near-field communication (NFC), combinations of the same, and the like.

In some cases, a strength of a signal received and/or transmitted by the wearable device 200, 200' can be a function of a distance between the two devices, for example, a distance between a wireless transceiver (or transmitter) of one of the wearable device 200, 200' and a wireless transceiver (or receiver) of the other one of the device 200, 200'. FIG. 3A illustrates a first user 102 being a distance D1 from a second user 112 and FIG. 3B illustrates the first and second users 102, 112 being a distance D2 apart. As the two users 102, 112 move closer to one another, the distance between the two wearable device 200, 200' decreases to a value of D2, which is smaller than D1. Accordingly, signal strength of transmitted and received signals between the two wearable device 200, 200' can increase. In some implementations, each of wearable device 200, 200' can determine a proximity from one another based on a detected signal strength. For example, processors of the wearable device 200, 200' can compare one or more received signals and/or associated signal strength to one or more reference points in order to determine proximity values, for example, distances in feet, meters, or inches. In some implementations, wearable device 200, 200' (for example, processors thereof) can compare detected signal strength to one or more signal thresholds. For example, if the signal strength is over a signal threshold, the wearable device 200, 200' can determine that the distance between the devices 200, 200' and other devices and/or sensors is within some range or category. Such range or category can be, for example, "low", "medium", "high", "close", "far", and/or can be associated with ranges such as 0-6 ft, 6-20 ft, 20-50 ft, 50-100 ft for example. In some implementations, wearable devices 200, 200' are configured to detect proximity between one another when the distance between the two is within a proximity threshold. Such proximity threshold can be, for example, 200 ft, 100 ft, 80 ft, 70 ft, 60 ft, 50 ft, 40 ft, 30 ft, 20 ft, 15 ft, 10 ft, 9 ft, 8 ft, 7 ft, 6 ft, 5 ft, 4 ft, 3 ft, 2 ft, 1 ft, or any value between any of these values, or any range bounded by any combination of these values, although values outside these values or ranges can be used in some cases.

Although FIGS. 3A-3B illustrate wearable devices 200, 200' and the above-described proximity detection functionality is described with reference to wearable devices 200, 200', any of the wearable devices discussed herein (wearable device 104, 114, 200, 210, 220, 230, 240, 250, 260, and/or 270) can include such functionality and can be configured to detect proximity to one or more, or a plurality of, other wearable devices coupled to other users.

Any of the wearable devices discussed herein, such as wearable device 104, 114, 200, 210, 220, 230, 240, 250, 260, and/or 270, can be configured to detect proximity to one or more other wearable devices on other users (for example, when within a proximity threshold such as that discussed above) and can transmit proximity data (e.g., one or more proximity values) to a user computing device (such as computing device 206, 106, 116) at various intervals, for example, at every 0.5 seconds, 1 second, 2 second, 3 seconds, 4 seconds, 5 seconds, 10 seconds, 30 seconds, 1 minute, 2 minute, 3 minutes, 4 minutes, 5 minutes, 10 minutes, 30 minutes, or at other intervals.

Although FIGS. 3A-3B illustrate just wearable device 200, 200' coupled to a user 102, 112, various other numbers and/or types of wearable devices can be coupled to a user 102, 112 at once and can be configured to communicate with other wearable devices on the same user 102, 112 and/or other wearable devices coupled to other users. By way of non-limiting example, wearable device 200 and wearable device 210 (each of which are discussed above) can both be coupled to a user 102 and either of both of which can be configured to detect proximity to other wearable devices coupled to other users and/or can transmit data (e.g., physiological of other data) measured from and/or associated with the user 102, for example, to a user computing device (such as user computing device 206, 106, 116, among others).

Any of the wearable devices discussed herein (such as wearable device 104, 114, 200, 210, 220, 230, 240, 250, 260, and/or 270) can be configured for short, intermediate, or long term use. In some implementations, any of the wearable devices discussed herein (or portions thereof) can be configured to be coupled to (for example, adhesively secured to skin of) a user for a long period of time (for example, 1 day, 2 days, 3 days, 4 days, 5 days, 6 days, 7 days, 8 days, 9 days, or 10 days), can monitor (continuously or periodically) physiological information (for example, body temperature) and/or other information (for example, movement, orientation, location data) can transmit (for example, wirelessly) such physiological and/or other information to separate devices (for example, a mobile computing devices such as mobile phones). In some implementations, any of the wearable devices discussed herein are configured for hourly to daily one-time use, multi-day use, or even monthly use. In some implementations, any of the wearable devices discussed herein (or portions thereof) have reusable and/or disposable portions, and the reusable portions. In some implementations, any of the wearable devices discussed herein (or portions thereof) are fluid resistant and user sterilizable, for example, to allow a user to take a shower.

Remote Monitoring System

As discussed above, remote monitoring system 120 can be configured to communicate with (for example, receive data from and/or transmit data to) any number of user computing devices 106, 116, connectivity hubs 108, 118, and/or wearable devices 104, 114 associated with any number of users 102, 112. As also discussed above, remote monitoring system 120 can advantageously be used by an organization (e.g., business, school, hospital), and/or a user thereof (for example, a "monitor user" of the organization), to monitor and/or manage health statuses of users 102, 112 associated with the organization in order to limit the spread of an infectious disease or otherwise monitor the health of such users 102, 112. As another example, the remote monitoring system 120 can be utilized by an organization to facilitate clearance of one or more users for an event or gathering (e.g., by a sports or concert venue).

Figure 4:
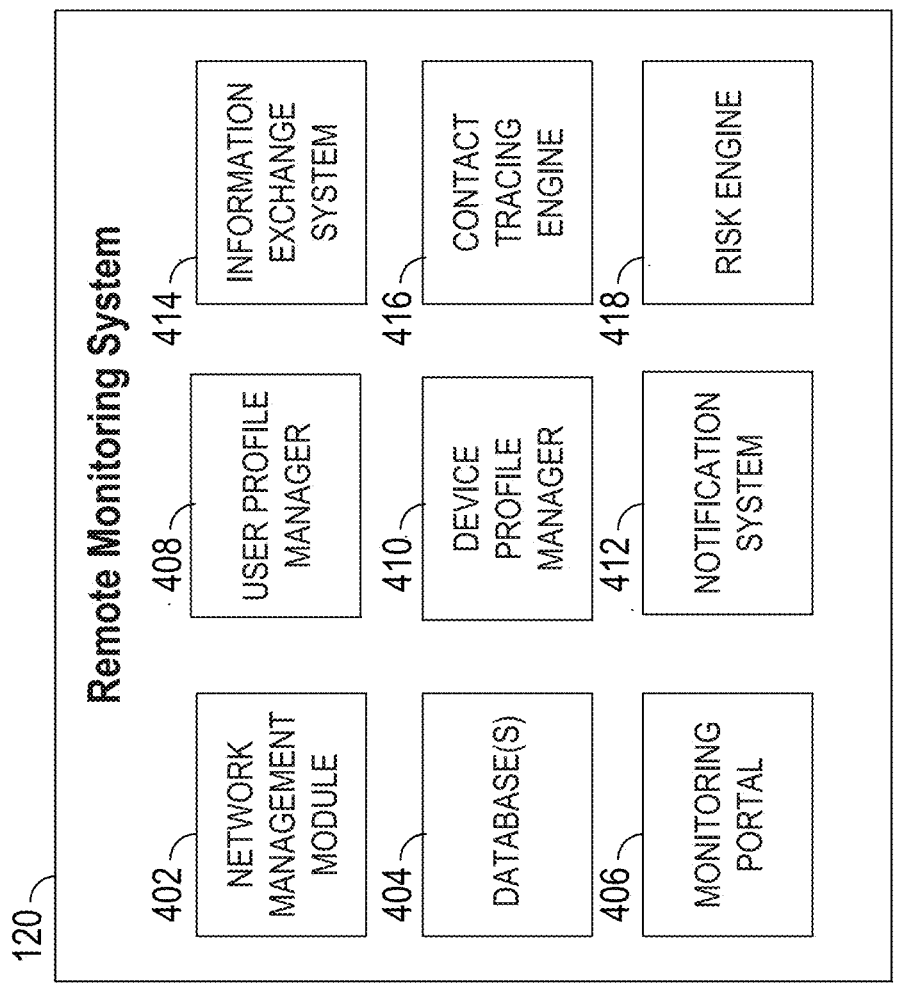
FIG. 4 illustrates exemplary components of a remote monitoring system in accordance with aspects of this disclosure.

FIG. 4 illustrates exemplary components any or all of which can be incorporated into remote monitoring system 120. The remote monitoring system 120 can include several subsystems and/or modules that can be implemented in hardware and/or software. The example modules or components shown may group functionality of examples of the remote monitoring system 120 together under logical descriptions. It should be understood, however, that the various modules and systems shown in the remote monitoring system 120 or portions thereof could be implemented together in a single system. In addition, not all of the systems or modules shown need be implemented on the same computing device but could instead be implemented in separate computing devices. Further, some of the modules shown may be omitted in various examples. The remote monitoring system 120 can be implemented on and/or accessed by one, or more than one computing device, such as a desktop, laptop, or other computing device (for example, mobile phone or tablet). The remote monitoring system 120 can include and/or be configured to interact with one or more servers. The remote monitoring system 120 can allow interaction, communication, monitoring, among other things, via a mobile and/or web application (for example, via a browser) of information received from one or a plurality of user computing devices (such as user computing device 106, 118) and/or connectivity hubs 108, 118. For example, by way of non-limiting examples, the remote monitoring system 120 can allow for interaction, communication, monitoring with one, two, three, four, five, six, seven, eight, nine, or ten or more, between 1 and 5000, between 1 and 2000, between 1 and 1000, 1 and 500, 1 and 200, 1 and 100, 1 and 50, or 1 and 20 user computing devices, connectivity hubs, wearable devices, and/or users, or any number within these ranges or bounded by any range including any value within these ranges. The remote monitoring system 120 can be implemented across one, or more than one location. The remote monitoring system 120 and/or components thereof can be implemented by one or more virtual machines implemented in a hosted computing environment. The hosted computing environment may include one or more rapidly provisioned and/or released computing resources. The computing resources may include hardware computing, networking and/or storage devices configured with specifically configured computer-executable instructions. Hosted computing environments can be referred to as "cloud computing" environments. The remote monitoring system 120 can be utilized and/or accessed by one or more computing devices, for example, by a monitor user of the organization via an application (e.g., web and/or mobile) usable on a computing device (e.g., desktop, laptop, smartphone, tablet).

Remote monitoring system 120 can include a network management module 402. The network management module 402 can manage network communications with other networks, including networks in organizations (e.g., offices, school, hospitals) as well as communications with user computing devices and/or connectivity hubs. Remote monitoring system 120 can also include one or more information database(s) 404 that can generally store data received from any of the user computing devices 106, 116 and/or connectivity hubs 108, 118 and/or directly received from any of wearable devices 102, 112. Such information stored in database(s) 404 can be any information received from the user computing devices 106, 116, connectivity hubs 108, 118, and/or wearable devices 102, 112, including but not limited to health-related information and/or other information such as that discussed herein.

A monitoring portal 406 of the remote monitoring system 120 can provide a user interface or user interfaces that can be accessed by users associated with the organization via a computing device (for example, a mobile phone, tablet, desktop, or laptop). For example, monitoring portal 406 of the remote monitoring system 120 can provide a user interface that can be accessed by a monitor user of the organization. Such "monitor user" can be a user or users affiliated with the organization who are tasked with monitoring and/or managing aspects of the remote monitoring system 120, for example, monitoring health-related information associated with user of the organization, viewing and/or modifying exposure levels and/or risk states of the users in the organization, sending notifications and/or instructions to users in the organization, among other things. The monitoring portal 406 may, for example, be implemented in one or more web pages, mobile applications, or other network applications and may provide information including and/or associated with the information received from the user computing devices 106, 116, connectivity hubs 108, 118, and/or wearable devices 102, 112. For example, the monitoring portal 406 can display health-related information, exposure levels, and/or risk states of one or more users, each of which are discussed in more detail elsewhere herein.

Remote monitoring system 120 can include a user profile manager 408. The user profile manager 408 can manage user profiles, which can include information about user demographics, user notification (e.g., alarm) settings, user conditions and so forth. Remote monitoring system 120 can additionally or alternatively include a device profile manager 410 that can manage and store device profiles for wearable devices and/or user computing devices that interact with the remote monitoring system 120 as well as optionally other computing devices. In some implementations, the user profile manager 408 allows configuration, creation, and/or management of groups within the organization, such as the groups discussed below with respect to various exemplary user interfaces.

Remote monitoring system 120 can include a notification system 412. The notification system 412 can issue notifications to user computing devices 106, 116, such as alerts of exposure to infections and/or instructions (for example, "quarantine for 7 days", "do not come into the office"). Such notification system 412 can be configurable by the organization, for example, by monitor users of the organization. For example, the notification system 412 can be configurable to enable the notification discussed with respect to the user interface 1207 in FIG. 12F below.

In some implementations, the remote monitoring system 120 can include an information exchange system 414 that can facilitate communicating information about users to government or research institutions. One scenario where user information may be submitted (anonymously) to government or research institutions is where a disease outbreak has occurred within an organization.

Remote monitoring system 120 can receive health-related and other information from a plurality of user computing devices 106, 116, connectivity hubs 108, 118, and/or wearable devices 104, 114 and can store such received information in one or more user databases 404. Example health-related information can be any of that discussed herein, including, without limitation: physiological information of one or more users; information related to proximity of the user to one or more (or a plurality of) other users (for example, for determination of contact tracing and/or exposure to potential infections and/or diseases); information and/or data related to a user's diagnosis and/or test result(s) with respect to one or more infections and/or diseases (e.g., positive and/or negative test results, diagnosis obtained from a medical professional); and information and/or data related to symptom(s) experienced by the user (which can be input by the user into a computing device operated by a user, for example). Exemplary physiological information, which can be measured by the wearable devices 104, 114 can be any of that discussed herein, including but not limited to temperature, blood pressure, pulse rate, heart rate, respiratory rate (RRa), total hemoglobin (SpHb®), carboxyhemoglobin (SpCO®), methemoglobin (SpMet®), oxygen content (SpOC™), oxygen saturation (SpO2), pulse rate (PR), perfusion index (Pi), pleth variability index (PVi®), electroencephalogram (EEG) data, trending values of the same or combinations of the same, wellness indexes, or the like.

Remote monitoring system 120 can receive health-related and/or other information from a plurality of users in an organization and can be configured to determine various exposure levels and/or risk states of any of the plurality of users based on such received information. With continued reference to FIG. 4, remote monitoring system 120 can include a contact tracing engine 416 and a risk engine 418. The contact tracing engine 416 can receive contact tracing data from one or more user computing devices 106, 116, connectivity hubs 108, 118, and/or wearable devices 104, 114. Such contact tracing data can include any information and/or data that may be associated with, representative of, and/or indicative of a user's (physical) proximity to one or more (or a plurality of) other users (e.g., within a proximity threshold as discussed herein), for example.

The contact tracing engine 416 and/or risk engine 418 can receive other information that may be related to such proximity data from one or more databases 404 forming part of or accessible to the remote monitoring system 120. For example, such other information that may be related to such proximity data can include, without limitation: a duration of time that a user is within proximity (for example, with a proximity threshold) to one or more (or a plurality of) other users, a number of times (e.g., events) where a user is within proximity to one or more (or a plurality of) other users over a given period or time (e.g., 5 days, 7 days, 10 days, 14 days, 30 days, etc.); and/or and health-related information of any of such one or more other users that such user was within proximity of (e.g., a risk state of any of such one or more other users).

Additionally or alternatively, the contact tracing engine 416 and/or risk engine 418 can receive such other information that may be related to such proximity data from one or more user computing devices 106, 116, connectivity hubs 108, 118, and/or wearable devices 104, 114.

The contact tracing engine 416, which is described in more detail further below, can keep track of locations and/or interactions of any of the plurality of users in the organization and determine potential exposure(s) that any of such users had to users who may be infected with an infectious disease (e.g., COVID-19) over a period of time. As will be discussed in more detail below, the contact tracing engine 416 can advantageously allow the remote monitoring system 120 to send notifications and/or instructions to any user in the organization related to determinations made by the contact tracing engine 416 and/or risk engine 418, such as notifications that a particular user was within a threshold proximity (e.g., 100 ft, 50 ft, 20 ft, 6 ft) of a user during some time period who was confirmed for an infectious disease, for example, within that same time period.

The risk engine 418, which is described in more detail below, can be configured to calculate a risk state (which also be referred to herein as a "risk level") associated with any or all of the users of an organization associated with the remote monitoring system 120. Such risk state can be representative of and/or indicative of a user's risk or likelihood of having one or more infections. By way of non-limiting example, the risk engine 418 can determine if a user falls under one of four risk categories that is associated with the user's likelihood of being infected with a disease or illness, for example, COVID-19. The risk engine 418 can determine a risk state of any or all of a plurality of users within an organization based on a variety of information, including but not limited to physiological information of one or more users (such as that discussed elsewhere herein), contact tracing data (such as proximity data with one or more other users, accumulation durations of time of proximity with other users, risk states of other users who were in proximity to the user, etc.), information and/or data related to a user's diagnosis and/or test result(s) with respect to one or more infections and/or diseases (e.g., positive and/or negative test results, diagnosis obtained from a medical professional), and/or information and/or data related to symptom(s) experienced by the user (which can be input by the user into a computing device operated by a user, for example).

Figure 5A:
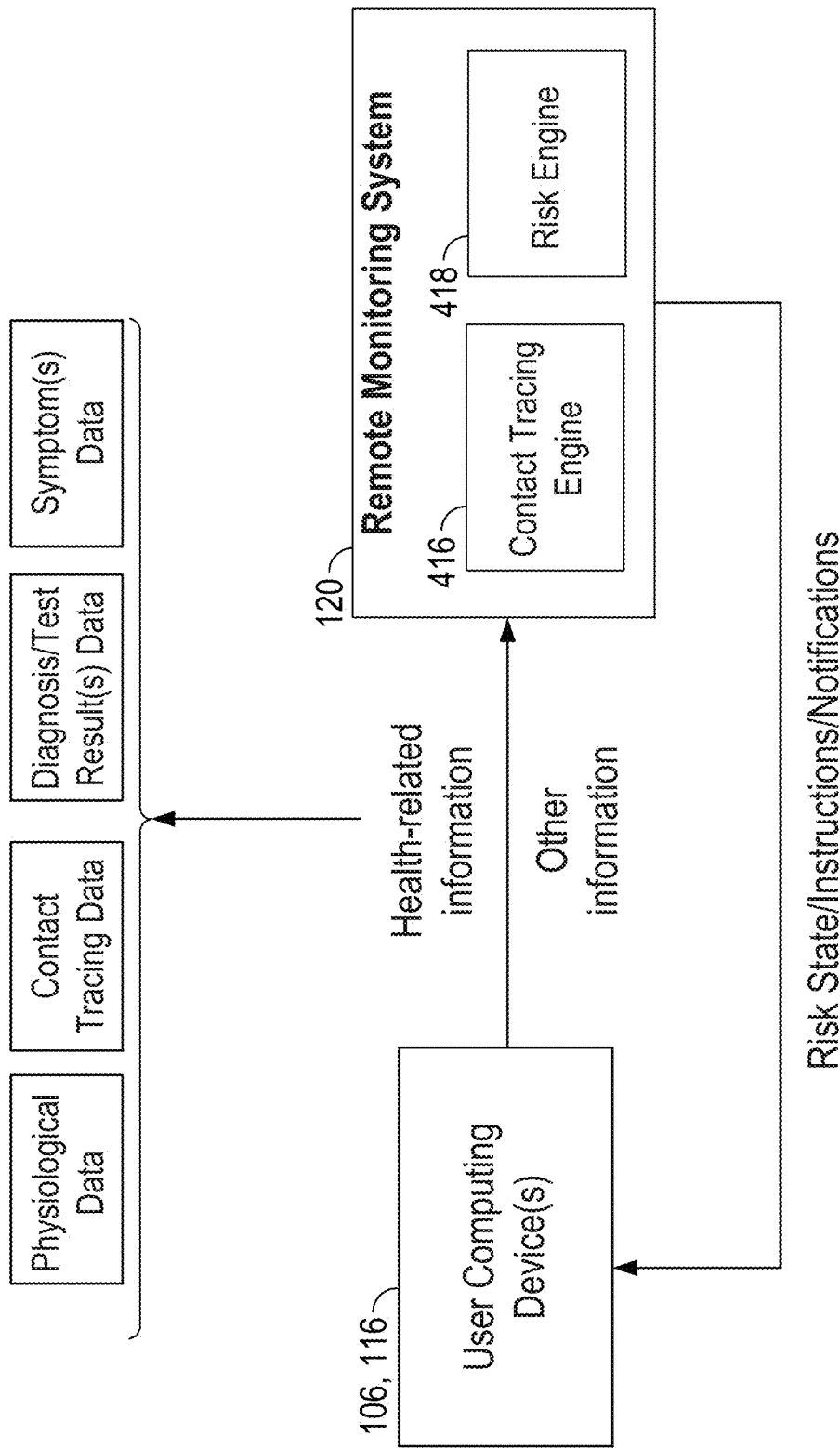
FIG. 5A illustrates exemplary interactions between one or more user computing devices and a remote monitoring system in accordance with aspects of this disclosure.

FIG. 5A illustrates, in a simplified form, how user computing devices 106, 116 can interact with remote monitoring system 120, and in particular, with the contact tracing engine 416 and the risk engine 418. As illustrated and as discussed previously, any or all of a plurality of user computing devices 106, 116 associated with (for example, employees of) and organization can transmit health-related information and/or other information such as that discussed above to the remote monitoring system 120. The contact tracing engine 416 and risk engine 418 can carry out the functions discussed above and elsewhere herein, and the remote monitoring system 120 can transmit various information back to one or more of the plurality of user computing devices 106, 116, for example, simultaneously. Such information transmitted to the one or more of the plurality of user computing devices 106, 116 can include, among other things, a risk state of a user associated with the user computing device 106, 116, instructions that may be related to such risk state (e.g., instructions to avoid coming into the organization's facilities or to quarantine a certain amount of time), and/or notifications such as exposure to other users who may be confirmed as having a particular infection.

Figure 5B:
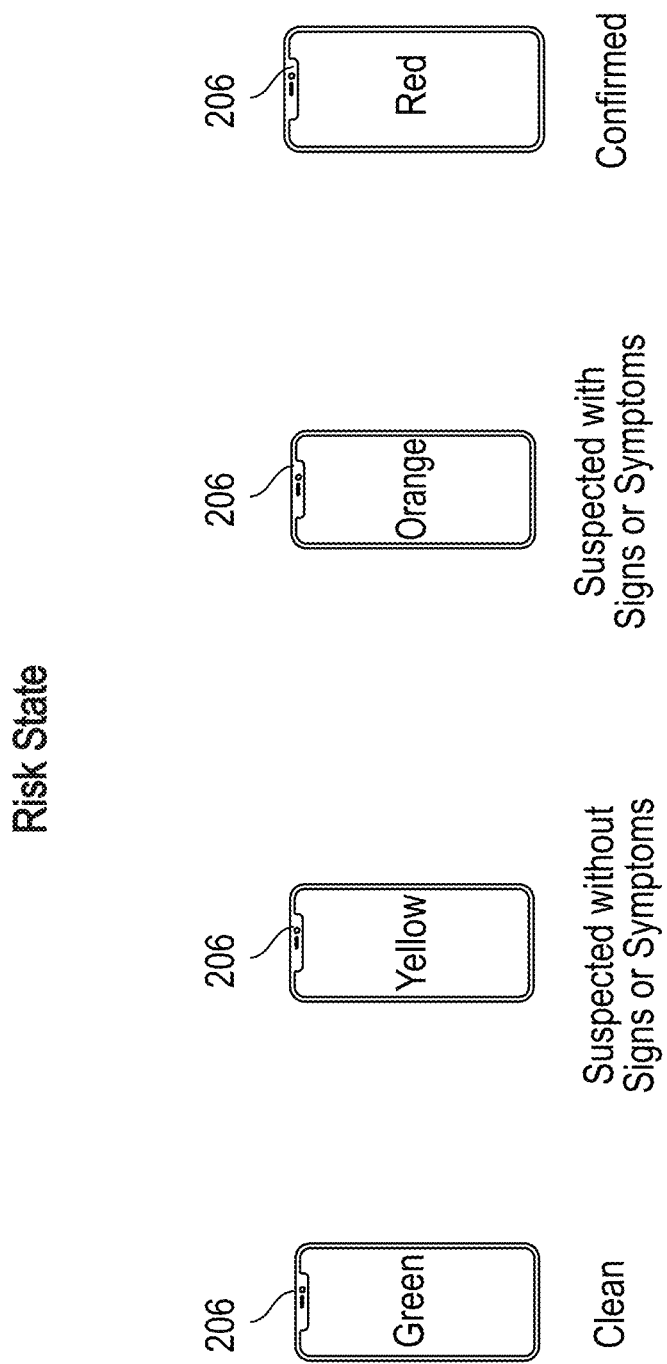
FIG. 5B illustrates exemplary risk states in accordance with aspects of this disclosure.

FIG. 5B illustrates exemplary risk states that can be determined and/or transmitted by the remote monitoring system 120 to user computing devices 206 associated with users. While FIG. 5 illustrates mobile phones (smart phones) as user computing devices 206, any other type of computing device can be used as discussed elsewhere herein. Accordingly, the discussion below with respect to risk states being sent to and/or displayed on user computing devices 206 is equally applicable to any of the user computing devices discussed herein.

With reference to FIG. 5B, risk states determined and transmitted by the remote monitoring system 120 to the user computing devices 206 can be: "Clean" or "Negative" or "No risk" which can represent that a user does not have and/or is not at risk for having a particular infection and/or that the user is at no or low risk to infect others with the infection; "Suspected without signs or symptoms" which can represent that a user is suspected to have a particular infection (for example, based on contact tracing data in relation to other users who may be positive for the infection) but does not appear to currently have symptoms that may be associated with the particular infection; "suspected with signs or symptoms" which can represent that a user is suspected to have a particular infection (for example, based on contact tracing data in relation to other users who may be positive for the infection) and has one or more symptoms that may be associated with the particular infection; and/or "Confirmed" or "Positive" which can represent that a user does have a particular infection. Any of such risk states can be determined by the remote monitoring system 120 (for example, via the risk engine 418) based on one or more of physiological data, contact tracing data, diagnosis and/or test result data, and/or symptom(s) data, each of which are discussed elsewhere herein.

The user computing device 102 (for example, all or a portion of a user interface on the user computing device 206) may illuminate green to indicate that the user is unlikely to be infected. If the risk engine 135 determines that the user may be suspected of being infected but the user hasn't presented any symptoms, the user computing device 102 (for example, all or a portion of a user interface on the user computing device 206) may illuminate yellow. If the risk engine 135 determines that the user may be showing symptoms and may be suspected of being infected, the user computing device 102 (for example, all or a portion of a user interface on the user computing device 206) may illuminate orange. The user computing device 102 (for example, all or a portion of a user interface on the user computing device 206) may illuminate red to indicate that the user is confirmed to be infected.

With reference to FIG. 5A-5B, the remote monitoring system 120 can send such risk state(s) and/or instructions or notifications associated with such risk states to user computing devices 106, 116. The user computing devices 106, 116 can be configured to display, for example, on a display thereof, the risk states and/or instructions or notifications associated with such risk states. For example, the user computing devices 206 can illuminate, for example, a portion or an entirety of a graphical user interface on a display thereof, a certain color which can be associated with said risk states. For example, as illustrated, the user computing device 206 can be configured to illuminate (e.g., flash): a green color associated with the "Clean" or "Negative" or "No risk" which is described above; a yellow color associated with the "Suspected without signs or symptoms" which is described above; an orange color associated with "Suspected with signs or symptoms" which is described above; and/or a red color associated with "Confirmed" or "Positive" which is described above. In some implementations, the remote monitoring system 120 can send instructions to the user computing device 106, 116 to enable a processor of the user computing device 106, 116 to execute an application to cause display of any of such risk state visual representations on all or a portion of a graphical user interface of the user computing device 106, 116.

In some configurations, the user computing device 106, 116 can be configured to communicate with an external device to cause the external device to emit a visual and/or audio notification representative of these above-described risk states. For example, the user computing device 106, 116 may be configured to communicate with a nametag or other device that is configured to emit such visual and/or audio notifications. Such an exemplary nametag or other device can include suitable electronic hardware and/or software to enable communication with user computing device 106, 116 and emission of such visual and/or audio notifications. For example, such nametag or other device can include a processor, a wireless transceiver configured to communicate with the user computing device 106, 116 over any of the communication protocols discussed herein (such as Bluetooth® and/or NFC), one or more light emission sources (such as light emitting diodes (LEDs)) configured to illuminate the color that corresponds to the user's risk state, one or more audio devices configured to emit a sound and/or phrase associated with the risk state, and a power source configured to power these components (for example, a battery).

As an example, if the risk engine 418 determines a user is in an "orange" category (see above discussion), the remote monitoring system 120 can communicate such information to the user computing device 106, 116 and the user computing device 106, 116 can communicate with a separate electronic nametag associated with (and/or coupled to) the user to instruct the nametag to cause the LEDs to illuminate orange. The illuminated nametag can advantageously allow an employer, for example, to quickly screen large numbers of employees in a short period of time, for example, before they enter a workplace. As another example, such illuminated nametag can allow a sports or concert venue to similarly screen large numbers of guests before allowing them into the venue.

User computing device 106, 116 can communicate with an electronic device different than such exemplary nametag discussed above in a similar manner. For example, use computing device 106, 116 can communicate information and/or instructions associated with such risk states to an electronic screening device such as a handheld wand or walkthrough screening device which can have similar electronic components and/or functionality as that discussed above with reference to the nametag. Such handheld wand or walkthrough screening device can be configured to notify a screener (for example, a person associated with the organization) of a user's risk state. When the user computing device 106, 116 (and/or user associated such computing device 106, 116) is in sufficient proximity with the handheld wand or walkthrough screening device, the user computing device 106, 116 can instruct the handheld wand or walkthrough screening device to illuminate the color associated to the user's risk state (such as "green", "yellow", "orange", or "red" as discussed above with reference to the described risk states).

In some scenarios, for example, where the remote monitoring system 120 is operated and/or monitored by a third party not directly affiliated with the organization to whom the users 102, 112 belong, the remote monitoring system 120 can be configured to automatically send a notification to the organization (for example, a particular employee tasked with monitoring the system 120) if a user's risk state is in a certain category (for example, "yellow", "orange", or "red"). In such cases the organization can then make a determination of whether to allow the user to come into the a facility of the organization. In some situations, the organization can utilize the remote monitoring system 120 to send instructions (for example, via a message) to the user to instruct the user to not come into the facility. In other scenarios where the organization (for example, a particular employee tasked with monitoring the system 120) directly monitors or implements (for example, without the use of a third party) the system 120, the organization may initiate the sending of such instructions to the user.

Figure 6A:
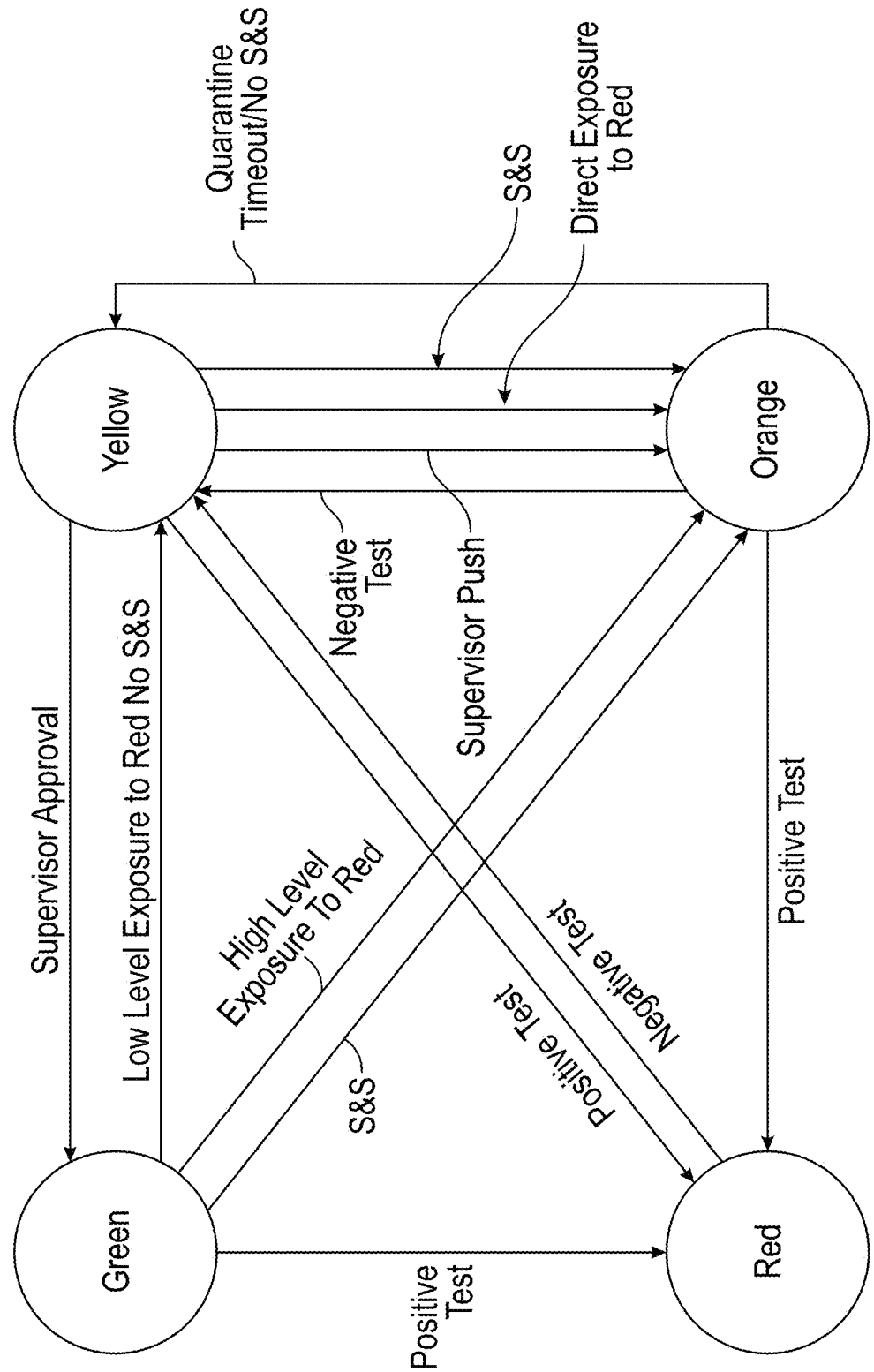
FIG. 6A-6B illustrate exemplary diagrams showing how one or more risk states can be determined and/or modified in accordance with aspects of this disclosure.

FIG. 6A shows an exemplary diagram which illustrates how the remote monitoring system 120 can be used to determine and/or adjust risk states for various users associated with an organization. Advantageously, the remote monitoring system 120 can dynamically determine risk state(s) of various users based on health-related information and/or other information continuously received from the user computing devices 102, 112 and/or the wearable devices 104, 114. As discussed above, the remote monitoring system 120 can receive sets of health-related information including physiological data from one or more wearable devices coupled to each of a plurality of users and other data. Such physiological data can be analyzed by the risk engine 418 to determine risk state(s). Additionally, as discussed previously, contact tracing data, diagnosis or test result data, and/or symptoms information, such as any of that described herein, can be received by the remote monitoring system 120 from the user computing devices 102, 112 and/or the wearable devices 104, 114 and can be utilized to determine risk state(s).

Figure 6B:
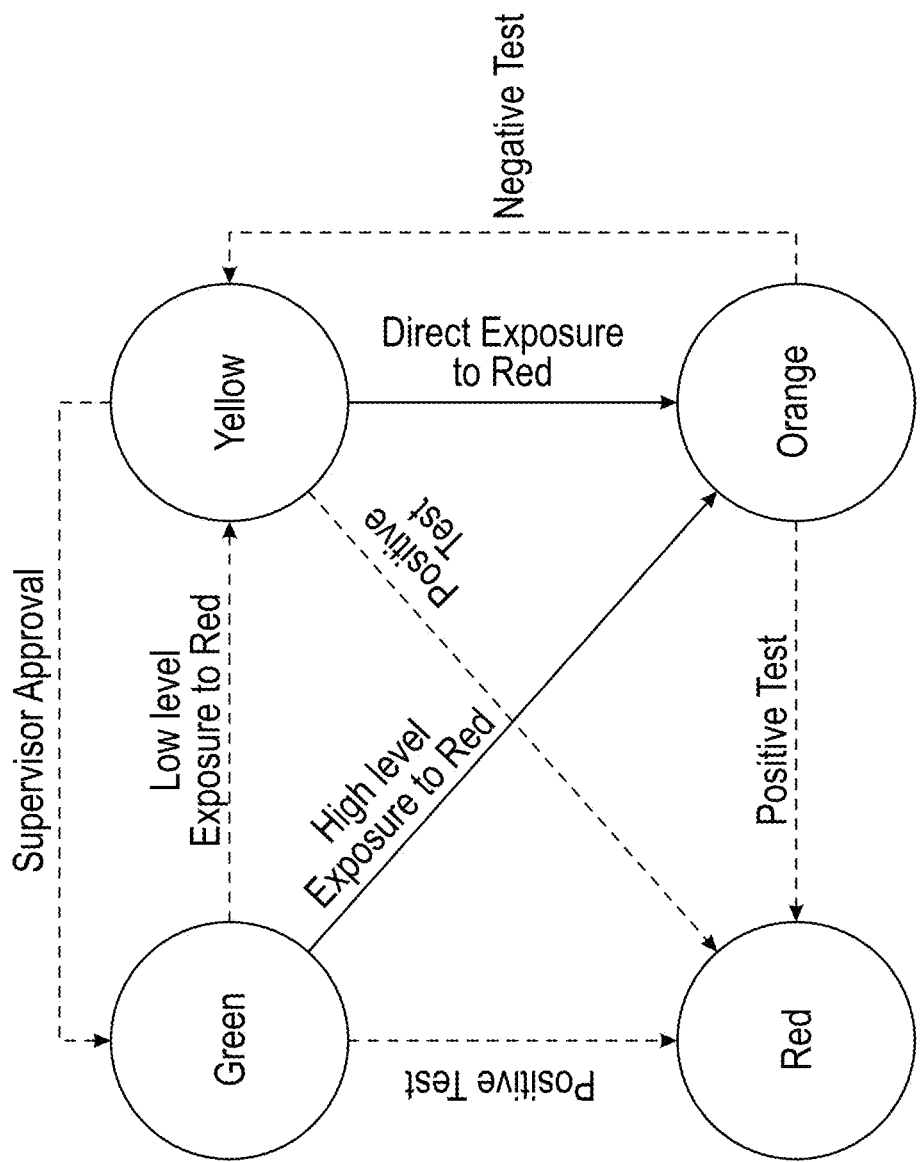

With reference to the exemplary diagrams of FIGS. 6A-6B, the remote monitoring system 120 (via the risk engine 418) can determine the risk state of a user based on test results (for example, inputted by a user into the user's computing device and sent to the remote monitoring system 120), exposure to one or more other users who have been determined have a certain risk state (for example, "red"), experienced symptom(s) (for example, which are inputted by a user into the user's computing device and sent to the remote monitoring system 120), among other things. For example, the remote monitoring system 120 (via the risk engine 418) may automatically determine a user is in the red category (which can be indicative of the user being "Confirmed" for an infection) based on a positive test result to a particular infection (e.g., COVID-19). As another example, the remote monitoring system 120 (via the risk engine 418) may automatically determine the user is in the yellow category based on a negative test result, low level exposure to another user who was determined to be in the red category, the user quarantining for a required amount of time, and/or the user not experiencing symptoms of the particular infection. As another example, the remote monitoring system 120 (via the risk engine 418) may automatically determine that a user is in the orange category based on high-level of exposure to a user who was determined to be in the red category and/or the user experiencing symptoms of the infection. FIGS. 6A-6B also illustrate how signs or symptoms can be used by the risk engine 418 to adjust a risk state (see "S&S" in FIG. 6A). Such automatic determination by the remote monitoring system 120 (via risk engine 418) allows for efficient and continuous monitoring and/or management of up to a vast amount of users and brings significant improvements to conventional approaches at limiting a spread of an infection at an organization.

Advantageously, the remote monitoring system 120 can be configured to allow manual adjustments and/or modifications to risk states by the organization, for example, based on other factors. For example, a monitor user tasked with monitoring the system 120 for an organization may manually change a risk state of a given user based on standards and/or guidance of the organization and/or of the monitor user. Such action is represented in FIGS. 6A and 6B as "Supervisor Approval" and "Supervisor Push" and can represent a monitor user "approving" a certain risk state for a certain user (for example, in response to a user's request) and "pushing" the user's risk state to another risk state. Such action can accordingly allow, for example, the employee to gain access to a facility of the organization. For example, such manual adjustment can be utilized to change a user's risk level from orange to yellow, yellow to orange, and/or yellow to green (see FIGS. 6A-6B).

The remote monitoring system 120 can be configured to automatically change a user's risk state based on contact tracing data. For example, as indicated by the solid arrows in FIGS. 6A-6B, certain events/factors related to contact tracing can automatically change the risk state of a user. For example, in some implementations, if the contact tracing engine 416 determines a first user in the green category had a low level exposure to a second user in the red category (e.g., the first and second user were a far distance apart for a short period of time), then the first user's risk state can automatically be changed to yellow. As another example, in some implementations, if the contact tracing engine 416 determines that a first user in the yellow category had a medium exposure to a second user in the red category (e.g., the first and second users were a medium distance apart for a medium period of time), then the first user's risk level can automatically be changed to orange. As another example, in some implementations, if the contact tracing engine 416 determines that a first user in the green category had a high level exposure to a second user in the red category (e.g., the first and second users were in close proximity for a long period of time), then the first user's risk level can automatically be changed to orange. Any of such terms "far", "medium", "close" can be represented by the values discussed elsewhere herein, for example, with respect to FIGS. 3A-3B and/or FIG. 7B.

As discussed above, a user's risk level may be manually changed by an assigned person of associated with the organization, such as the user, a manager, or a teacher. For example, an employer may assign certain screening roles to certain people in the organization. A senior employee may be assigned to be an initial screener with limited approval capabilities. For example, the senior employee may be able to clear an employee in the yellow category to be in the green category. However, the senior employee may not be able to clear an orange category. A manager or an administrator can be assigned to be a screener with more approval capabilities than the initial screener. For example, the administrator can clear an employee in the yellow or orange category to be in the green category. For employees in the red category, an authorized caregiver may be required to clear the employee to return to work.

In some implementations, the remote monitoring system 120 (for example, the risk engine 418) may require the employer's approval before changing a user's risk state from one category, such as the yellow category, to another category, such as the green category. In some aspects, the employer may change and/or allow the change of a user's risk state from the yellow category to the orange category.

Any or all of the health-related information and/or other information received by the remote monitoring system 120 from the user computing devices 106, 116 (or directly via the wearable devices 104, 114) can be stored in one or more database associated with the remote monitoring system 120, for example, database(s) 404. Additionally, any or all of the exposure levels and/or risk states determined by the remote monitoring system 120 can be stored in such databases or different databases. The remote monitoring system 120 (for example, via the contact tracing engine 416 and/or risk engine 418) can determine exposure levels and/or risk states of one or more users every 30 seconds, 1 minute, 2 minute, 5 minutes, 10 minutes, 20 minutes, 30 minutes, 1 hour, 2 hour, 3 hours, 6 hours, once per day, once per week, etc. Additionally or alternatively, the remote monitoring system 120 can be configured to determine exposure levels and/or risk states of one or more users at any point upon request from a user 102, 112 (for example, via user computing device 106, 116) and/or a monitor user monitoring the system 120. For example, in some implementations, an authorized user of the organization can request a report of all the individual risk states of the users associated with the organization. For example, an employer who owns a warehouse may want to monitor the employees' individual risks of being infected with COVID-19. The remote monitoring system 120 can be utilized to produce a report for the employer, which shows the risk state for each of the employees.

Contact Tracing

As discussed above, the remote monitoring system 120 (for example, via risk engine 418) can determine one or more users risk states based on, among other things, contact tracing data. Such contact tracing data can include without limitation: any information and/or data that may be associated with, representative of, and/or indicative of a user's (physical) proximity to one or more (or a plurality of) other users (e.g., within a proximity threshold as discussed herein); a duration of time that a user is within proximity (for example, with a proximity threshold) to one or more (or a plurality of) other users; a number of times (e.g., events) where a user is within proximity to one or more (or a plurality of) other users over a given period or time (e.g., 5 days, 7 days, 10 days, 14 days, 30 days, etc.); and health-related information of any of such one or more other users that such user was within proximity of (e.g., a risk state of any of such one or more other users).

Figure 7A:
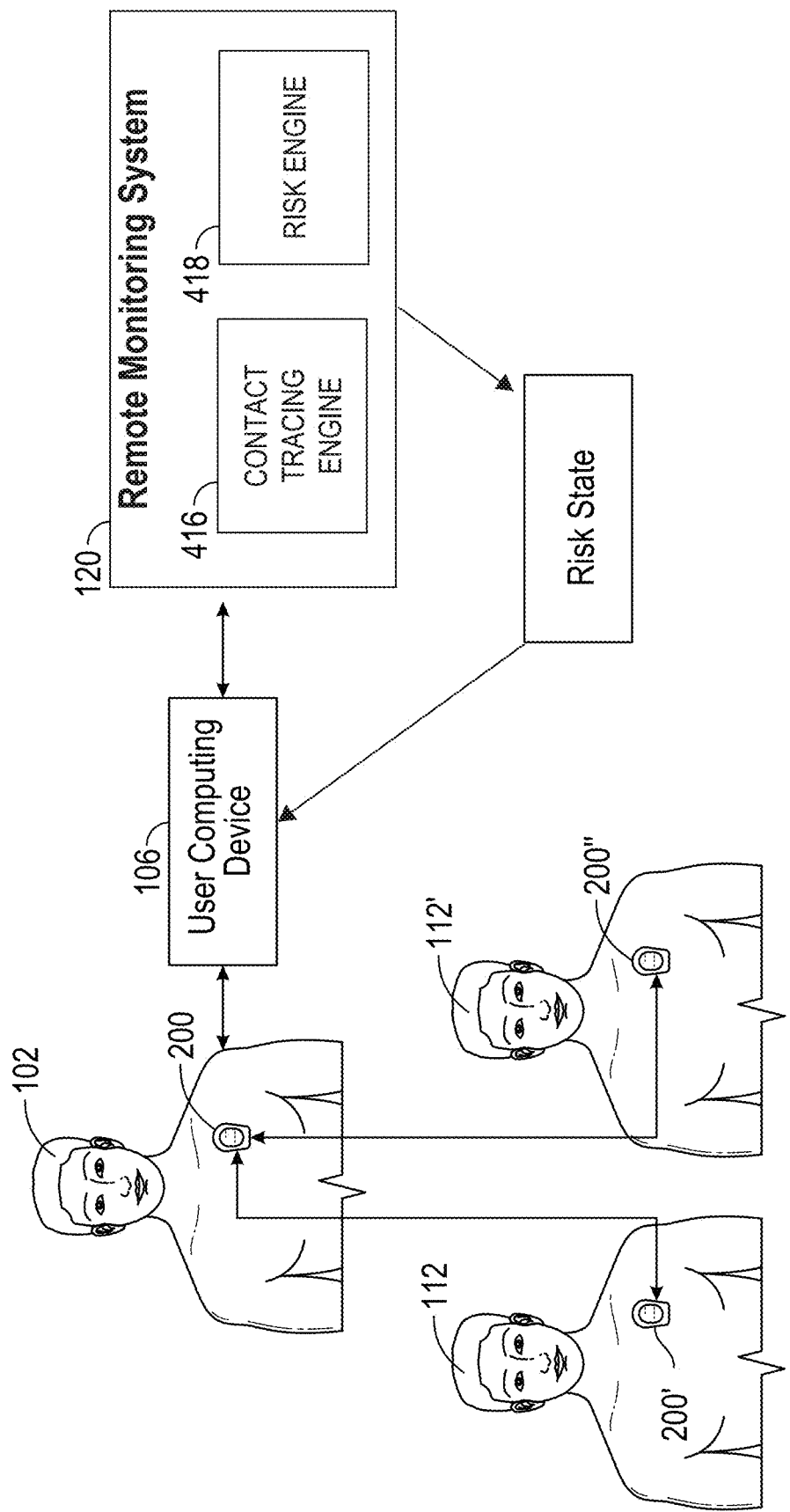
FIG. 7A illustrates exemplary interactions between one or more wearable devices, a user computing device, and a remote monitoring system in accordance with aspects of this disclosure.

FIG. 7A illustrates a user 102, a wearable device 200 coupled to user 102, a user 112, a wearable device 200' coupled to user 112, a user 112', and a wearable device 200" coupled to user 112' which can be identical to the wearable devices 200, 200' discussed previously. Although FIG. 7A illustrates one wearable device 200, 200', 200" coupled to the user 102, 112, 112', as discussed previously, any number of wearable devices of same or different type can be coupled to the user 102, 112, 112' and can operate as described below and elsewhere herein. Such wearable devices 200, 200', 200" can be the same in some or all respects as any of the wearable devices discussed herein. Additionally, the discussed below with respect to any of wearable devices 200, 200', 200" is equally applicable to any of the wearable devices discussed herein (such as wearable devices 104, 114). Additionally, the discussed below with respect to user computing device 106 is equally applicable to any of the other user computing devices discussed herein.

As discussed previously, wearable device 200 can be configured to detect proximity to one or more other wearable devices coupled to one or more other users. For example, wearable device 200 can be configured to detect proximity form wearable device 200' and/or 200" simultaneously or non-simultaneously, based on detected signal strength between the devices 200', 200" and the wearable device 200. The wearable device 200 can wirelessly communicate with wearable devices 200', 200" over any wireless communication protocol such as those discussed herein and signals transmitted and/or received over such protocols can be used for such proximity detection. Additionally, wearable device 200 can be configured to receive and/or transmit identifier(s) between wearable devices 200', 200' which can be associated with the users 112, 112'. Such information is advantageous as it allows the wearable device 200, and an associated user computing device 106, to keep track of each user that comes into proximity with user 102 over various time periods, as well as keeping track of actual proximity values (e.g., distances).

Figures 7B, 7C:
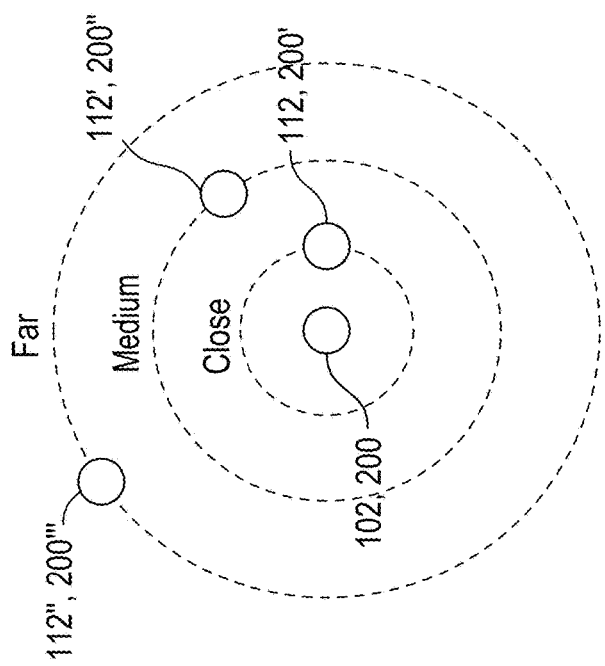
FIG. 7B illustrates a diagram indicative of proximity data of one or more users in accordance with aspects of this disclosure.
FIG. 7C illustrates an exemplary contact tracing table in accordance with aspects of this disclosure.

In some configurations, wearable device 200 can detect proximity values when the wearable devices 200', 200" are within some threshold proximity, as discussed above (e.g., within 200 ft, 100 ft, 50 ft, 30 ft, 20 ft, 15 ft, 10 ft, 6 ft, 3 ft etc.) and can transmit such information to the user computing device 106 at various time intervals (e.g., every second, every 3 seconds, every 5 seconds, every 30 seconds, every minute, every 2 minutes, every 5 minutes, every 10 minutes, every 30 minutes, every hour, etc.). In some implementations, wearable device 200, user computing device 106, and/or remote monitoring system 120 categorizes a user's 102 proximity to one or more other users (such as user 112, 112'). For example, in some implementations, wearable device 200, user computing device 106, and/or remote monitoring system 120 categorizes a user's proximity to user 112, 112' as "far", "medium", and/or "close" based on one or more proximity values determined between the wearable devices 200, 200', 200", as illustrated in FIG. 7B. With reference to FIG. 7B, the "far" category can be between about 20 ft and about 200 ft, between about 20 feet and about 100 feet, between about 20 feet and about 50 feet, between about 30 ft and about 200 ft, between about 30 feet and about 100 feet, between about 30 feet and about 50 feet, or any number within these ranges or bounded by any range including any value within these ranges. The "medium" category can be between about 10 ft and about 50 ft, between about 10 ft and about 40 ft, between about 10 ft and about 30 ft, between about 10 ft and about 20 ft, between about 10 ft and about 15 ft, or any number within these ranges or bounded by any range including any value within these ranges. The "close" category can between about 6 inches and about 20 ft, between about 1 ft and about 20 ft, between about 1 ft and about 15 ft, between about 1 ft and about 10 ft, between about 1 ft and about 6 ft, within 20 ft, within 15 ft, within 10 ft, within 6 ft, within 3 ft, or any number within these ranges or bounded by any range including any value within these ranges.

In some cases, the wearable device 200 and/or wearable devices 200', 200" are configured to communicate over only one wireless communication method or protocol so as to limit or prevent communication with other devices or systems. In some cases, the wearable device 200 and/or wearable devices 200', 200" are configured to communicate only with authorized devices (such as authorized user computing devices) and/or the remote monitoring system 120. In one example, the wearable devices 200, 200', 200" can be configured to detect only Bluetooth® signals from other wearable device(s) or other designated devices. Such configurations can enable the wearable device(s) to more easily track other wearable devices by limiting interferences from devices outside the system and/or prevent inadvertent tracking of devices outside the system. Such configuration can also advantageously improve battery life of the wearable devices by limiting the signals sent and received by the wearable devices.

With continued reference to FIG. 7A, the wearable device 200, user computing device 106, and/or remote monitoring system 120 can detect, register, and/or record a contact event when the wearable device 200 is within a threshold proximity to one or more other wearable devices (such as wearable device 200', 200"). Such threshold proximity can be, as discussed above, for example, 200 ft, 100 ft, 80 ft, 70 ft, 60 ft, 50 ft, 40 ft, 30 ft, 20 ft, 15 ft, 10 ft, 9 ft, 8 ft, 7 ft, 6 ft, 5 ft, 4 ft, 3 ft, 2 ft, 1 ft, or any value between any of these values, or any range bounded by any combination of these values, although values outside these values or ranges can be used in some cases. Such threshold proximity can be associated with the "far" distance threshold and the associate dotted circle illustrated in FIG. 7B, for example, or alternatively, can be represented by the "medium" or "close" dotted circles in FIG. 7B. In some cases a contact event can represent and/or be associated with an amount of time that two users were within the threshold proximity to one another. For example, a contact event can occur when two users are within 6 ft, 10 ft, or 15 ft from one another for a period of greater than 2 minutes, greater than 5 minutes, greater than 10 minutes, or greater than 15 minutes.

FIG. 7B illustrates an exemplary display (for example, that may be displayed on the user computing device 106 or a display associated with the remote monitoring system 120) showing proximity between user 102, wearable device 200 and other users 112, 112', 112" and wearable devices 200', 200", 200'''. As shown, user 112 and wearable device 200' are depicted as being a "close" distance from user 102 and wearable device 200, user 112' and wearable device 200" are depicted as being "medium" distance from user 102 and wearable device 200, and user 112" and wearable device 200''' are depicted as being a "far" distance from user 102 and wearable device 200.

In some implementations, the wearable device 200 can continuously detect and transmit proximity data (e.g., one or more proximity values) with one or more other wearable devices to user computing device 106 (and/or directly to remote monitoring system 120) when such wearable devices are within such threshold proximity. The user computing device 106 and/or the remote monitoring system 120 can keep track of the accumulated duration of time of such proximity for each respective pair of users, for example, until the pair of users are not within such threshold proximity. Additionally and/or alternatively, the user computing device 106 and/or the remote monitoring system 120 can keep track of the accumulated duration of time of such proximity over a period of time, for example, over a span of 1 day, 3 days, 5 days, 7 days, or 14 days. Detected proximity data and contact events can be transmitted by each of the wearable devices in any given pair that come within threshold proximity to each other and can be transmitted to user computing devices associated with such wearable devices and/or directly to the remote monitoring system 120.

The more time two or more wearable devices 200 are proximate to each other, the higher the risk that a given infection will be transmitted if one of the users associated with the wearable devices is positive and/or contagious. In some implementations, the user computing device 106 and/or the remote monitoring system 120 are configured to categorize a contact event, for example, by how much time a given user was within a threshold proximity of another user. For example, the user computing device 106 and/or the remote monitoring system 120 can categorize a contact event of any two users as a "short time period" or "short exposure" if such users were within a threshold proximity for less than or equal to 30 minutes, less than or equal to 20 minutes, less than or equal to 15 minutes, less than or equal to 10 minutes, less than or equal to 9 minutes, less than or equal to 8 minutes, less than or equal to 7 minutes, less than or equal to 6 minutes, less than or equal to 5 minutes, less than or equal to 4 minutes, less than or equal to 3 minutes, less than or equal to 2 minutes, less than or equal to 1 minute, less than or equal to 30 seconds, among other values and/or ranges. As another example, the user computing device 106 and/or the remote monitoring system 120 can categorize a contact event of any two users as a "medium time period" or "medium exposure" if such users were within a threshold proximity for between about 5 minutes and 30 minutes, between about 10 minutes and 25 minutes, between about 10 minutes and 20 minutes, between about 10 minutes and 1 hour, or any value therebetween or any range bounded by any value therebetween. As another example, the user computing device 106 and/or the remote monitoring system 120 can categorize a contact event of any two users as a "long time period" or "long exposure" if such users were within a threshold proximity for greater than or equal to 10 minutes, greater than or equal to 15 minutes, greater than or equal to 20 minutes, greater than or equal to 25 minutes, greater than or equal to 30 minutes, greater than or equal to 40 minutes, greater than or equal to 50 minutes, greater than or equal to 1 hour, between about 15 minutes and about 1 hour, between about 30 minutes and about 5 hours, between about 30 minutes and about 2 hours, among other values and/or ranges.

Exposure Level and Risk State Determinations

Remote monitoring system 120 (for example, via contact tracing engine 416 or risk engine 418) can be configured to determine a variety of metrics related to a user's exposure level to various other users (for example, associated with an organization) who may be or are infected with a communicable infection based on the above-described contact tracing data. A user's exposure level can include any information and/or data that may be associated with, representative of, and/or indicative of a user's exposure to one or more other users who may or may not be infected with a particular infection.

Remote monitoring system 120 can dynamically store, for each user associated with an organization, contact tracing data such as that described herein along with other health-related and other information, over time. Such contact tracing data can be indicative of all of the exposure (e.g., contact events) for each user, proximity data indicative of the distance(s) between each user and other users, and/or duration of time of each contact event and/or accumulated duration of contact time over a given time period (e.g., 3 days, 5 days, 7 days, 10 days, 14 days, etc.). In some cases, weight factors can be applied to contact events depending on the associated proximity(ies) values of such contact events and/or the duration of such contact events. In some cases, the remote monitoring system 120 can determine total number of users (in the organization) with confirmed infections and/or a ratio of confirmed infections over the total number of users.

There are a variety of ways that the remote monitoring system 120 can determine an exposure level of a user. For example, a user's exposure level can be determined based on (and/or can be indicative of) a summation, over a given time period (e.g., 3 days, 5 days, 7 days, 10 days, 14 days) of the time for each and every contact event with a user who was confirmed for the infection (e.g., in the "red" category described above) as described below with reference to Equations 1 and 2. With reference to Equation (1) below, $E_1$ can represent a summation of each contact event where a user was within a threshold proximity to an infected user multiplied by the time of such contact event. Such "threshold proximity" here can be any of the "far", "medium", or "close" categories discussed above or any of the other values discussed herein with respect to threshold proximity. As another example, such "threshold proximity" utilized in Equation 1 can be 20 ft, 15 ft, 10 ft, 6 ft, or 3 ft, for example.

$$E_1 = \Sigma_t \, \text{proximity} * \Delta t \qquad \text{(Equation 1)}$$

A user's exposure level (represented by $E_{total}$ in Equation 2 below) can be determined, as illustrated in Equation 2, by a summation of $E_1$ over all infected contacts over a period of time, for example.

$$E_{total} = \Sigma_{\text{\# of All Contacts}} \Sigma E_1 \qquad \text{(Equation 2)}$$

As another example, a user's exposure level can be determined based on (and/or can be indicative of) an average exposure with infected cases over a given period of time (e.g., 3 days, 5 days, 7 days, 10 days, 14 days). For example, as illustrated in Equation 3, the average exposure of a user can be determined based on an average of the exposure of $E_{total}$ discussed above in view of the total number of infected contacts (represented by "n" in Equation 3).

$$E_{average} = \frac{1}{n} \sum E_{total} \qquad \text{(Equation 3)}$$

As another example, a user's exposure level can be determined based on (and/or can be indicative of) a maximum amount of exposure the user has had with infected contacts over a given period of time (e.g., 3 days, 5 days, 7 days, 10 days, 14 days). For example, as illustrated in Equation 4, the maximum exposure of a user can be determined based on a maximum of the exposure of $E_{total}$ discussed above:

$$E_{maximum} = \max(\Sigma E_{total}) \qquad \text{(Equation 4)}$$

As another example, a user's exposure level can be determined based on (and/or can be indicative of) a number of contact events the user has had with infected users over a given period of time (e.g., 3 days, 5 days, 7 days, 10 days, 14 days) which exceeds a certain amount of time (for example, 3 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, or 1 hour). For example, the user's exposure level can be determined based on the number of times a user was within a threshold proximity (e.g., 6 ft) to an infected user for 15 minutes or more. As an example, such contact events can be defined as events where the user was within a threshold proximity that can be equal to any of the "far", "medium", or "close" categories discussed above, and/or can be equal to 20 ft, 15 ft, 10 ft, or 6 ft, for example.

In some cases, the remote monitoring system 120 can determine (for example, via the contact tracing engine 416) an exposure density of a group of users or all users in an organization, which can be the ratio of the number of infected users (i.e., users in the red category) to a total number of users in that group or organization. For example, an employer may want to monitor the exposure density of a subset of the organization, for example, that work in a particular office, facility, or building. In this scenario, the exposure density of the particular subset is the ratio of the number of infected employees/users to the total number of employees/users that within that subset.

The remote monitoring system 120 can determine (for example, via the contact tracing engine 416) exposure levels of users based on additional or alternative information. For example, information such as: whether a contact event was inside a large or small confined space or outside; ambient weather conditions (temperature being hot or mild, humidity, weather), and/or other information. The above described exposure levels can be modified based on such additional information.

In some cases, the remote monitoring system 120 can determine (for example, via the contact tracing engine 416) isolation levels of one or more users in the organization. Such isolation level can be defined by and/or representative of a total number of contact events (e.g., for a particular user) weight by proximity(ies) between users associated with the contact events.

Remote monitoring system 120 (for example, via contact tracing engine 416) can be configured to store information indicative of user exposure levels in one or more databases of the remote monitoring system 120. Such database(s) can be configured to store this data for a certain period of time. For example, the database(s) can be configured to automatically delete the data after one week, two weeks, three weeks, four weeks, 1 month, 2 months, or 6 months of storage.

Remote monitoring system 120 can be configured to maintain contact tracing table(s) and/or lists for each user associated with an organization that records various information related to the users. FIG. 7C illustrates an exemplary contact tracing table 702 that can be associated with a user in the organization. Such contact tracing table 702 can include a plurality of columns that can show: a timestamp of when a contact event occurred; a user or subject identifier of the other user involved in the contact event; a risk state of the other user; a distance between the user and the other user (i.e., between at least one wearable device coupled with each user); a proximity level of the contact event; a disease or infection state of the other user; and/or a quarantine state of the other user.

Such "Risk" column in table 702 can include values (e.g., numbers) that can represent a risk state of the user in a similar manner as that described herein with reference to the color coordinated risk states ("red", "green", "yellow", "orange"). Such risk state can be assigned and/or created by the organization to aid convenient categorization of infection risks of users of the organization. The "Proximity Level" column in table 702 can include values (e.g., numbers) that can represent a category of the proximity between users in a similar manner as that described above with reference to the categories "far", "medium", and "close". For example, a proximity level of "3" can be associated with proximity between users of between 1 ft and 6 ft and a proximity level of "2" can be associated with proximity between users of between 6 ft and 15 ft, between 6 ft and 20 ft, or between 6 ft and 30 ft, for example. In some cases, a proximity level of "0" can be associated with proximity between users of at least 15 ft, at least 20 ft, at least 30 ft, or at least 50 ft, for example.

The "Disease State" column in table 702 can reflect whether the other user has been confirmed to be infected or not with a particular infection. For example, the "Disease State" column in table 702 can have a "1" for users who have tested positive and/or have otherwise been determined to be positive for an infection and a "0" for users who have tested negative and/or are otherwise determined to be negative for an infection, or vice versa. The remote monitoring system 120 can dynamically update such table 702 over time simultaneously for a plurality of users in the organization as various types of information is received and/or determined by the remote monitoring system 120. The remote monitoring system 120 can dynamically update the table with external information or instructions (e.g., supervisor escalation or approval, positive or negative test results).

The "Quarantine State" column of table 702 can reflect whether a user is in a state of isolation from others. For example, a value of "1" in such column can reflect that the user is (or is supposed to be) in a state of quarantine from others, and a value of "0" in such column can reflect that the user is not in a state of quarantine from others, or vice versa.

Remote monitoring system 120 (for example, via risk engine 418) can determine a risk state of a user based on, at in part, exposure level determined for each user, which can itself be determined as described above. Other information that can be utilized by the remote monitoring system 120 (for example, via risk engine 418) to determine risk state includes, but is not limited to, physiological data of the users (such as any of that discussed above), symptom(s) information (such as any of that discussed above), and/or diagnosis and/or test result data (such as any of that discussed herein). In some implementations, remote monitoring system 120 generates, stores, and/or update (e.g., continuously over time), a contact tracing table (such as table 702) for every user associated with the organization (for example, every user in an organization including a plurality of users such as any of the numbers of users discussed herein). In some implementations, remote monitoring system 120 determines exposure levels for any or all users associated with the organization based on contact tracing tables associated with each user (such as table 702) alone or in combination with one or more of the exemplary methods listed above with respect to determining exposure levels (e.g., via any of Equations 1-4 and/or combinations thereof).

In some implementations, remote monitoring system 120 may be configured to execute certain administrative protocols or include certain features that are designed to avoid bias or retribution towards certain users. The protocols and/or features can also be configured to prevent manipulation by a user, such as an individual in the organization and/or a monitor user of the organization who is tasked with monitoring the organization's users over the remote monitoring system 120. At the start of a workday, for example, an employee can be required to present a screen with their user computing device 106 (e.g., smartphone) before entering a building of an organization. If the user computing device 106 is illuminated green, then the employee can be allowed into the building. If the user computing device 106 is not green, then the employer may request the employee to stay home to prevent the spread of a communicable disease. The user's user computing device 106 can be configured to present a unique daily barcode, which can be an encrypted version of the user's ID and the current date so the organization's remote monitoring system 120 can log in the employee. If a screener at the entrance to the building scans the barcode and there's an issue, then the remote monitoring system 120 can notify the screener. Thus, such unique daily barcode can help prevent an infected employee (i.e., an employee in the red category) from showing the screener a screenshot of a green screen from a different day and being allowed into the building. Such implementations can also advantageously be used in other types of settings, such as sports or concert venues.

As another example, a first user not infected with a communicable disease (e.g., COVID-19) and a second user infected with the disease may both spend at least some overlapping time in a subway station. In one example scenario, the first and second users were in the same station for a certain period of time. If the users stay a certain distance apart (such as six feet or more apart), as determined by wearable devices of the users (such as any of those discussed herein), then the risk state of the first user can remain green. If the users are in close proximity with one another (for example, within 6 ft) for a certain period of time (e.g., 5 minutes or more), then the risk state of the first user may change to yellow. In a second example scenario, the first and second users are in the same subway car. Since a subway car is more enclosed than a subway station, the first user's risk state may change to yellow if the two users are in the same subway car for a certain period of time (e.g., 5 minutes or more). In a third example scenario, the first and second users sat next to each other in the subway car. The first user's risk state may change to yellow in this scenario since the distance between the users is low. In a fourth example scenario, the second user was instead in the orange category and the first user's risk state was changed from green to yellow due to the first user's contact with the second user. If the second user later tested negative for the disease, then the first user's risk state may automatically change back to green. Such dynamic change of risk states of the users can be carried out as discussed above via the remote monitoring system 120, wearable devices, and user computing devices discussed herein.

Remote monitoring system 120 can be configured to notify users who may have come into contact with a user that is infected with the disease For example, a first user may have been infected with the disease and is in the red category. If the first user, for example, takes a flight, the system 110 can notify every user that was in proximity to the first user. For example, the system 120 can notify a second user that they shared a plane with a user in the red category (i.e., the first user) and/or change (e.g., automatically) the second user's risk state to the yellow category. This allows the second user to determine whether they should get tested, talk to their primary caregiver, quarantine themselves, inform others, stay home from work, etc.

Any of the user computing devices discussed herein can include one or more applications can be configured to execute various commands and/or operations which allow users to view their risk state and a plurality of other risks states of other users. For example, a user may be using a mobile or web application on their user computing device to find a restaurant nearby. The application can show the user which restaurants have the lowest risk based on the people currently at the restaurant. For example, a first restaurant may have five people in the red category and a second restaurant may have one person in the red category and four people in the yellow/orange categories. The application can indicate this, for example, by having a green, yellow, orange, or red indicator next to the restaurant. This added functionality allows a user to consider a restaurant's risk level when deciding on a place to eat at. In another example, a ride-sharing application may include a risk level based on the driver's risk level and/or the passengers' risk level. Users can set a minimum risk level threshold such that only drivers that are at or below the threshold can pick up the user. For example, a user can set the threshold to be yellow so that only drivers in green or yellow categories can pick them up. Additionally, drivers can set a minimum risk level threshold such that only riders with certain risk levels will appear on the drivers' application.

Example Methods

Figure 8B:
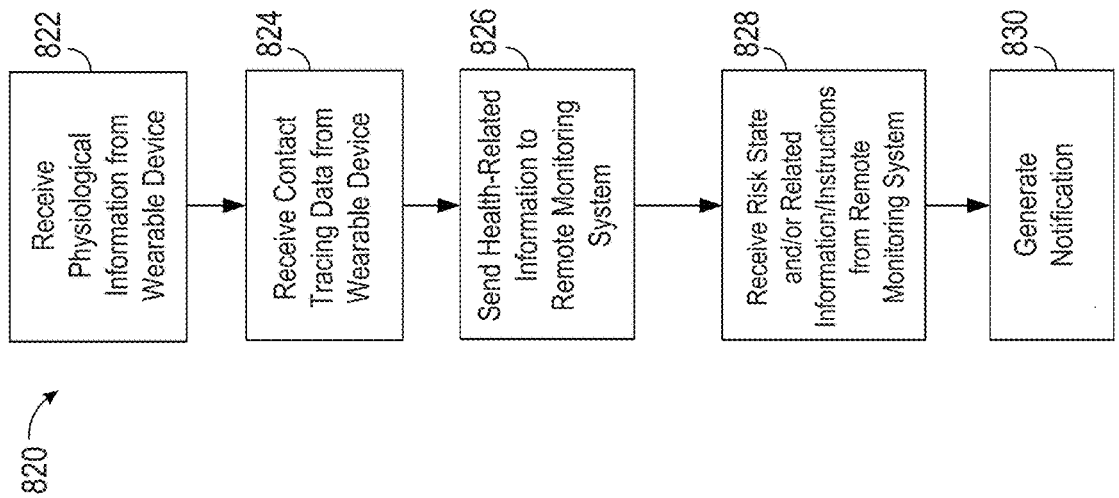
FIGS. 8A-8B illustrate exemplary methods of determining and receiving exposure levels and risk states.
Figure 8A:
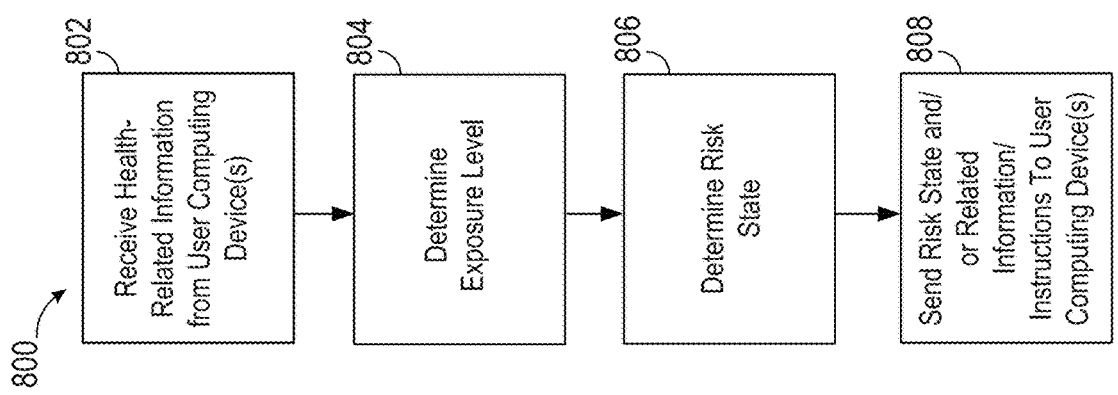

FIGS. 8A-8B illustrate exemplary methods 800, 820 by which the remote monitoring system 120, user computing device(s) 106, and wearable device 104 can interact to facilitate determination of an exposure level and/or risk state of one or more users associated with the remote monitoring system 120 (for example, associated with an organization utilizing a remote monitoring system 120).

With reference to the method 800 illustrated in FIG. 8A, at block 802, remote monitoring system 120 receives health-related information from one or more user computing devices. Remote monitoring system 120 can receive a plurality of sets of health-related information from a plurality of user computing devices associated with a plurality of users and a plurality of wearable devices that can be coupled to such plurality of users. One or more wearable devices (such as any of the wearable devices discussed herein) can be coupled and/or otherwise associated with each user to obtain physiological information and/or other information related to the user. A user computing device (such as any of the user computing devices discussed herein) of and/or used by the user can receive physiological and/or other information from the one or more wearable devices, for example, over any wired and/or wireless communication (such as any of the wireless communications protocols discussed herein).

Each user computing device can transmit (e.g., over a network) a set of health-related information to the remote monitoring system continuously and/or at various time intervals (e.g., every 30 seconds, every minute, every 2 minutes, every 5 minutes, every 10 minutes, every 20 minutes, every 30 minutes, every hour, every 2 hours, every day, etc.). Additionally or alternatively, in some implementations, wearable devices are configured to transmit health-related information directly to the remote monitoring system. Such set of health-related information can include any of that which is described elsewhere herein, including but not limited to: physiological information/data of a user; contact tracing data including information related to proximity of the user to one or more (or a plurality of) other users (for example, for purposes of determination of contact tracing and/or exposure to potential infections and/or diseases); information and/or data related to a user's diagnosis and/or test result(s) with respect to one or more infections and/or diseases which can be input by the user into the user computing device (e.g., positive and/or negative test results and/or diagnosis obtained from a medical professional); and information and/or data related to symptom(s) experienced by the user (which can be input by the user into a user computing device operated by a user, for example).

Physiological information/data of a user can be any of that discussed herein including, but not limited to, temperature, blood pressure, pulse rate, heart rate, respiratory rate (RRa), total hemoglobin (SpHb®), carboxyhemoglobin (SpCO®), methemoglobin (SpMet®), oxygen content (SpOC™), oxygen saturation (SpO2), pulse rate (PR), perfusion index (Pi), pleth variability index (PVi®), electroencephalogram (EEG) data, trending values of the same or combinations of the same, wellness indexes, or the like. Such physiological information can be derived from the user from one or more wearable devices when coupled to the user. Such physiological information/data can be indicative of an onset of symptoms experience by the user and which can be associated with one or more infections.

Contact tracing data can include any of that which is discussed elsewhere herein. Such contact tracing data can be indicative of physical proximity of the user to one or more other users which can be determined based on detected wireless signal strengths between one or more wearable device coupled to each of the user and the one or more other users. As discussed elsewhere herein, accumulated duration (s) of time where a user was within a threshold proximity to one or more other users (for example, any of the threshold proximities discussed herein) over a first time period (e.g., 1 day, 2 days, 3 days, 5 days, 7 days, 10 days, 14 days, etc.) can be determined by the remote monitoring system 120 (and/or user computing devices) based on data received from the user computing devices and/or wearable devices. As discussed elsewhere herein, one or more risk states associated with other users with which a given user has encountered (e.g., had a "contact event" with) can be utilized as contact tracing data by the remote monitoring system to determine exposure levels and/or risk states of the given user.

Each set of health-related information received by the remote monitoring system can additionally or alternatively include information/data related to a user's diagnosis and/or test result(s) with respect to one or more infections and/or diseases. Such diagnosis and/or test result information can be manually input by a user and/or input by a third party (e.g., a medical professional) who has access to the remote monitoring system and/or accessibility to interact with an application on the user's user computing device in order to input such diagnosis.

Each set of health-related information received by the remote monitoring system can additionally or alternatively include information/data related to symptom(s) experienced by the user. Such symptom(s) can be manually input by the user into a user computing device operated by a user, for example. Including an ability for a user to enter experienced symptom(s) can advantageously capture how a user is "subjectively" feeling, and can useful to supplement more "objectively" obtained information (e.g., physiological information obtained by the wearable device(s) coupled to the user). Such symptom(s) can include, without limitation, fever, chills, cough, shortness of breath or difficulty breathing, fatigue, muscle or body aches, headache, loss of taste or smell, congestion or runny nose, nausea or vomiting, diarrhea, among others).

While not illustrated in method 800, the method 800 can further include receiving other information from the user computing device(s), such as location data, movement data, orientation data, among other things, measured by a magnetometer, accelerometer, and/or gyroscope or other components of the wearable device and/or user computing device.

At step 804, the remote monitoring system determines an exposure level for a user. Such exposure level can be determined in any of the manners described elsewhere herein for all or a subset of users in an organization simultaneously or non-simultaneously. Further, such exposure level can be continuously and dynamically updated as information is received from user computing devices and/or wearable devices over time.

At step 806, the remote monitoring system determines a risk state for a user (and/or all or a subset of users in an organization). Such risk state (also referred to herein as "risk level") can be determined in any of the manners described elsewhere herein. For example, a risk state of a particular user can be determined based on one or more of user physiological information, contact tracing data, diagnosis and/or test result data, symptom(s) information, exposure levels, and/or risk state(s) of other users if available. At step 808, the remote monitoring system sends (e.g., over a network) the determined risk state and/or other information or instructions associated with such risk state to the user computing device(s). Such other information or instructions can be, without limitation: instructions to the user concerning whether to quarantine (e.g., stay home) or come into a facility of the organization; and/or information related to exposure and/or risk states of any other users who may have come into contact with the user over a period of time and/or any visual representation thereof (e.g., graphs, tables, lists illustrating such information).

Advantageously, not only can the method 800 described above be carried out for each user computing device and user associated with a given organization simultaneously, but such method 800 can be carried out on an ongoing basis, continuously determining exposure levels and risk states of such users and updating the users with such information. Although not illustrated in FIG. 8A, the method 800 can additionally involve allowing for adjustment of exposure level(s) and/or risk state(s), for example, by a monitor user of an organization tasked with overseeing the remote monitoring system. Such adjustment can be as that described elsewhere herein (e.g., with respect to FIGS. 6A-6B).

FIG. 8B illustrates a method 820 by which a user computing device (such as any of those discussed herein) can interact with one or more wearable devices associated with a user (such as any of the wearable devices discussed herein) and a remote monitoring system (such as any of the remote monitoring systems described herein). At step 822, the user computing device (such as a smart phone) of a user receives physiological information from one or more wearable devices associated with (e.g., coupled to) the user, such as any of the physiological information/data discussed herein. In some implementations, the user computing device also receives other information, such as location data and/or movement data as discussed elsewhere herein. At step 824, the user computing device can receives contact tracing data from the wearable device, such as any of the contact tracing data discussed herein. For example, such contact tracing data can include proximity data (such as any of that discussed herein) indicative of the user's proximity to one or more other users (for example, when within a threshold proximity of such one or more other users). Such contact tracing data can advantageously additionally include identification information that uniquely identifies the one or more other users and/or wearable devices coupled to the users, for example, by associating identifiers (e.g., user IDs) with the one or more other users and the user itself. In some implementations, the user computing device only receives contact tracing data (e.g., proximity data) when the user is within the threshold proximity, but continuously receives physiological information (for example, regardless of whether the user is within the threshold proximity to other users) from a wearable device.

At step 826, the user computing device sends the health-related information to the remote monitoring system, for example, over a network as described above. At step 828, the user computing device receives a risk state for the user associated with the user computing device, for example, after such risk state has been determined by the remote monitoring system. As shown and as described elsewhere herein, the user computing device can receive additional information and/or instructions related to the risk state. In some implementations, the user computing device can be configured to determine exposure levels and/or risk states alone or in combination with the remote monitoring system, and can include structure and/or functionality similar or identical to that described with respect to remote monitoring system to make such determinations.

At step 830, the user computing device can notify (e.g., display) the risk state and/or instructions or information related to the risk state to the user. For example, the user computing device can execute, via a processor thereof, instructions and/or an application enabling visual and/or audio notifications of the risk state and/or instructions or information related thereto. As another example, the user computing device can execute, via a processor thereof, instructions and/or an application enabling the user computing device to generate a graphical user interface on a display thereof, and display, in one or more portions of the graphical user interface, the risk state and/or instructions or information related thereto. Advantageously, such method 820 can allow a user to be continuously made aware of its risk state/status and/or the risk states of other users associated with the organization.

Exemplary Graphical User Interfaces

FIGS. 9A-13E illustrate various graphical user interfaces that may be accessed (e.g., viewed) by any of the user computing devices discussed herein, including user computing devices associated with user in an organization and monitor users tasked with overseeing and/or monitoring a remote monitoring system as discussed above. Such user interfaces can be accessed, for example, via a mobile or web application (for example, accessed via a browser).

Each of the user interfaces shown includes one or more user interface elements or controls that can be selected by a user. The user interface elements shown are merely illustrative examples and can be varied in other embodiments. For instance, any of the user interface elements shown may be substituted with other types of user interface elements. Some examples of user interface elements that may be used include buttons, dropdown boxes, select boxes, text boxes or text fields, checkboxes, radio buttons, toggles, breadcrumbs (e.g., identifying a page or interface that is displayed), sliders, search fields, pagination elements, tags, icons, tooltips, progress bars, notifications, message boxes, image carousels, modal windows (such as pop-ups), date and/or time pickers, accordions (e.g., a vertically stacked list with show/hide functionality), and the like. Additional user interface elements not listed here may be used.

Further, the user interfaces shown may be combined or divided into other user interfaces such that similar functionality or the same functionality may be provided fewer or more screens. Moreover, each of the user interface elements may be selected by a user using one or more input options, such as a mouse, touch screen input (e.g., finger or pen), or keyboard input, among other user interface input options. Although each of these user interfaces are shown implemented in a mobile device via a mobile application or desktop/laptop via a web application, the user interfaces or similar user interfaces can be output by any computing device, examples of which are described elsewhere herein.

Figure 9B:
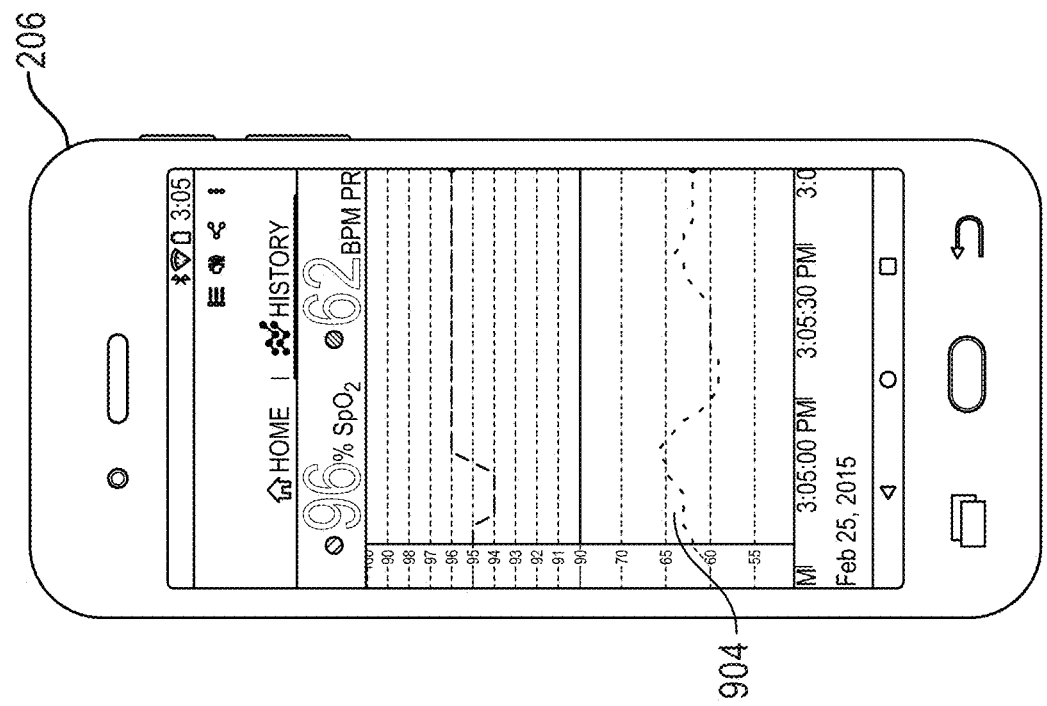
Figure 9A:
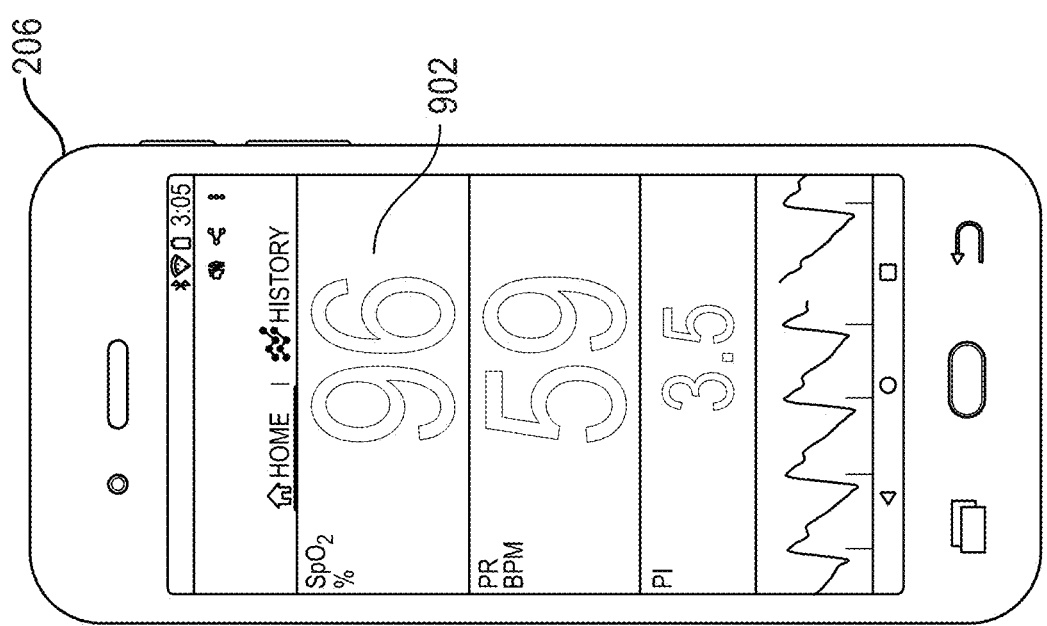

FIGS. 9A-9B illustrate user interfaces which display, on a user computing device 206, various physiological parameters that are received from one or more wearable devices, such as any of those discussed herein. In FIG. 9A, the depicted graphical user interface includes user physiological parameter values 902. As shown, example physiological parameters 902 can include blood oxygen saturation (SpO$_2$), pulse rate (PR), and/or perfusion index (PI). Values indicative of such physiological parameters 902 can be dynamically updated in real-time. In FIG. 9B, another graphical user interface is depicted that includes user physiological parameters. The graphical user interface of FIG. 9B can further include historical data. In particular, the graphical user interface can include a visualization 904 that presents historical trends of user physiological parameter values. As shown, the visualization 904 can include one or more graphs with an x-axis of time and a y-axis of parameter values. The underlying historical data can originally be generated, at least in part, by the one or more wearable devices.

Figures 10C, 10D, 10E:
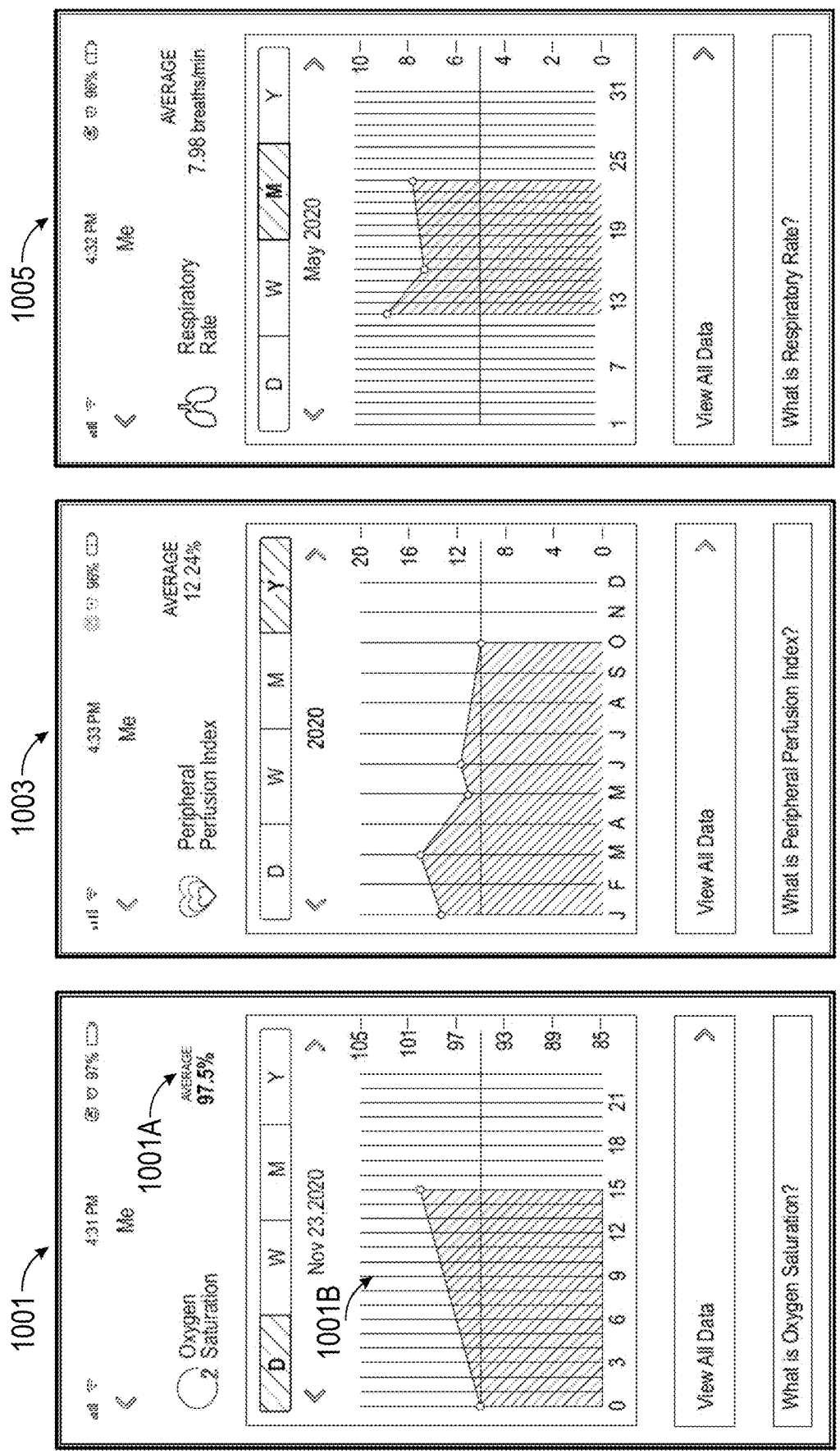

FIGS. 10A-10E illustrate example graphical user interfaces of an application that can be utilized by a user computing device (such as any of those discussed herein). FIG. 10A illustrates a graphical user interface 1000 of an application, such as a mobile application. The graphical user interface 1000 can include a feed 1006, which can present the user interface option(s) 1008 that correspond to a user interface that has been shared with the user (here the "COPD Maintenance with MightySat" user interface). The graphical user interface 1000 can provide further access to the user to other aspects of the application. For example, the user can access a dashboard user interface, which can present physiological parameters, via the dashboard element 1002. An example dashboard user interface is described in further detail below with respect to FIG. 10B. As another example, the user can access a sharing configuration user interface via the sharing element 1004. As described herein, a sharing configuration user interface can allow a user to modify their sharing permissions, such as by identifying and/or modifying other users (for example, within a remote monitoring system) that are permissioned to view at least some the user's data/receive alerts regarding the user.

FIG. 10B illustrates an example dashboard user interface 1000' of the application. The dashboard user interface 1000' can include one or more physiological parameter summaries 1010A, 1010B, 1010C, 1010D. As shown, each of the example physiological parameter summaries 1010A, 1010B, 1010C, 1010D can be associated with different physiological parameters. The dashboard user interface 1000' can include more or less physiological parameter summaries based on the particular configuration or embodiment. The physiological parameter summaries 1010A, 1010B, 1010C, 1010D can allow a user to review physiological parameters. The one or more physiological parameter summaries 1010A, 1010B, 1010C, 1010D can be associated with physiological parameters including, but not limited to, blood pressure, blood oxygen saturation, heart rate, respiration rate, body weight, or body temperature. A user can select the one or more physiological parameter summaries 1010A, 1010B, 1010C, 1010D to access additional details related to the physiological parameter associated with the selected physiological parameter summary 1010A, 1010B, 1010C, 1010D.

The physiological parameter summary 1010A can include a physiological parameter name 1012, a physiological parameter value 1014, and a visualization 1020. The physiological parameter value 1014 (here an oxygen saturation value) can be associated with a date and/or time 1018, such as when the measurement was taken. An example visualization 1020 can be a graph of physiological parameter values, such as a trend graph. The visualization 1020 can display an overall trend of the parameter associated with the physiological parameter summary 1010A. The visualization 1020 may be based on physiological data from one or more wearable devices that collect data from a user.

The dashboard user interface 1000' can include one or more elements 1030 that indicate users that are authorized to view and/or access user data, such as the physiological parameter summaries 1010A, 1010B, 1010C, 1010D. Accordingly, a user of the application can readily identify who has access to the physiological parameter summaries 1010A, 1010B, 1010C, 1010D. A user may add other users as authorized users via the add user element 1040. Once added as authorized users, those other users may be able to view and/or access the physiological parameter summaries 1010A, 1010B, 1010C, 1010D associated with the user. User selection of the add user element 1040 may cause the application to present a graphical user interface that can allow the user to identify one or more users to be added as authorized users.

FIGS. 10C-10E illustrate example physiological parameter detail user interfaces of the application. In particular, FIG. 10C illustrates a physiological parameter detail user interface 1001 associated with blood oxygen saturation. The physiological parameter detail user interface 1001 can include a statistical measurement value 1001A, such as an average physiological parameter value (here an average blood oxygen saturation of 97.5 percent). The physiological parameter detail user interface 1001 can include a visualization 1001B, such as a graph showing blood oxygen saturation values over time. As shown, the visualization 1001B can include user interface elements that allow a user to interact with the visualization 1001B, such as by changing the time period associated with the visualization. Additional example visualizations (not shown) can include, but are not limited to, a bar graph, scatter plot, pie chart, etc. In some embodiments, the visualization 1001B can use different indicators to display different data points in. For example, the visualization 1001B can use the color green for data points within a predetermined range, the color yellow for data points within a different predetermined range, and the color red for data points outside of those predetermined ranges.

FIG. 10D illustrates another physiological parameter detail user interface 1003 associated with respiratory rate. FIG. 10E illustrates yet another physiological parameter detail user interface 1005 associated with peripheral perfusion index. The physiological parameter detail user interfaces 1003, 1005 of FIGS. 10D and 10E can be similar to the physiological parameter detail user interface 1001 of FIG. 10C, such as by including similar user interface elements and/or operating in a similar manner. For example, the physiological parameter detail user interfaces 1003, 1005 of FIGS. 10D and 10E can each include a visualization, like visualization 1001B. However, the physiological parameter detail user interfaces 1003, 1005 of FIGS. 7D and 7E can have different selected time periods than the selected time period of the physiological parameter detail user interface 1001 of FIG. 10C.

Figure 11B:
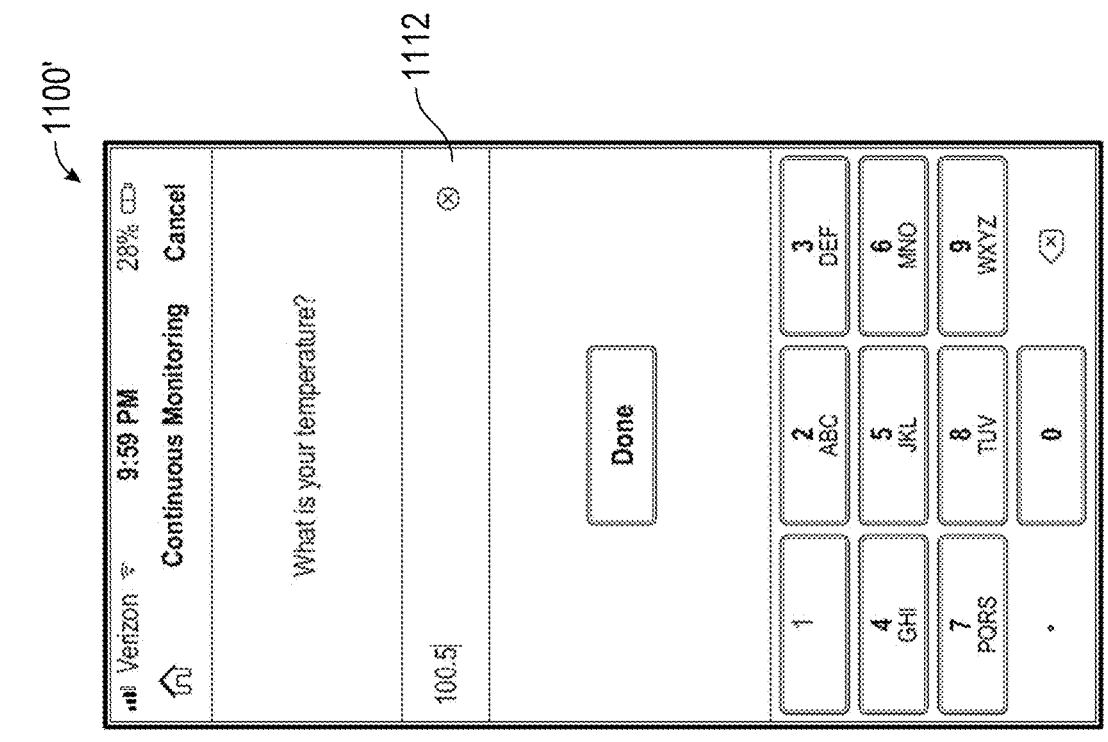
Figure 11A:
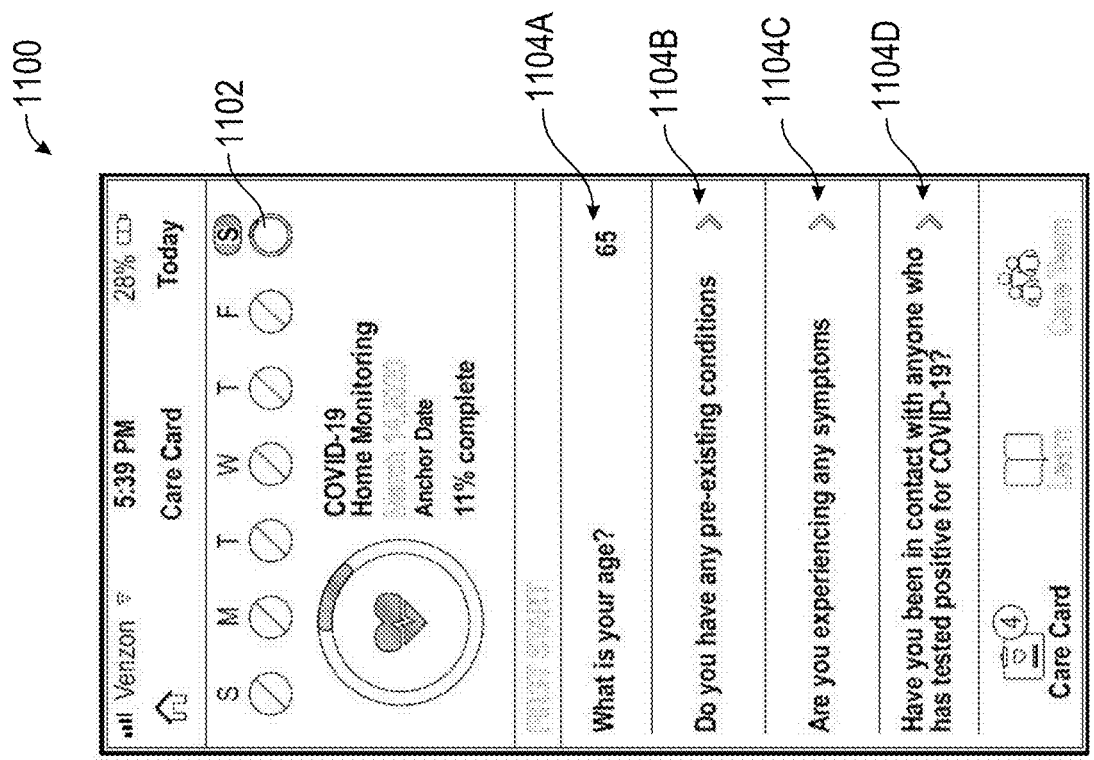
Figure 11C:
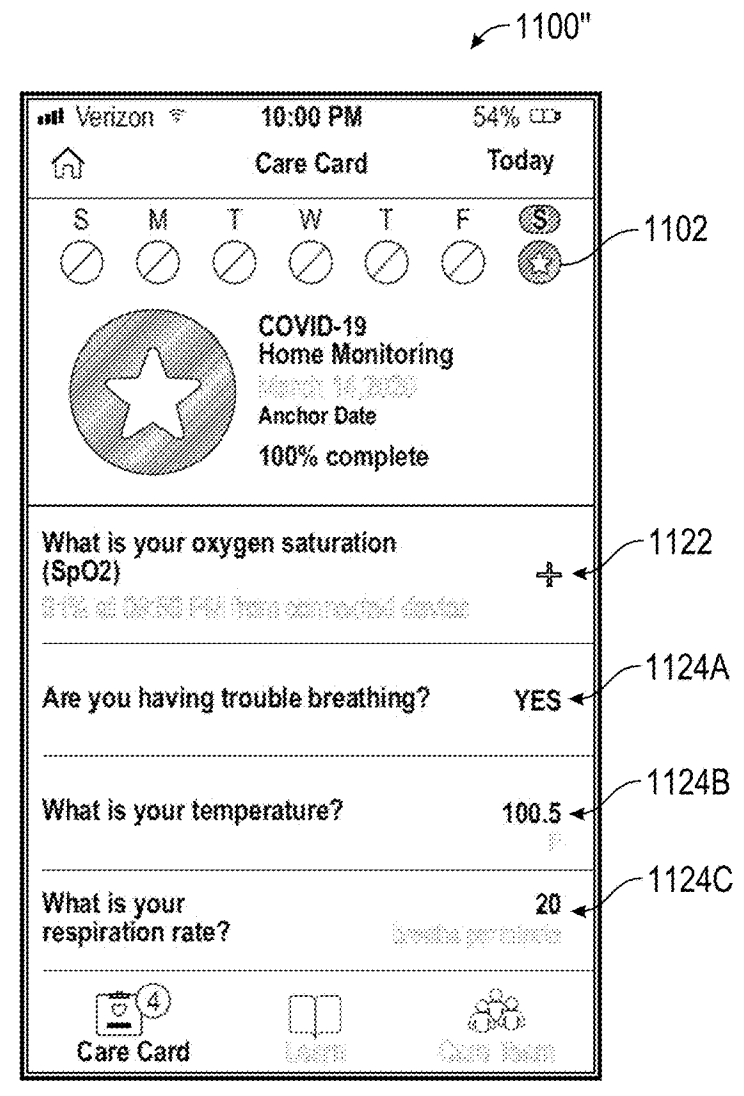

FIGS. 11A-11C illustrate additional example user interfaces of an application that can be utilized by any of the user computing devices discussed herein. The user interface of FIGS. 11A-11C can be directed towards one or more infections, such as the novel coronavirus and/or COVID-19 health condition(s). FIG. 11A illustrates an example user interface 1100. In FIG. 11A, the graphical user interface 1100 includes a timeline 1102. As shown, the current day in the timeline 1102 has several items 1104A, 1104B, 1104C, 1104D to be completed by a user. The example items 1104A, 1104B, 1104C, 1104D can be questionnaire and/or action items to be completed and/or inputted by the user. The items 1104A, 1104B, 1104C, 1104D can include prompts that elicit user responses. The items 1104A, 1104B, 1104C, 1104D can correspond to an initial questionnaire related to symptoms that may be associated with health condition(s) and/or infections. In the case of the novel coronavirus and/or COVID-19 and/or other use cases, example questions/prompts can include: "What is your age?", "Do you have pre-existing conditions", "Are you experiencing any symptoms", "Have you been in contact with anyone who has test positive for COVID-19?", or any other questions described herein. The responses to the questions can be transmitted by the user computing device to the remote monitoring system as described elsewhere herein.

FIG. 11B illustrates another example user interface 1100'. The user interface 1100' can include an input area 1112 for a question and/or action item (here an item to receive a user's temperature as user input). As shown, a user can input a temperature value. Alternatively, in some embodiments, instead of being received via manual user input, a user interface be configured to display one or more temperature values of the user obtained and received from one or more wearable devices, as discussed elsewhere herein.

FIG. 11C illustrates yet another example user interface 1100". The user interface 1100" of FIG. 11C can be similar to the user interface 1100 of FIG. 11A. In particular, the user interface 1100" of FIG. 11C can represent a progression of completed items (e.g., answered questions, etc.) from the user interface 1100 of FIG. 11A. For example, the user interface 1100" of FIG. 11C can include indicators of the user's progress (such as a visual icon representing a completed status for a particular day in the timeline 1102, such as a visual star icon, and/or the text "100% complete"). The user interface 1100" can include a visual representation 1122 of a user device configuration. The user device configuration can facilitate the interface between the application and one or more wearable devices coupled to the user of the user computing device where the application is running.

The user interface 1100" can further include several items 1124A, 1124B, 1124C. The example items 1124A, 1124B, 1124C can be questions and/or action items, which can be completed by the user. For example, the item 1124A with the prompt (such as "Are you having trouble breathing?") can elicit a yes/no response to be provided from the user. The user can select the second item 1124B that can cause presentation of the user interface 1100' of FIG. 11B. The third item 1124C (shown as a respiration rate item) can be an item that can receive user input and/or that displays physiological information derived from one or more wearable devices in communication with the user computing device. Similar to the items 1104A, 1104B, 1104C, 1104D of FIG. 11A that can be directed towards the novel coronavirus and/or COVID-19, the items 1122, 1124A, 1124B, 1124C of FIG. 11C can likewise be directed towards the novel coronavirus and/or COVID-19. For example, the items 1122, 1124A, 1124B, 1124C of FIG. 11C can be directed towards the symptoms of COVID-19 or any other respiratory disease (that can potentially be very dangerous) such as low oxygen saturation, high body temperature, difficulty breathing, and/or too low or too high of a respiration rate. However, any of the user interfaces 1100, 1100', 1100" can be directed to diseases other than COVID-19, for example, to flu or common cold.

Figure 12A:
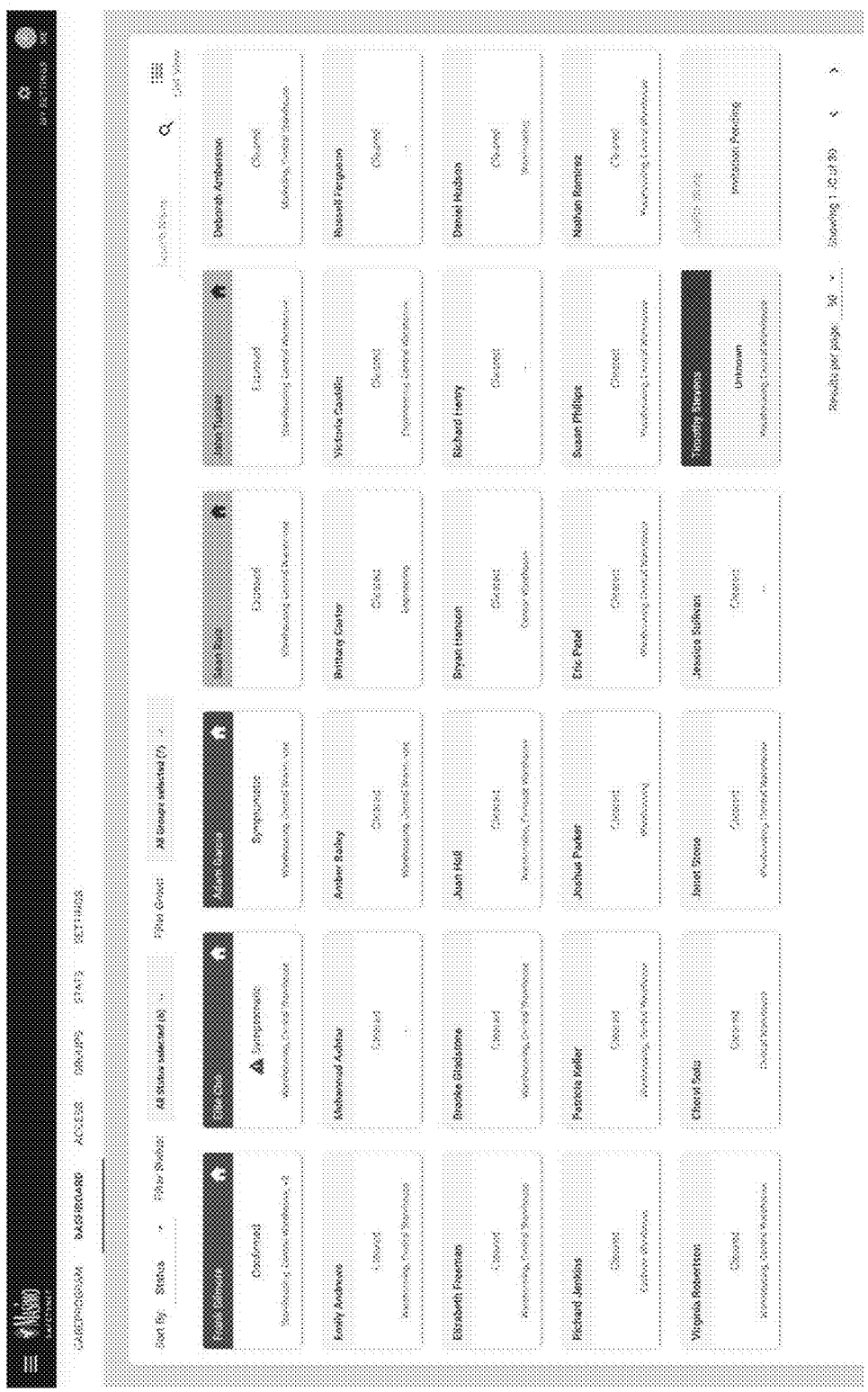

FIG. 12A illustrate exemplary user interfaces that can be associated with any of the remote monitoring systems described herein. As discussed previously, the remote monitoring systems can be viewed by one or more monitor users of an organization who is tasked with overseeing and/or interacting with one or more user computing devices and associated users of the organization. The exemplary user interfaces of FIGS. 12A-12G can be displayed on one or more computing devices operated by such monitor users and accessed via a web application (e.g., via a browser) and/or via a mobile application on a mobile device operated by such monitor use (e.g., a tablet, laptop, mobile phone, etc.).

FIG. 12A illustrates an exemplary user interface 1200 that can be used by a monitor user of a remote monitoring system. User interface 1200 can advantageously display one or more user profile/statuses (as shown by the array of boxes with user name and status) in the view. Such can be available in a "Dashboard" view of the application, which can be one of various other types of "views" available to the monitor user, such as "Access", "Groups", "Stats", "Settings", "Careprogram." The user profile and status appearing in this figure can be linked with one or more databases of a remote monitoring system, such as database(s) 404 as discussed elsewhere herein with respect to remote monitoring system 120. As shown in FIG. 12A, the user interface 1200 can display user names, user statuses (for example, risk states such as those discussed elsewhere herein), and/or can include various other information that can help efficiently and simply convey such statuses, such as color coding associated with risk state ("red", "yellow", such as that discussed elsewhere herein) and/or a risk state/status label (such as "Confirmed", "Symptomatic", "Exposed", "Cleared", etc.).

Figure 12B:
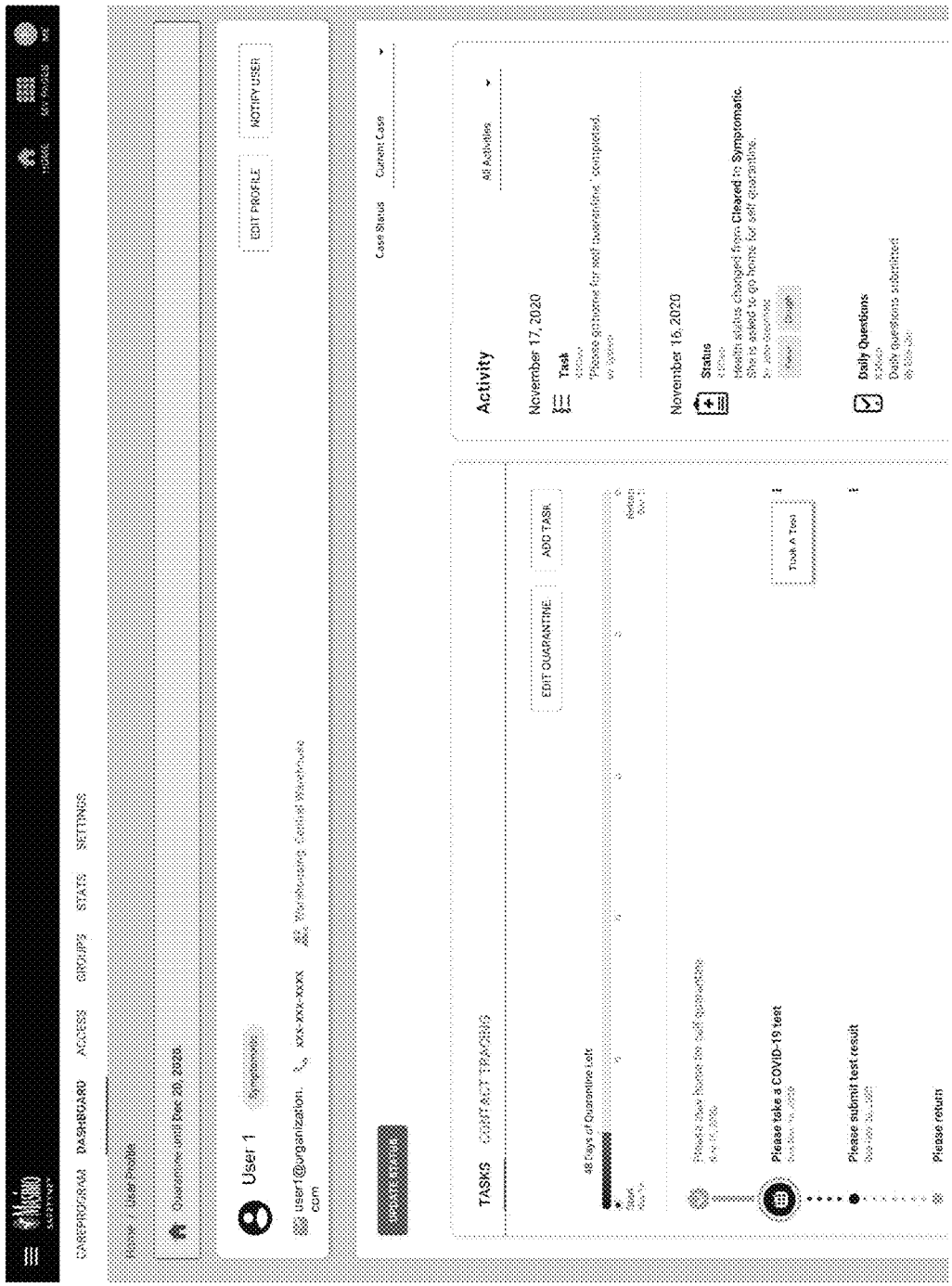

FIG. 12B illustrates another exemplary user interface 1201. User interface 1201 can represent a view that can appear if the monitor user selected one of the box icons in user interface 1200 which included a particular user (e.g., "User 1"). User interface 1201 can advantageously present information specific to the particular user, including but not limited to, contact information (e.g., email, phone number, location, job title, groups within the organization that the particular user is associated with, etc.). As shown, information concerning status, tasks or instructions, and/or contact tracing can be displayed. For example, as shown, the user interface 1201 can display tasks related to a user quarantining for a given period of time (e.g., "48 days of quarantine left") and/or tests for a particular infection (e.g., COVID-19). As also shown, user interface 1201 can display activity and/or history of the particular user, for example, along a timeline. Such activity and/or history information can include specific tasks, status, and/or daily questions.

User interface 1201 can represent a view that a monitor user would see if accessing an application via the a computing device of the remote monitoring system and/or can represent a view that a particular user would see if the particular user accessed the application via a computing device such as a laptop or desktop via a web browser. Where accessed in such manner by the particular user, in some implementations the application allows the user to input information and edit various aspects of the application. User interface 1201 can allow the monitor user and/or the user represented in the user interface 1201 to edit the user's profile and/or status. User interface 1203 in FIG. 12C illustrates a view that can appear if the monitor user and/or another user selected the "Update Status" icon in user interface 1201. As illustrated in user interface 1203, various aspects of a user's status can be modified/updated, such as a "Health Status" (e.g., "symptomatic", "clean", "confirmed", "infected", "asymptomatic", etc.), "Symptom Starting Date" (e.g., an "onset" date of symptoms), "Symptoms" (e.g., fever or temperature over a threshold such as 100.4° F. or 38° C.), chills, cough, sore throat, fatigue, shortness of breath, vomiting, diarrhea, loss of taste and/or smell, or other symptoms, and/or "Notes" which can include other information such as whether the user was asked to self-quarantine.

Figure 12D:
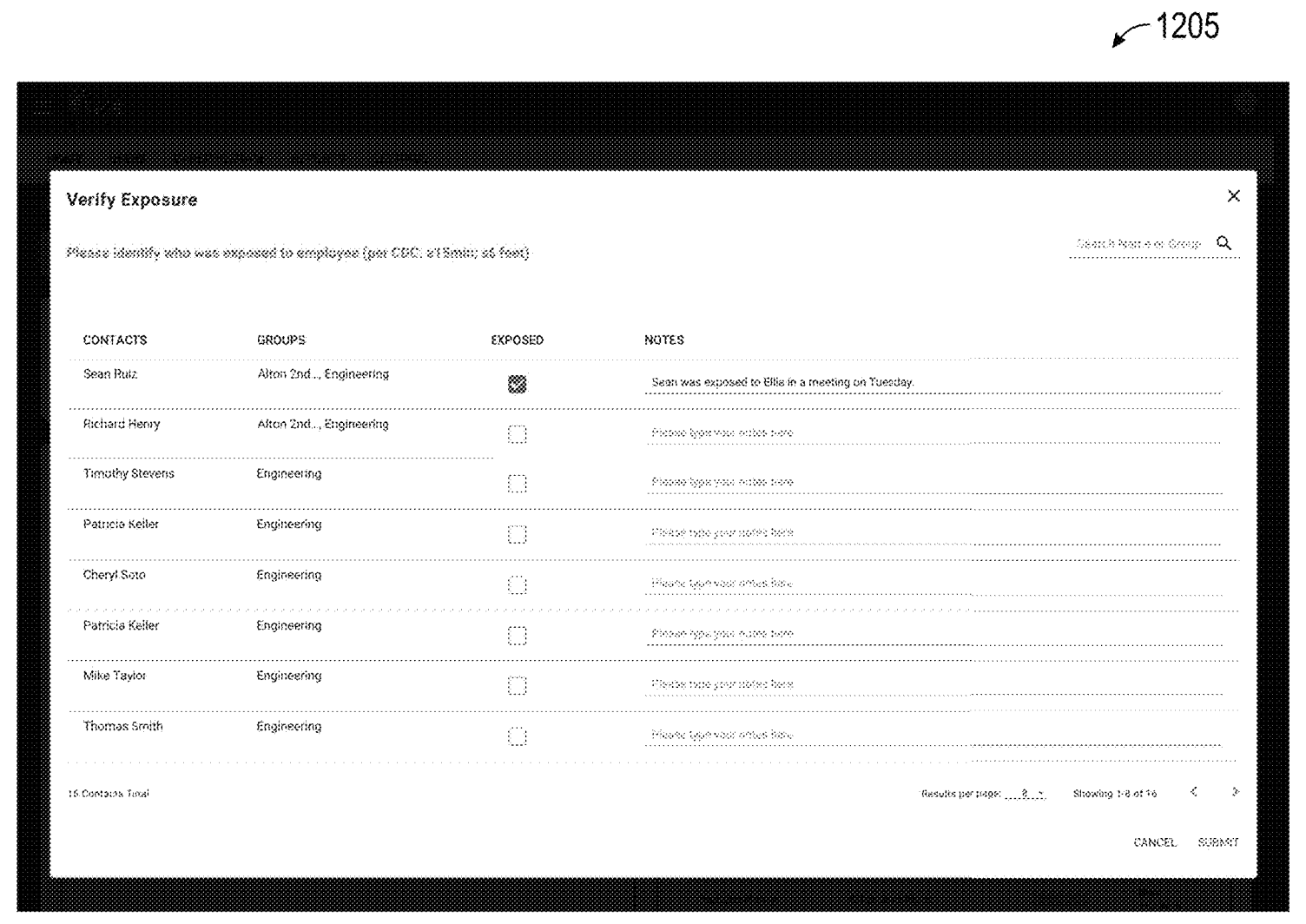

FIG. 12D illustrates another exemplary user interface 1205 that can allow entry and/or verification of exposure data indicative exposure a user has had to one or more other users. Such exposure can be representative of and/or associated with a "contact event" such as those discussed elsewhere herein where a user is within a threshold proximity of one or more other users for a given amount of time. For example, as shown in FIG. 12D, an "exposure" can be a contact event with another user within 6 ft for a period of greater than or equal to 15 minutes. However, various other threshold distances and/or time periods can be used to define such "exposure", such as any of those discussed herein. User interface 1205 can display a list of contacts (e.g., users), groups which may be a subset of the organization to which a particular user belongs, a box which can be indicative of an exposure (see "Exposed" text), and a "Notes" list which can allow entry and/or verification of descriptions related to contact events.

Figure 12E:
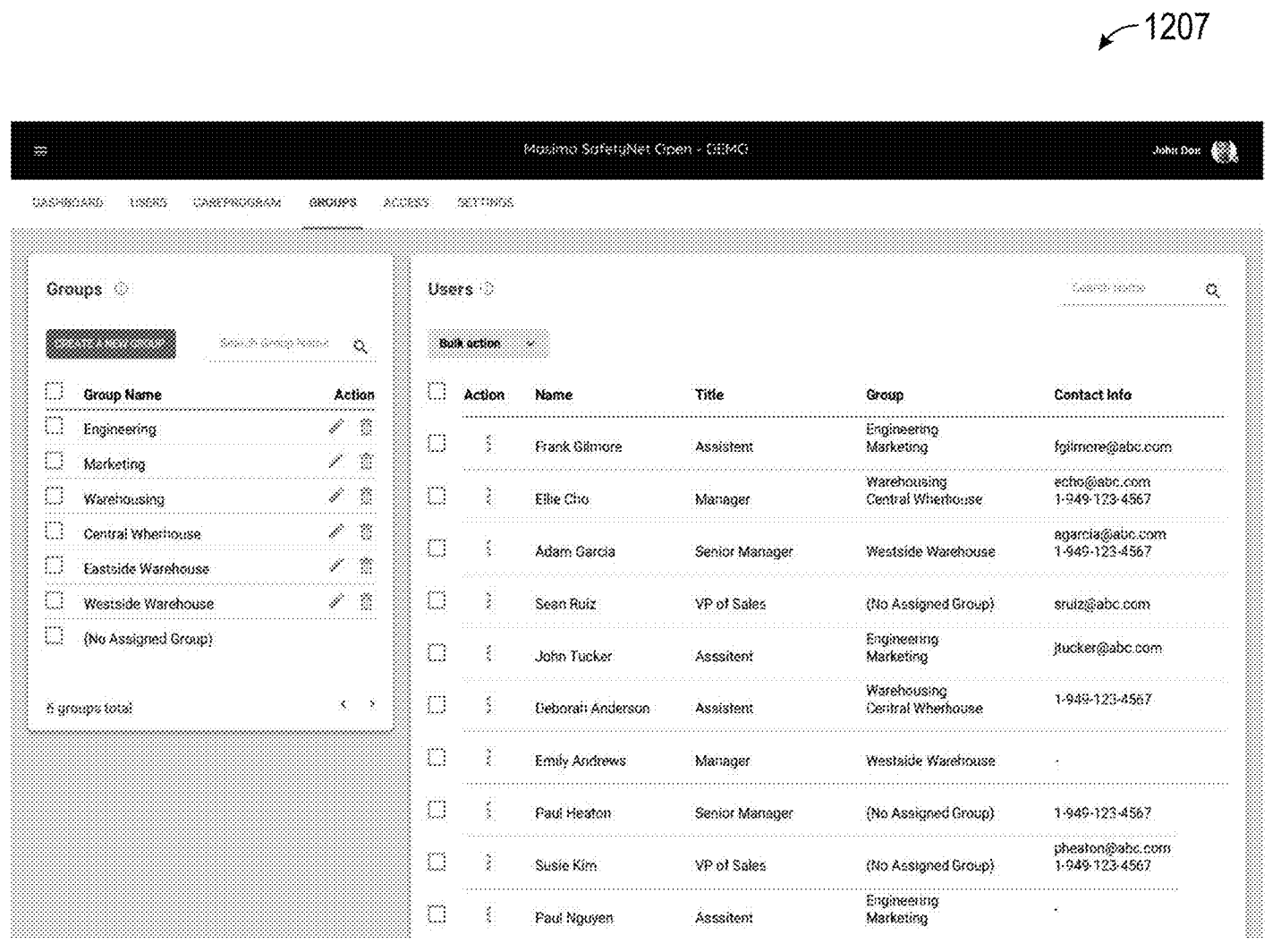

FIG. 12E illustrates another exemplary user interface 1207 which allowing viewing and/or modification of groups of users within an organization. User interface 1207 can advantageously facilitate subdividing all the users in an organization into groups which can be defined by sets of users who work together in certain portions of the organization's facilities and/or who share similar tasks or job descriptions. The viewing and/or modification of such groups can allow simple and efficient monitoring and management of users. As shown, a plurality of groups can be created which subdivide the users in the organization by job title and/or location, for example, "Engineering", "Marketing", "Warehousing", "Central Warehouse", "Eastside Warehouse", "Westside Warehouse", etc.). Selection of any of such plurality of groups can allow "Bulk Actions" to be undertaken, such as modifying risk states and/or instructions for all users within a particular group.

Figure 12F:
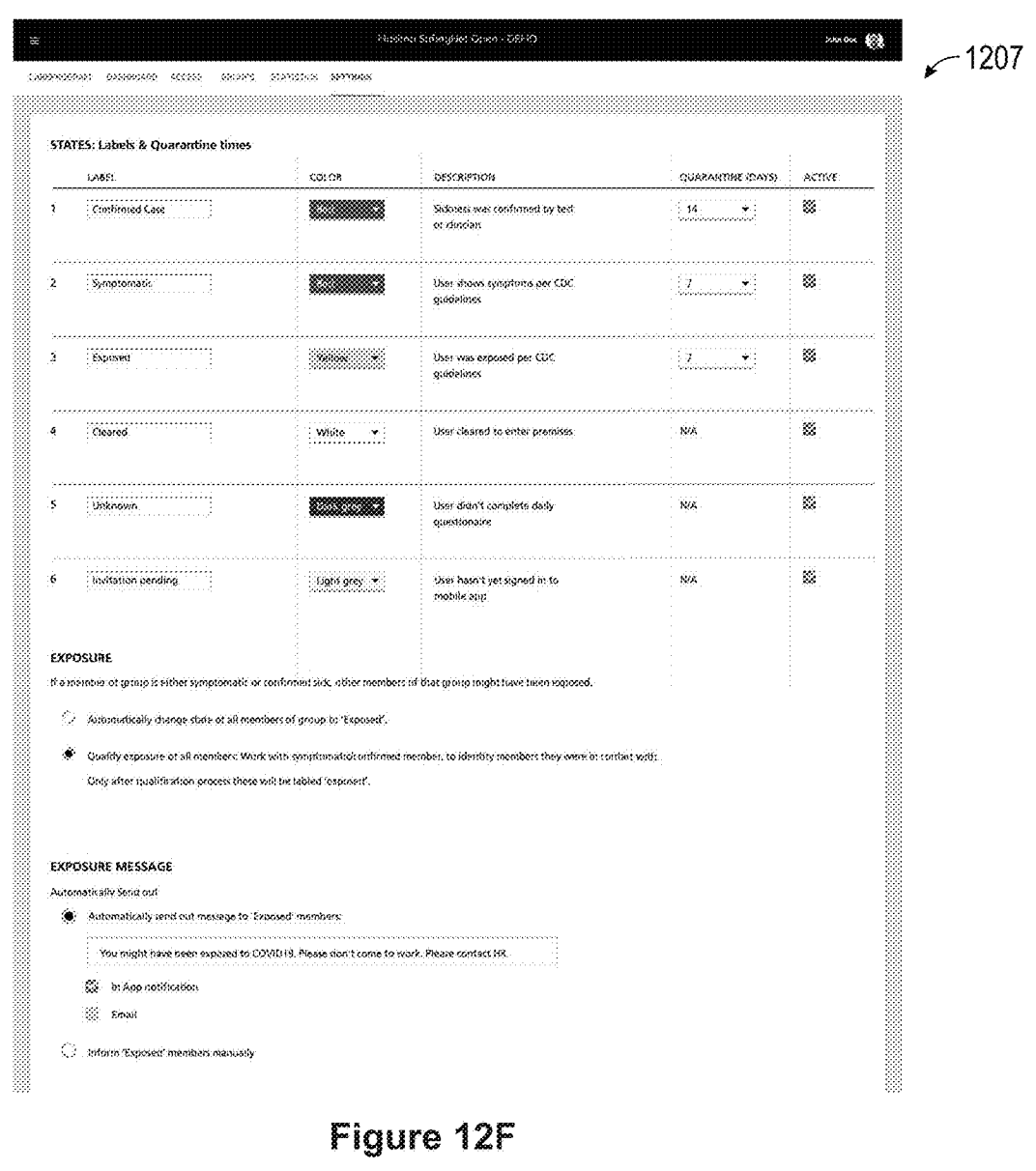

FIG. 12F illustrates another exemplary user interface 1207. User interface 1207 illustrates an exemplary "Settings" view that can allow, for example, a monitor user to change various settings of the remote monitoring system and/or an application associated therewith which can affect how the application is executed on any user computing device of any of the plurality of users of an organization. As shown, user interface 1207 can allow the creation and/or modification of, without limitation: risk labels or risk states (see "Label" column); associated visual characteristics (e.g., "Red" "Yellow", "White", "Dark grey", "light grey", etc.); risk label/state descriptions (see "Description" column); quarantine time (see "Quarantine (Days)" column); and whether a given risk label/state is "Active". As also shown, user interface 1207 can allow modification of exposure and/or risk state determination settings. For example, if a member of a group (such as the groups discussed above) is either symptomatic or confirmed to be infected, other members of that group might have been exposed. In such cases, the user interface 1207 can configure the a remote monitoring system and/or application associated therewith to automatically change a risk state of all members in such group to "Exposed" or alternatively, to qualify exposure of all members based on one or more parameters such as whether the member worked with a symptomatic/confirmed member whether the user can identify who they were in contact with, and subsequent to that qualification, determine whether to label the user as "exposed." User interface 1207 can also allow configuration for exposure notification messages (e.g., alerts) to be sent out to one or more users of a group if a determination is made that a user from that group was infected. The user interface 1207 can allow customization of the message and the method of transmission (e.g., email, in app notification viewable on the users' user computing device, text message, etc.). User interface 1207 can also allow for such "automatic" notifications to be disabled in view of manual notifications, for example.

Figure 12G:

FIG. 12G illustrates another exemplary user interface 1209. User interface 1209 illustrates an exemplary "Stats" view that can allow, for example, a monitor user to view statistics on all users of the organization or a subset (e.g., a group) of users within the organization. As shown, user interface 1209 can include information and/or a visual representation associated with: total number of cases of an infection (e.g., number of diagnosed users, number of symptomatic users, number of exposed users); trending information and/r graphs indicative of the number of open cases over a given time period (e.g., 1 day, 3 days, 5 days, 7 days, 14 days, 1 month, 2 months, 6 months, one year, etc.); "Daily Check-in" information which can be indicative of the number of users that are checking in (e.g., by registering their user computing device with a screening device or in another manner) to a facility of the organization; and/or "Estimated Return Date" information that can represent a timeline of return dates for users who are quarantining.

Figure 13C:
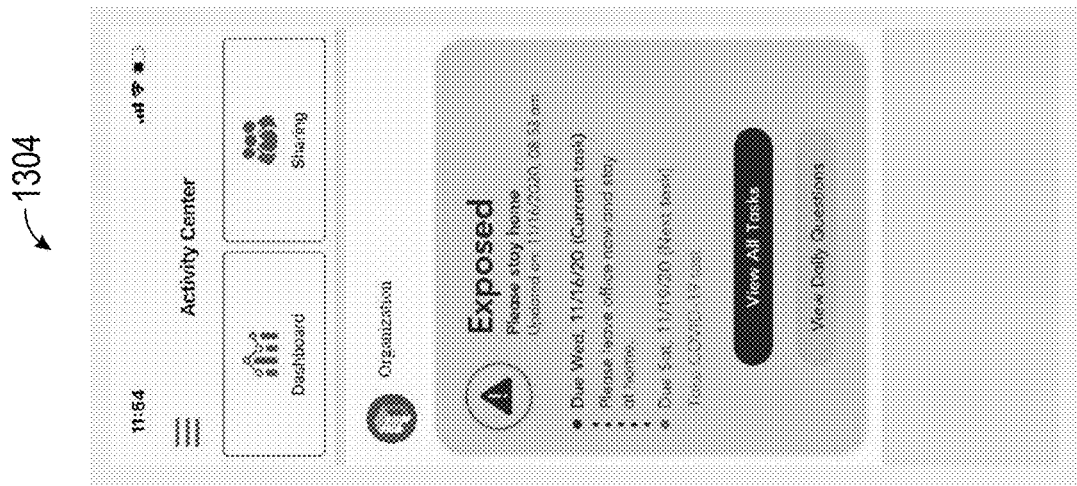
Figure 13B:
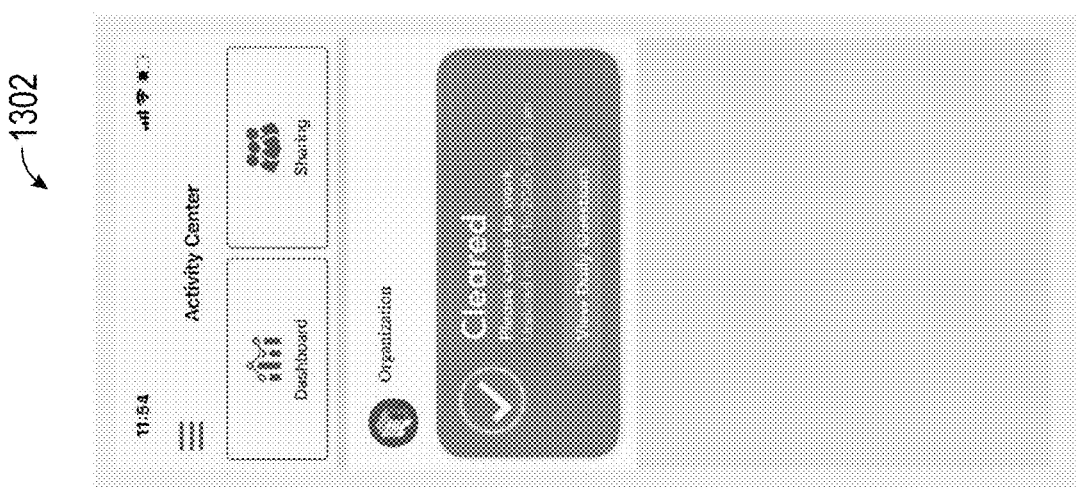
Figure 13A:
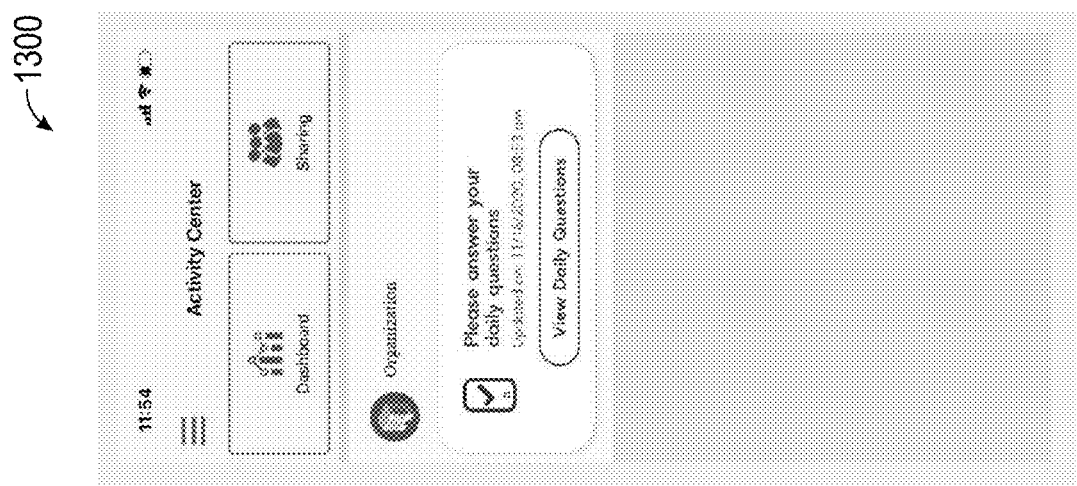
Figures 13D, 13E:
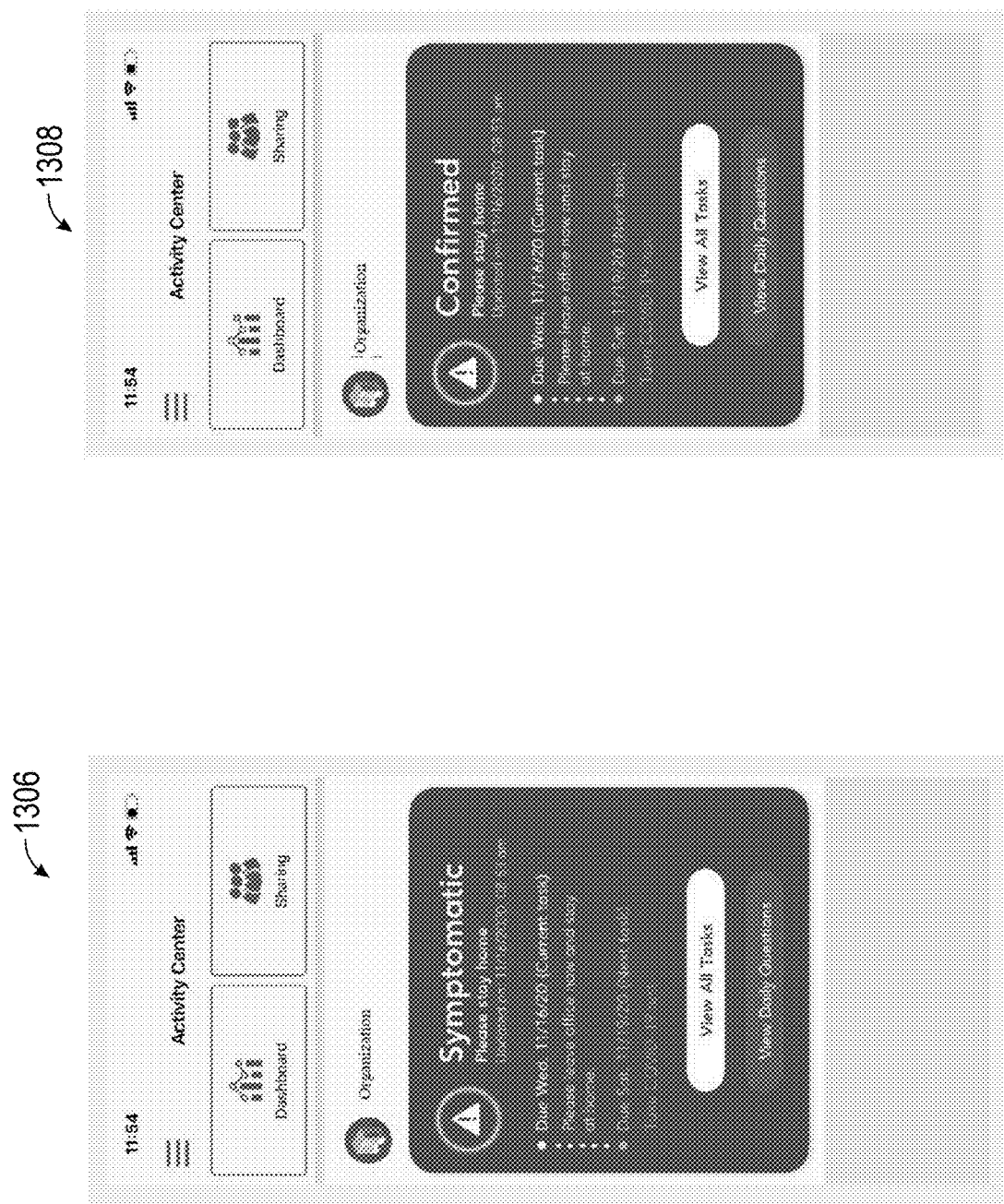

FIGS. 13A-13E illustrate exemplary user interfaces 1300, 1302, 1304, 1306, 1308 that can be utilized in a mobile application of a user computing device (such as any of the user computing devices discussed herein). However, all or portions of such user interfaces 1300, 1302, 1304, 1306, 1308 can be utilized by a web application of a user computing device, for example, via a browser. FIG. 13A illustrates a user interface 1300 that can include, among other things, a prompt for a user to answer daily questions that can be related to and/or indicative of an infection. Such daily questions can be any of the questionnaire and questions discussed elsewhere herein, for example, with reference to symptom information. Such daily questions may also be related to and/or indicative of diagnosis data (e.g., received from a medical professional), test results, contact tracing data (such as any of that discussed herein), among other information. Based on the user's answers to such daily questions and/or based on other determinations that may be made by a remote monitoring system receiving such answers (via a user computing device), the remote monitoring system can communicate with the user computing device and the user computing device can display the user's risk state/status and/or other information related thereto. For example, the user computing device can display: a "Cleared" notification accompanied by an instruction or suggestion to come into work and/or a color coordinated indicator (e.g., "green") as shown in user interface 1302 in FIG. 13B; a "Exposed" notification accompanied by an instruction for the user to stay home and/or a color coordinated indicator (e.g., "yellow") as shown in user interface 1304 in FIG. 13C; a "Symptomatic" notification accompanied by an instruction for the user to stay home and/or a color coordinated indicator (e.g., "red") as shown in user interface 1306 in FIG. 13D; and/or a "Confirmed" notification accompanied by an instruction for the user to stay home and/or a color coordinated indicator (e.g., "red") as shown in user interface 1308 in FIG. 13E.

FIGS. 14A-14B illustrate additional exemplary user interfaces 1400, 1400' that may be generated by a one or more hardware processors of a computing device via a mobile and/or web based application executed by the computing device. User interfaces 1400, 1400' advantageously can illustrate contact tracing data in a simple and effective manner. User interfaces 1400, 1400' can illustrate, over a period of time and/or along a timeline, one or more contact events that a user has with one or more other users, for example, in an organization.

Proximity data (such as any of that discussed herein) can be obtained from a wearable device (such as any of the wearable devices discussed herein) and can be transmitted to a user computing device (such as any of the user computing devices discussed herein) associated with (e.g., belonging to) a user. Such user computing device (e.g., smartphone) associated with the user can receive and transmit such proximity data to a remote monitoring system (such as any of the remote monitoring systems discussed herein). Additionally or alternatively, such proximity data can be obtained from the wearable device and can be directly transmitted to the remote monitoring system (e.g., without utilization of the user computing device).

One or more hardware processors associated with the remote monitoring system can execute an application (e.g., software application, web or mobile application, etc.) that can execute commands to enable a computing device associated with the remote monitoring system (e.g., a computing device operated by a monitor user tasked with overseeing the remote monitoring system and/or users, wearable devices, and/or user computing devices interacting with the remote monitoring system) to undertake various actions. Such actions can include, for example: receiving proximity data from the wearable device (either directly or via a user computing device), the proximity data indicative of distance between the wearable device and a separate wearable device coupled to a second user; receiving a first identifier associated with the user and/or the wearable device of the user; receiving a second identifier associated with the second user and/or the separate wearable device; store said proximity data over time along with the first and second identifiers; and/or determine one or more contact events based on the proximity data, where each of the one or more contact events is representative of the first and second users being within a threshold proximity (such as any of the threshold proximities discussed herein) for a continuous period of time. Such actions can additionally include generating a graphical user interface on a display of the computing device associated with the remote monitoring system (e.g., computing device used by a monitor user) and generating a timeline (that can be continuously updated over time) and a visual representation of such one or more contact events along a timeline.

Such visual representation(s) can be in the form of a shape and/or can have a color, for example. Such visual representation(s) can be a bubble, as illustrated in FIGS. 14A-14B. In some implementations, a size and/or other characteristic of bubble correlates with and/or is indicative of the period of time in a contact event. For example, a first contact event between two users where the two users were within a threshold proximity (e.g., 6 ft) from one another for 20 minutes can be represented by a bubble that has a greater size, shape, perimeter, and/or other characteristic (e.g., radius, diameter) than a second contact event where the two users were within the threshold proximity for 5 minutes. The visual representation(s) can be represented by a square, diamond, among other shapes. As another example, each contact event can be represented by a circle, where a diameter of the circle corresponds to the length of time of the contact event (e.g., the duration of time that a user was within a threshold proximity of another user).

With reference to FIG. 14A, a first point along a perimeter of a bubble representing a contact event can represent the time at which the contact event began and a second point along the perimeter of the bubble can represent the time at which the contact event ended. In some implementations, the bubble(s) can be color coordinated for each user (e.g., each user is represented with a different color) or can be color coordinated based on risk state of each user (e.g., user's confirmed with an infection can be represented by a "red" bubble and user's not infected can be represented by a "green" bubble). For example, multiple bubbles can be generated along the timeline to represent, for example, multiple, distinct contact events between the same users.

Where a given user had contact events with multiple users at the same time, bubbles may overlap, thus causing, in some implementations a darker shade in that region. Advantageously, user interface 1400, 1400' can be generated, for example, continuously, for every user of an organization, and can be viewed by the object user and/or a monitor user of an organization. Such user interface 1400, 1400' accordingly presents a dynamic method by which contact events can be conveniently be monitored.

Any and all of the systems, methods, devices, and/or user interfaces described herein can incorporate and/or be used alongside any and all of the systems, methods, devices, and/or user interfaces described in co-pending U.S. patent application Ser. No. 17/207,469, filed on Mar. 19, 2021, titled "REMOTE PATIENT MANAGEMENT AND MONITORING SYSTEMS AND METHODS," which is hereby incorporated by reference in its entirety.

Additional Considerations and Terminology

Although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

Conditional language used herein, such as, among others, "can," "could," "might," "may," "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

Although certain embodiments and examples have been described herein, it will be understood by those skilled in the art that many aspects of the systems and devices shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Any methods disclosed herein need not be performed in the order recited. The methods disclosed herein may include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (for example, not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

Various illustrative logical blocks, modules, routines, and algorithm steps that may be described in connection with the disclosure herein can be implemented as electronic hardware (e.g., ASICs or FPGA devices), computer software that runs on general purpose computer hardware, or combinations of both. Various illustrative components, blocks, and steps may be described herein generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, various illustrative logical blocks and modules that may be described in connection with the disclosure herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. A processor can include an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of any method, process, routine, or algorithm described in connection with the disclosure herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A wearable device for monitoring a user's health status, the wearable device comprising:
   at least one physiological sensor configured to measure one or more physiological parameters of a first user, said at least one physiological sensor comprising a temperature sensor configured to generate one or more signals responsive to a thermal energy of the first user;
   a first wireless transceiver configured to communicate with a mobile computing device of the first user; and
   a processor configured to:
      receive said one or more signals generated by the temperature sensor and determine one or more body temperature values of the first user based on said received one or more signals;
      detect a wireless signal strength between the first wireless transceiver of the wearable device and a second wireless transceiver of a separate wearable device that is coupled to a second user;
      based on at least the detected wireless signal strength, determine a distance between the wearable device and the separate wearable device;
      instruct the first wireless transceiver to transmit to the mobile computing device said determined one or more body temperature values continuously regardless of the distance between the wearable device and the separate wearable device; and
      in response to determining, based on at least the detected wireless signal strength, that the distance between the wearable device and the separate wearable device is within a threshold proximity, instruct the first wireless transceiver of the wearable device to transmit to the mobile computing device when the wearable device and the separate wearable device are within said threshold proximity:
         a first identifier associated with the first user and indicative of an identity of the first user;
         a second identifier associated with the second user and indicative of an identity of the second user, wherein the second identifier is wirelessly received at the wearable device from the separate wearable device; and
         the distance between the first wearable device and the separate wearable device without location information of the wearable device and the separate wearable device, said mobile computing device configured to wirelessly transmit said first and second identifiers, said one or more body temperature values, and said distance to a remote monitoring system for determination of a risk state of the first user based on analyzing said one or more body temperature values, said distance, and information associated with said second identifier, wherein said risk state indicates a likelihood that said first user has one or more infections.

2. The wearable device of claim 1, wherein the wearable device is configured to determine only one type of physiological parameter of the first user, said type of physiological parameter being temperature of the first user.

3. The wearable device of claim 1, wherein said threshold proximity comprises 20 ft.

4. The wearable device of claim 1, wherein the processor is configured to instruct the first wireless transceiver to transmit to the mobile computing device said determined one or more body temperature values continuously every minute.

5. The wearable device of claim 1, wherein said distance is determined based on a detected Bluetooth® signal strength between the first and second wireless transceivers.

6. A system comprising the wearable device of claim 1 and said mobile computing device.

7. The wearable device of claim 1, wherein the processor is configured to instruct the first wireless transceiver to transmit to the mobile computing device a duration of time that the distance between the wearable device and the separate wearable device is within the threshold proximity.

8. The wearable device of claim 1, wherein the processor is configured to instruct the first wireless transceiver to transmit to the mobile computing device a number of times that the distance between the wearable device and the separate wearable device is within the threshold proximity.

9. The wearable device of claim 1, wherein the information associated with the second identifier includes health-related information of the second user.

10. A method for monitoring a user's health status using a wearable device, the method comprising:
generating one or more signals responsive to a thermal energy of a first user using a temperature sensor of a wearable device coupled to the first user;
by one or more processors of the wearable device:
receiving said one or more signals generated by the temperature sensor and determining one or more body temperature values of the first user based on said received one or more signals;
detecting a wireless signal strength between a first wireless transceiver of the wearable device and a second wireless transceiver of a separate wearable device that is coupled to a second user;
based on at least the detected wireless signal strength, determining a distance between the wearable device and the separate wearable device;
receiving a second identifier associated with the second user from the separate wearable device;
instructing the first wireless transceiver of the wearable device to transmit to a mobile computing device remote to the wearable device said determined one or more body temperature values continuously regardless of the distance between the wearable device and the separate wearable device; and
in response to determining, based on at least the detected wireless signal strength, that the distance between the wearable device and the separate wearable device is within a threshold proximity, instructing the first wireless transceiver of the wearable device to transmit to the mobile computing device when the wearable device and the separate wearable device are within said threshold proximity:
a first identifier associated with the first user and indicative of an identity of the first user;
the second identifier associated with the second user and indicative of an identity of the second user; and
the distance between the first wearable device and the separate wearable device without location information of the wearable device and the separate wearable device, said mobile computing device configured to wirelessly transmit said first and second identifiers, said one or more body temperature values, and said distance to a remote monitoring system for determination of a risk state of the first user based on analyzing said one or more body temperature values, said distance, and information associated with said second identifier, wherein said risk state indicates a likelihood that said first user has one or more infections.

11. The method of claim 10, wherein said threshold proximity comprises 20 ft.

12. The method of claim 10, further comprising instructing the first wireless transceiver to transmit to the mobile computing device said determined one or more body temperature values continuously every minute.

13. The method of claim 10, further comprising determining said distance based on a detected Bluetooth® signal strength between the first and second wireless transceivers.

14. The method of claim 10, further comprising instructing the first wireless transceiver to transmit to the mobile computing device a duration of time that the distance between the wearable device and the separate wearable device is within the threshold proximity.

15. The method of claim 10, further comprising instructing the first wireless transceiver to transmit to the mobile computing device a number of times that the distance between the wearable device and the separate wearable device is within the threshold proximity.

16. The method of claim 10, wherein the information associated with the second identifier includes health-related information of the second user.

* * * * *